United States Patent
Goldstein et al.

[11] Patent Number: 6,140,342
[45] Date of Patent: Oct. 31, 2000

[54] OXY SUBSTITUTED 4-CARBOXYAMINO-2-METHYL-1,2,3,4-TETRAHYDROQUINOLINES

[75] Inventors: Steven W. Goldstein, Noank; Michael R. Makowski, Salem; Roger B. Ruggeri, Waterford; Ronald T. Wester, Ledyard, all of Conn.

[73] Assignee: Pfizer Inc., New York, N.Y.

[21] Appl. No.: 09/390,731

[22] Filed: Sep. 7, 1999

Related U.S. Application Data

[60] Provisional application No. 60/100,729, Sep. 17, 1998.

[51] Int. Cl.[7] .................... A61K 31/4706; C07D 215/58; C07D 215/42
[52] U.S. Cl. .......................... 514/313; 546/159; 546/160
[58] Field of Search ............................ 514/313; 546/159, 546/160

[56] References Cited

U.S. PATENT DOCUMENTS

| | | | |
|---|---|---|---|
| 5,231,101 | 7/1993 | Honda et al. | 514/290 |
| 5,231,102 | 7/1993 | Baker et al. | 514/312 |
| 5,276,168 | 1/1994 | Atwal | 549/404 |
| 5,288,725 | 2/1994 | Witherup et al. | 514/292 |
| 5,401,848 | 3/1995 | Atwal | 546/153 |

FOREIGN PATENT DOCUMENTS

| | | |
|---|---|---|
| 0818448 | 1/1998 | European Pat. Off. |

OTHER PUBLICATIONS

Chemical Abstracts 123:55716, 1995.
Chemical Abstracts 116:151569, 1991.
Gordon DJ, et al., Circulation. 79(1):8–15, 1989 Jan., "High–density lipoprotein cholesterol and cardiovascular disease. Four prospective American studies".

*Primary Examiner*—D. Margaret Seaman
*Attorney, Agent, or Firm*—Peter C. Richardson; Gregg C. Benson; A. Dean Olson

[57] ABSTRACT

Cholesteryl ester transfer protein inhibitors, pharmaceutical compositions containing such inhibitors and the use of such inhibitors to elevate certain plasma lipid levels, including high density lipoprotein-cholesterol and to lower certain other plasma lipid levels, such as LDL-cholesterol and triglycerides and accordingly to treat diseases which are exacerbated by low levels of HDL cholesterol and/or high levels of LDL-cholesterol and triglycerides, such as atherosclerosis and cardiovascular diseases in some mammals, including humans.

44 Claims, No Drawings

OXY SUBSTITUTED 4-CARBOXYAMINO-2-METHYL-1,2,3,4-TETRAHYDROQUINOLINES

This application claims priority from provisional application U.S. Ser. No. 60/100,729 filed Sep. 17, 1998, the benefit of which is hereby claimed under 37 C.F.R. §1.78 (a)(3).

BACKGROUND OF INVENTION

This invention relates to cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of this condition has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon,D. J., et al.,: "High-density Lipoprotein Cholesterol and Cardiovascular Disease", Circulation, (1989), 79: 8–15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly (~10–12%). As a result, there is a significant unmet medical need for a well-tolerated agent which can significantly elevate plasma HDL levels, thereby reversing or slowing the progression of atherosclerosis.

Thus, although there are a variety of anti-therosclerosis therapies, there is a continuing need and a continuing search in this field of art for alternative therapies.

EP0818448 (970624) discloses the preparation of certain 5,6,7,8 substituted tetrahydroquinolines and analogs as cholesteryl ester transfer protein inhibitors.

U.S. Pat. No. 5,231,102 discloses a class of 4-substituted 1,2,3,4-tetrahydroquinolines that possess an acidic group (or group convertible thereto in vivo) at the 2-position that are specific antagonists of N-methyl-D-aspartate (NMDA) receptors and are therefore useful in the treatment and/or prevention of neurodegenerative disorders.

U.S. Pat. No. 5,288,725 discloses pyrroloquinoline bradykinin antagonists.

SUMMARY OF THE INVENTION

This invention is directed to compounds of Formula I

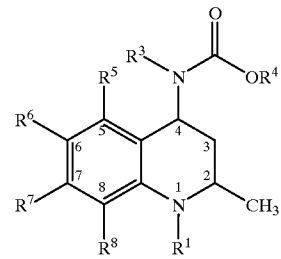

prodrugs thereof, and pharmaceutically acceptable salts of said compounds and said prodrugs;

wherein $R^1$ is hydrogen, Y, W—X, W—Y;

wherein W is a carbonyl, thiocarbonyl, sulfinyl or sulfonyl;

X is —O—Y, —S—Y, —N(H)—Y or —N—$(Y)_2$;

wherein Y for each occurrence is independently Z or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with Z;

wherein Z is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said Z substituent is optionally mono-, di- or tri-substituted independently with halo, $(C_2-C_6)$ alkenyl, $(C_1-C_6)$ alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines;

$R^3$ is hydrogen or Q;

wherein Q is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with V;

wherein V is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said V substituent is optionally mono-, di-, tri-, or tetra-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carbamoyl, mono-N- or di-N,N-$(C_1-C_6)$alkylcarbamoyl, carboxy, $(C_1-C_6)$alkyloxycarbonyl, mono-N- or di-N,N-$(C_1-C_6)$alkylamino wherein said $(C_1-C_6)$alkyl or $(C_2-C_6)$alkenyl substituent is optionally mono-, di- or tri-substituted independently with hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino or said $(C_1-C_6)$alkyl or $(C_2-C_6)$alkenyl substituents are also optionally substituted with from one to nine fluorines;

$R^4$ is $Q^1$ or $V^1$ wherein $Q^1$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with $V^1$;

wherein $V^1$ is a partially saturated, fully saturated or fully unsaturated three to six membered ring optionally having one to two heteroatoms selected independently from oxygen, sulfur and nitrogen;

wherein said $V^1$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R^3$ must contain V or $R^4$ must contain $V^1$; and $R^5$, $R^6$, $R^7$ and $R^8$ are each independently hydrogen, hydroxy or oxy wherein said oxy is substituted with T or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with T;

wherein T is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said T substituent is optionally mono-, di- or tri-substituted independently with halo, $(C_1-C_6)$alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines.

A preferred group of compounds, designated the A Group, contains those compounds having the Formula I as shown above wherein the $C^2$ methyl is beta;

the $C^4$ nitrogen is beta;

$R^1$ is W—X;

W is carbonyl, thiocarbonyl or sulfonyl;

X is —O—Y—, S—Y—, —N(H)—Y— or —N—(Y)$_2$-;

Y for each occurrence is independently Z or $(C_1-C_4)$alkyl, said $(C_1-C_4)$alkyl optionally having from one to nine fluorines or said $(C_1-C_4)$alkyl optionally mono-substituted with Z wherein Z is a partially saturated, fully saturated or fully unsaturated three to six membered ring optionally having one to two heteroatoms selected independently from oxygen, sulfur and nitrogen;

wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl said alkyl substituent is also optionally substituted with from one to nine fluorines;

$R^3$ is Q—V wherein Q is $(C_1-C_4)$alkylene and V is a five or six membered partially saturated, fully saturated or fully unsaturated ring optionally having one to three heteroatoms selected independently from oxygen, sulfur and nitrogen;
  wherein said V ring is optionally mono-, di-, tri- or tetra-substituted independently with halo, $(C_1-C_6)$ alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$ alkyl optionally having from one to nine fluorines;
$R^4$ is $(C_1-C_4)$alkyl;
$R^6$ and $R^7$ are each independently hydrogen or $(C_1-C_6)$ alkoxy, said $(C_1-C_6)$alkoxy optionally having from one to nine fluorines or said $(C_1-C_6)$alkoxy is optionally mono-substituted with T;
  wherein T is a partially saturated, fully saturated or fully unsaturated five to six membered ring optionally having one to two heteroatoms selected independently from oxygen, sulfur and nitrogen;
  wherein said T substituent is optionally mono-, di- or tri-substituted independently with halo, $(C_1-C_6)$ alkyl, hydroxy, $(C_1-C_8)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and
$R^5$ and $R^8$ are H;
and pharmaceutically acceptable salts thereof.

A group of compounds which is preferred among the A Group of compounds designated the B Group, contains those compounds wherein
  W is carbonyl;
  X is O—Y wherein Y is $(C_1-C_4)$alkyl, said $(C_1-C_4)$alkyl optionally having from one to nine fluorines;
  Q is $(C_1-C_4)$alkylene and V is phenyl, pyridinyl, or pyrimidinyl;
    wherein said V ring is optionally mono-, di- or tri-substituted independently with halo, $(C_1-C_8)$alkyl, hydroxy, $(C_1-C_8)$alkoxy, nitro, cyano or oxo wherein said $(C_1-C_6)$alkyl substituent optionally has from one to nine fluorines;
  $R^6$ and $R^7$ are each independently hydrogen or $(C_1-C_3)$ alkoxy, said $(C_1-C_3)$alkoxy optionally having from one to seven fluorines;
and pharmaceutically acceptable salts thereof.

A group of compounds which is preferred among the B Group of compounds designated the C Group, contains those compounds wherein
  Q is methylene and V is phenyl or pyridinyl;
    wherein said V ring is optionally mono-, di- or tri-substituted independently with halo, nitro or $(C_1-C_2)$ alkyl, wherein said $(C_1-C_2)$alkyl substituent optionally has from one to five fluorines;
and pharmaceutically acceptable salts thereof.

Especially preferred compounds of Formula I are the compounds
  [2R,4S]4-[(3,5-dichloro-benzyl)-methoxycarbonyl-amino]-6,7-dimethoxy-2-methyl-3,4-dihydro-2H-quinoline-1-carboxylic acid ethyl ester;
  [2R,4S]4-[(3,5-dinitro-benzyl)-methoxycarbonyl-amino]-6,7-dimethoxy-2-methyl-3,4-dihydro-2H-quinoline-1-carboxylic acid ethyl ester;
  [2R,4S]4-[(2,6-dichloro-pyridin-4-ylmethyl)-methoxycarbonyl-amino]-6,7-dimethoxy-2-methyl-3,4-dihydro-2H-quinoline-1-carboxylic acid ethyl ester;
  [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid ethyl ester;
  [2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester;
  [2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester;
and pharmaceutically acceptable salts of said compounds.

Other especially preferred compounds of Formula I are the compounds
  [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid isopropyl ester;
  [2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;
  [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethyl ester;
  [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid propyl ester;
  [2R,4S]4-[(3,5-bis-trifluoromethyl-benzyl)-methoxycarbonyl-amino]-6,7-dimethoxy-2-methyl-3,4-dihydro-2H-quinoline-1-carboxylic acid tert-butyl ester;
  [2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester;
and pharmaceutically acceptable salts of said compounds.

Especially preferred compounds within the C Group of compounds are compounds wherein
  a. Y is ethyl;
     $R^3$ is 3,5-dichlorophenylmethyl;
     $R^4$ is methyl; and
     $R^6$ and $R^7$ are each methoxy;
  b. Y is ethyl;
     $R^3$ is 3,5-dinitrophenylmethyl;
     $R^4$ is methyl; and
     $R^6$ and $R^7$ are each methoxy;
  c. Y is ethyl;
     $R^3$ is 2,6-dichloropyridin-4-ylmethyl;
     $R^4$ is methyl; and
     $R^6$ and $R^7$ are each methoxy;
  d. Y is ethyl;
     $R^3$ is 3,5-bis-trifluoromethylphenylmethyl;
     $R^4$ is methyl; and
     $R^6$ and $R^7$ are each methoxy;
  e. Y is ethyl;
     $R^3$ is 3,5-bis-trifluoromethylphenylmethyl;
     $R^4$ is methyl;
     $R^6$ is methoxy; and
     $R^7$ is hydrogen;
  f. Y is ethyl;
     $R^3$ is 3,5-bis-trifluoromethylphenylmethyl;
     $R^4$ is methyl;
     $R^6$ is hydrogen; and
     $R^7$ is methoxy;

g. Y is isopropyl;
   $R^3$ is 3,5-bis-trifluoromethylphenylmethyl;
   $R^4$ is methyl; and
   $R^6$ and $R^7$ are each methoxy;

h. Y is ethyl;
   $R^3$ is 3,5-bis-trifluoromethylphenylmethyl;
   $R^4$ is ethyl; and
   $R^6$ and $R^7$ are each methoxy;

i. Y is 2,2,2,-trifluoroethyl;
   $R^3$ is 3,5-bis-trifluoromethylphenylmethyl;
   $R^4$ is methyl; and
   $R^6$ and $R^7$ are each methoxy;

j. Y is n-propyl;
   $R^3$ is 3,5-bis-trifluoromethylphenylmethyl;
   $R^4$ is methyl; and
   $R^6$ and $R^7$ are each methoxy;

k. Y is tert-butyl;
   $R^3$ is 3,5-bis-trifluoromethylphenylmethyl;
   $R^4$ is methyl; and
   $R^6$ and $R^7$ are each methoxy; and l. Y is ethyl;
   $R^3$ is 3,5-bis-trifluoromethylphenylmethyl;
   $R^4$ is methyl;
   $R^6$ is trifluoromethoxy; and
   $R^7$ is hydrogen; and pharmaceutically acceptable salts of said compounds.

A preferred group of compounds, designated the D Group, contains those compounds having the Formula I as shown above wherein the $C^2$ methyl is beta;

the $C^4$ nitrogen is beta;

$R^1$ is W—Y;

W is carbonyl, thiocarbonyl or sulfonyl;

Y is $(C_1-C_6)$alkyl, said $(C_1-C_6)$alkyl optionally having from one to nine fluorines or said $(C_1-C_6)$alkyl is optionally mono-substituted with Z;
   wherein Z is a partially saturated, fully saturated or fully unsaturated three to six membered ring optionally having one to two heteroatoms selected independently from oxygen, sulfur and nitrogen;
   wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl substituent optionally substituted with from one to nine fluorines;

$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;
   wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;
   wherein T is a partially saturated, fully saturated or fully unsaturated five to six membered ring optionally having one to two heteroatoms selected independently from oxygen, sulfur and nitrogen;
   wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H; and pharmaceutically acceptable salts thereof.

A group of compounds which is preferred among the D Group of compounds designated the E Group, contains those compounds wherein W is carbonyl;

Y is $(C_1-C_4)$alkyl, said $(C_1-C_4)$alkyl optionally having from one to nine fluorines;

Q is $(C_1-C_4)$alkylene and V is phenyl, pyridinyl, or pyrimidinyl;
   wherein said V ring is optionally mono-, di- or tri-substituted independently with halo, $(C_1-C_6)$alkyl, hydroxy, $(C_1-C_6)$alkoxy, nitro, cyano or oxo wherein said $(C_1-C_6)$alkyl substituent optionally has from one to nine fluorines; and $R^6$ and $R^7$ are each independently hydrogen or $(C_1-C_3)$alkoxy, said $(C_1-C_3)$alkoxy optionally having from one to seven fluorines; and pharmaceutically acceptable salts thereof.

An especially preferred compound of Formula I is the compound [2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester, or a pharmaceutically acceptable salt of said compound.

An especially preferred compound within the E Group of compounds is the compound wherein Y is n-propyl;

$R^3$ is 3,5-bis-trifluoromethylphenylmethyl;

$R^4$ is methyl; and $R^6$ and $R^7$ are each methoxy, or a pharmaceutically acceptable salt thereof.

A preferred group of compounds, designated the F Group, contains those compounds having the Formula I as shown above wherein the $C^2$ methyl is beta;

the $C^4$ nitrogen is beta:

$R^1$ is Y;

Y is $(C_2-C_6)$alkenyl or $(C_1-C_6)$alkyl, said $(C_2-C_6)$alkenyl or $(C_1-C_6)$alkyl optionally having from one to nine fluorines or said $(C_2-C_6)$alkenyl or $(C_1-C_6)$alkyl optionally mono-substituted with Z;
   wherein Z is a partially saturated, fully saturated or fully unsaturated three to six membered ring optionally having one to two heteroatoms selected independently from oxygen, sulfur and nitrogen;
   wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally substituted with from one to nine fluorines;

$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;

wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^6$ are H; and or a pharmaceutically acceptable salts thereof.

A group of compounds which is preferred among the F Group of compounds, designated the G Group, contains those compounds wherein Y is $(C_1-C_4)$alkyl, said $(C_1-C_4)$alkyl optionally having from one to nine fluorines;

Q is $(C_1-C_4)$alkylene and V is phenyl, pyridinyl, or pyrimidinyl;

wherein said V ring is optionally mono-, di- or tri-substituted independently with halo, $(C_1-C_6)$alkyl, hydroxy, $(C_1-C_6)$alkoxy, nitro, cyano or oxo wherein said $(C_1-C_6)$alkyl substituent optionally has from one to nine fluorines; and $R^6$ and $R^7$ are each independently hydrogen or $(C_1-C_3)$alkoxy, said $(C_1-C_3)$alkoxy optionally having from one to seven fluorines; and pharmaceutically acceptable salts thereof.

Especially preferred compounds of Formula I are the compounds

[2R,4S](3,5-bis-trifluoromethyl-benzyl)-(1-butyl-6,7-dimethoxy-2-methyl-1,2,3,4-tetrahydro-quinolin-4-yl)-carbamic acid methyl ester;

[2R,4S](3,5-bis-trifluoromethyl-benzyl)-[1-(2-ethyl-butyl)-6,7-dimethoxy-2-methyl-1,2,3,4-tetrahydro-quinolin-yl]-carbamic acid methyl ester, hydrochloride;

and pharmaceutically acceptable salts of said compounds.

Especially preferred compounds within the G Group of compounds are compounds wherein a. Y is n-butyl;
  $R^3$ is 3,5-bis-trifluoromethylphenylmethyl;
  $R^4$ is methyl; and
  $R^6$ and $R^7$ are each methoxy; and
b. Y is 2-ethylbutyl;
  $R^3$ is 3,5-bis-trifluoromethylphenylmethyl;
  $R^4$ is methyl; and
  $R^6$ and $R^7$ are each methoxy; and pharmaceutically acceptable salts of said compounds.

A preferred group of compounds, designated the H Group, contains those compounds having the Formula I as shown above wherein the $C^2$ methyl is beta;
the $C^4$ nitrogen is beta:
$R^1$ is Z;
  wherein Z is a partially saturated, fully saturated or fully unsaturated three to six membered ring optionally having one to two heteroatoms selected independently from oxygen, sulfur and nitrogen;
  wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally having one to nine fluorines;

$R^3$ is Q—V;
  wherein Q is $(C_1-C_4)$alkyl and V is a five or six membered partially saturated, fully saturated or fully unsaturated ring optionally having one to three heteroatoms selected independently from oxygen, sulfur and nitrogen;
  wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H; and pharmaceutically acceptable salts thereof.

A preferred group of compounds, designated the I Group, contains those compounds having the Formula I as shown above wherein the $C^2$ methyl is beta;
the $C^4$ nitrogen is beta:
$R^1$ is W—Z;
W is carbonyl, thiocarbonyl or sulfonyl;
Z is a partially saturated, fully saturated or fully unsaturated three to six membered ring optionally having one to two heteroatoms selected independently from oxygen, sulfur and nitrogen;
  wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally having from one to nine fluorines;

$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;

wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H; and pharmaceutically acceptable salts thereof.

Yet another aspect of this invention is directed to methods for treating atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female) by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia treating amount of a Formula I compound, a prodrug thereof, or a pharmaceutically acceptable salt of said compound or of said prodrug.

Yet another aspect of this invention is directed to a method for treating atherosclerosis in a mammal (including a human being) by administering to a mammal in need of such treatment an atherosclerotic treating amount of a Formula I compound, a prodrug thereof, or a pharmaceutically acceptable salt of said compound or of said prodrug.

Yet another aspect of this invention is directed to a method for treating peripheral vascular disease in a mammal (including a human being) by administering to a mammal in need of such treatment a peripheral vascular disease treating amount of a Formula I compound, a prodrug thereof, or a pharmaceutically acceptable salt of said compound or of said prodrug.

Yet another aspect of this invention is directed to a method for treating dyslipidemia in a mammal (including a human being) by administering to a mammal in need of such treatment a dyslipidemia treating amount of a Formula I compound, a prodrug thereof, or a pharmaceutically acceptable salt of said compound or of said prodrug.

Yet another aspect of this invention is directed to a method for treating hyperbetalipoproteinemia in a mammal (including a human being) by administering to a mammal in need of such treatment a hyperbetalipoproteinemia treating amount of a Formula I compound, a prodrug thereof, or a pharmaceutically acceptable salt of said compound or of said prodrug.

Yet another aspect of this invention is directed to a method for treating hypoalphalipoproteinemia in a mammal (including a human being) by administering to a mammal in need of such treatment a hypoalphalipoproteinemia treating amount of a Formula I compound, a prodrug thereof, or a pharmaceutically acceptable salt of said compound or of said prodrug.

Yet another aspect of this invention is directed to a method for treating hypercholesterolemia in a mammal (including a human being) by administering to a mammal in need of such treatment a hypercholesterolemia treating amount of a Formula I compound, a prodrug thereof, or a pharmaceutically acceptable salt of said compound or of said prodrug.

Yet another aspect of this invention is directed to a method for treating hypertriglyceridemia in a mammal (including a human being) by administering to a mammal in need of such treatment a hypertriglyceridemia treating amount of a Formula I compound, a prodrug thereof, or a pharmaceutically acceptable salt of said compound or of said prodrug.

Yet another aspect of this invention is directed to a method for treating familial-hypercholesterolemia in a mammal (including a human being) by administering to a mammal in need of such treatment a familial-hypercholesterolemia treating amount of a Formula I compound, a prodrug thereof, or a pharmaceutically acceptable salt of said compound or of said prodrug.

Yet another aspect of this invention is directed to a method for treating cardiovascular disorders in a mammal (including a human being) by administering to a mammal in need of such treatment a cardiovascular disorder treating amount of a Formula I compound, a prodrug thereof, or a pharmaceutically acceptable salt of said compound or of said prodrug.

Yet another aspect of this invention is directed to a method for treating angina in a mammal (including a human being) by administering to a mammal in need of such treatment an angina treating amount of a Formula I compound, a prodrug thereof, or a pharmaceutically acceptable salt of said compound or of said prodrug.

Yet another aspect of this invention is directed to a method for treating ischemia in a mammal (including a human being) by administering to a mammal in need of such treatment an ischemic disease treating amount of a Formula I compound, a prodrug thereof, or a pharmaceutically acceptable salt of said compound or of said prodrug.

Yet another aspect of this invention is directed to a method for treating cardiac ischemia in a mammal (including a human being) by administering to a mammal in need of such treatment a cardiac ischemic treating amount of a Formula I compound, a prodrug thereof, or a pharmaceutically acceptable salt of said compound or of said prodrug.

Yet another aspect of this invention is directed to a method for treating stroke in a mammal (including a human being) by administering to a mammal in need of such treatment a stroke treating amount of a Formula I compound, a prodrug thereof, or a pharmaceutically acceptable salt of said compound or of said prodrug.

Yet another aspect of this invention is directed to a method for treating a myocardial infarction in a mammal (including a human being) by administering to a mammal in need of such treatment a myocardial infarction treating amount of a Formula I compound, a prodrug thereof, or a pharmaceutically acceptable salt of said compound or of said prodrug.

Yet another aspect of this invention is directed to a method for treating reperfusion injury in a mammal (including a human being) by administering to a mammal in need of such treatment a reperfusion injury treating amount of a Formula I compound, a prodrug thereof, or a pharmaceutically acceptable salt of said compound or of said prodrug.

Yet another aspect of this invention is directed to a method for treating angioplastic restenosis in a mammal (including a human being) by administering to a mammal in need of such treatment an angioplastic restenosis treating amount of a Formula I compound, a prodrug thereof, or a pharmaceutically acceptable salt of said compound or of said prodrug.

Yet another aspect of this invention is directed to a method for treating hypertension in a mammal (including a human being) by administering to a mammal in need of such treatment a hypertension treating amount of a Formula I compound, a prodrug thereof, or a pharmaceutically acceptable salt of said compound or of said prodrug.

Yet another aspect of this invention is directed to a method for treating the vascular complications of diabetes in a mammal (including a human being) by administering to a mammal in need of such treatment a vascular complications of diabetes treating amount of a Formula I compound, a prodrug thereof, or a pharmaceutically acceptable salt of said compound or of said prodrug.

Yet another aspect of this invention is directed to a method for treating obesity in a mammal (including a human being) by administering to a mammal in need of such treatment an obesity treating amount of a Formula I compound, a prodrug thereof, or a pharmaceutically acceptable salt of said compound or of said prodrug.

Yet another aspect of this invention is directed to a method for treating endotoxemia in a mammal (including a human being) by administering to a mammal in need of such treatment an endotoxemia treating amount of a Formula I compound, a prodrug thereof, or a pharmaceutically acceptable salt of said compound or of said prodrug.

A preferred dosage is about 0.001 to 100 mg/kg/day of a Formula I compound, a prodrug thereof, or a pharmaceutically acceptable salt of said compound or of said prodrug. An especially preferred dosage is about 0.01 to 10 mg/kg/day of a Formula I compound, a prodrug thereof, or a pharmaceutically acceptable salt of said compound or of said prodrug.

This invention is also directed to pharmaceutical compositions which comprise a therapeutically effective amount of a compound of Formula I, a prodrug thereof, or a pharmaceutically acceptable salt of said compound or of said prodrug and a pharmaceutically acceptable carrier.

This invention is also directed to pharmaceutical compositions for the treatment of atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being) which comprise a therapeutically effective amount of a compound of Formula I, a prodrug thereof, or a pharmaceutically acceptable salt of said compound or of said prodrug and a pharmaceutically acceptable carrier.

This invention is also directed to pharmaceutical compositions for the treatment of atherosclerosis in a mammal (including a human being) which comprise an atherosclerosis treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of peripheral vascular disease in a mammal (including a human being) which comprise a peripheral vascular disease treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of dyslipidemia in a mammal (including a human being) which comprise a dyslipidemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of hyperbetalipoproteinemia in a mammal (including a human being) which comprise a hyperbetalipoproteinemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of hypoalphalipoproteinemia in a mammal (including a human being) which comprise a hypoalphalipoproteinemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of hypercholesterolemia in a mammal (including a human being) which comprise a hypercholesterolemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of hypertriglyceridemia in a mammal (including a human being) which comprise a hypertriglyceridemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of familial-hypercholesterolemia in a mammal (including a human being) which comprise a familial-hypercholesterolemia treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of angina in a mammal (including a human being) which comprise an angina treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of ischemia in a mammal (including a human being) which comprise an ischemic treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of cardiac ischemia in a mammal (including a human being) which comprise a cardiac ischemic treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of stroke in a mammal (including a human being) which comprise a stroke treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of a myocardial infarction in a mammal (including a human being) which comprise a myocardial infarction treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of reperfusion injury in a mammal (including a human being) which comprise a reperfusion injury treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of angioplastic restenosis in a mammal (including a human being) which comprise an angioplastic restenosis treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of hypertension in a mammal (including a human being) which comprise a hypertension treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of the vascular complications of diabetes in a mammal (including a human being) which comprise a vascular complications of diabetes treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of obesity in a mammal (including a human being) which comprise an obesity treating amount of a compound of Formula I, a prodrug thereof, or a pharmaceutically acceptable salt of said compound or of said prodrug and a pharmaceutically acceptable carrier.

This invention is also directed to pharmaceutical compositions for the treatment of endotoxemia in a mammal (including a human being) which comprise an endotoxemia treating amount of a compound of Formula I, a prodrug thereof, or a pharmaceutically acceptable salt of said compound or of said prodrug and a pharmaceutically acceptable carrier.

This invention is also directed to a pharmaceutical combination composition comprising: a therapeutically effective amount of a composition comprising a first compound, said first compound being a Formula I compound, a prodrug thereof, or a pharmaceutically acceptable salt of said compound or of said prodrug;

a second compound, said second compound being an HMG-CoA reductase inhibitor, an microsomal triglyceride transfer protein (MTP)/Apo B secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant; and/or optionally a pharmaceutical carrier.

Preferred among the second compounds are an HMG-CoA reductase inhibitor and a MTP/Apo B secretion inhibitor.

A particularly preferred HMG-CoA reductase inhibitor is lovastatin, simvastatin, pravastatin, fluvastatin, atorvastatin or rivastatin.

Another aspect of this invention is a method for treating atherosclerosis in a mammal comprising administering to a mammal suffering from atherosclerosis;

a first compound, said first compound being a Formula I compound a prodrug thereof, or a pharmaceutically acceptable salt of said compound or of said prodrug; and a second compound, said second compound being an HMG-CoA reductase inhibitor, an MTP/Apo B secretion inhibitor, a cholesterol absorption inhibitor, a cholesterol synthesis inhibitor, a fibrate, niacin, an ion-exchange resin, an antioxidant, an ACAT inhibitor or a bile acid sequestrant wherein the amounts of the first and second compounds result in a therapeutic effect.

A preferred aspect of the above method is wherein the second compound is an HMG-CoA reductase inhibitor or an MTP/Apo B secretion inhibitor.

A particularly preferred aspect of the above method is wherein the HMG-CoA reductase inhibitor is lovastatin, simvastatin, pravastatin, fluvastatin, atorvastatin or rivastatin.

Yet another aspect of this invention is a kit comprising:

a. a first compound, said first compound being a Formula I compound, a prodrug thereof, or a pharmaceutically acceptable salt of said compound or of said prodrug and a pharmaceutically acceptable carrier in a first unit dosage form;

b. a second compound, said second compound being an HMG CoA reductase inhibitor, an MTP/Apo B secretion inhibitor, a cholesterol absorption inhibitor, a cholesterol synthesis inhibitor, a fibrate, niacin, an ion-exchange resin, an antioxidant, an ACAT inhibitor or a bile acid sequestrant and a pharmaceutically acceptable carrier in a second unit dosage form; and c. means for containing said first and second dosage forms wherein the amounts of the first and second compounds result in a therapeutic effect.

A preferred second compound is an HMG-COA reductase inhibitor or an MTP/Apo B secretion inhibitor.

A particularly preferred HMG-CoA reductase inhibitor is lovastatin, simvastatin, pravastatin, fluvastatin, atorvastatin or rivastatin.

As used herein the term mammals is meant to refer to all mammals which contain CETP in their plasma, for example, rabbits and primates such as monkeys and humans. Certain other mammals e.g., dogs, cats, cattle, goats, sheep and horses do not contain CETP in their plasma and so are not included herein.

The term "treating", "treat" or "treatment" as used herein includes preventative (e.g., prophylactic) and palliative treatment.

By "pharmaceutically acceptable" is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form). Exemplary prodrugs upon cleavage release the corresponding free acid, and such hydrolyzable ester-forming residues of the Formula I compounds include but are not limited to those having a carboxyl moiety wherein the free hydrogen is replaced by $(C_1-C_4)$alkyl, $(C_2-C_7)$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as B-dimethylaminoethyl), carbamoyl-$(C_1-C_2)$alkyl, N,N-di$(C_1-C_2)$alkylcarbamoyl-$(C_1-C_2)$alkyl and piperidino, pyrrolidino- or morpholino$(C_2-C_3)$alkyl.

The following paragraphs describe exemplary ring(s) for the generic ring descriptions contained herein.

Exemplary five to six membered aromatic rings optionally having one or two heteroatoms selected independently from oxygen, nitrogen and sulfur include phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl and pyrazinyl.

Exemplary partially saturated, fully saturated or fully unsaturated five to eight membered rings optionally having one to four heteroatoms selected independently from oxygen, sulfur and nitrogen include cyclopentyl, cyclohexyl, cycloheptyl, cyclooctyl and phenyl. Further exemplary five membered rings include 2H-pyrrolyl, 3H-pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl.

Further exemplary six membered rings include 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5 -oxathiazinyl, 1,4-oxazinyl, o-isoxazinyl, p-isoxazinyl, 1,2,5-oxathiazinyl, 1,2,6-oxathiazinyl, 1,4,2-oxadiazinyl and 1,3,5,2-oxadiazinyl. Further exemplary seven membered rings include azepinyl, oxepinyl, and thiepinyl.

Further exemplary eight membered rings include cyclooctyl, cyclooctenyl and cyclooctadienyl.

Exemplary bicyclic rings consisting of two fused partially saturated, fully saturated or fully unsaturated five or six membered rings, taken independently, optionally having one to four heteroatoms selected independently from nitrogen, sulfur and oxygen include indolizinyl, indolyl, isoindolyl, 3H-indolyl, 1H-isoindolyl, indolinyl, cyclopenta(b) pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)-pyridinyl, pyrido(3,2-b)-pyridinyl, pyrido(4,3-b)-pyridinyl, 2H-1,3-benzoxazinyl, 2H-1,4benzoxazinyl, 1H-2,3-benzoxazinyl, 4H-3,1-benzoxazinyl, 2H-1,2-benzoxazinyl and 4H-1,4-benzoxazinyl.

By alkylene is meant saturated hydrocarbon (straight chain or branched) wherein a hydrogen atom is removed from each of the terminal carbons. Exemplary of such groups (assuming the designated length encompasses the particular example) are methylene, ethylene, propylene, butylene, pentylene, hexylene, heptylene).

By halo is meant chloro, bromo, iodo, or fluoro.

By alkyl is meant straight chain saturated hydrocarbon or branched chain saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By alkoxy is meant straight chain saturated alkyl or branched chain saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

As used herein the term mono-N- or di-N,N-$(C_1-C_x)$alkyl . . . refers to the $(C_1-C_x)$alkyl moiety taken independently when it is di-N,N-$(C_1-C_x)$alkyl . . . (x refers to integers).

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

References (e.g., claim 1) to "said carbon" in the phrase "said carbon is optionally mono-, di- or tri-substituted independently with halo, said carbon is optionally mono-substituted with hydroxy, said carbon is optionally mono-substituted with oxo" refers to each of the carbons in the carbon chain including the connecting carbon.

References to "Nitrogen . . . di-substituted with oxo" herein (e.g., claim 1) refer to a terminal nitrogen which constitutes a nitro functionality.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate. The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction-inert solvent" and "inert solvent" refers to a solvent or a mixture thereof which does not interact with starting materials, reagents, intermediates or products in a manner which adversely affects the yield of the desired product.

The term "cis" refers to the orientation of two substituents with reference to each other and the plane of the ring (either both "up" or both "down"). Analogously, the term "trans" refers to the orientation of two substituents with reference to each other and the plane of the ring (the substituents being on opposite sides of the ring).

Alpha and Beta refer to the orientation of a substituent with reference to the plane of the ring (i.e., page). Beta is above the plane of the ring (i.e., page) and Alpha is below the plaine of the ring (i.e., page).

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates and solvates of the compounds of this invention are also included.

It will be recognized that the compounds of this invention can exist in radiolabelled form, i.e., said compounds may contain one or more atoms containing an atomic mass or mass number different from the atomic mass or mass number usually found in nature. Radioisotopes of hydrogen, carbon, phosphorous, fluorine and chlorine include $^3$H, $^{14}$C, $^{32}$P, $^{35}$S, $^{18}$F and $^{36}$Cl, respectively. Compounds of this invention, a prodrug thereof, or a pharmaceutically acceptable salt of said compound or of said prodrug which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability. Radiolabelled compounds of Formula I of this invention and prodrugs thereof can generally be prepared by methods well known to those skilled in the art. Conveniently, such radiolabelled compounds can be prepared by carrying out the procedures disclosed in the Schemes and/or in the Examples and Preparations below by substituting a readily available radio-labelled reagent for a non-radiolabelled reagent.

DTT means dithiothreitol. DMSO means dimethyl sulfoxide. EDTA means ethylenediamine tetraacetic acid.

Other features and advantages of this invention will be apparent from this specification and the appendant claims which describe the invention.

DETAILED DESCRIPTION OF THE INVENTION

In general the compounds of this invention can be made by processes which include processes analogous to those known in the chemical arts, particularly in light of the description contained herein. Certain processes for the manufacture of the compounds of this invention are provided as further features of the invention and are illustrated by the following reaction schemes. Other processes may be described in the experimental section.

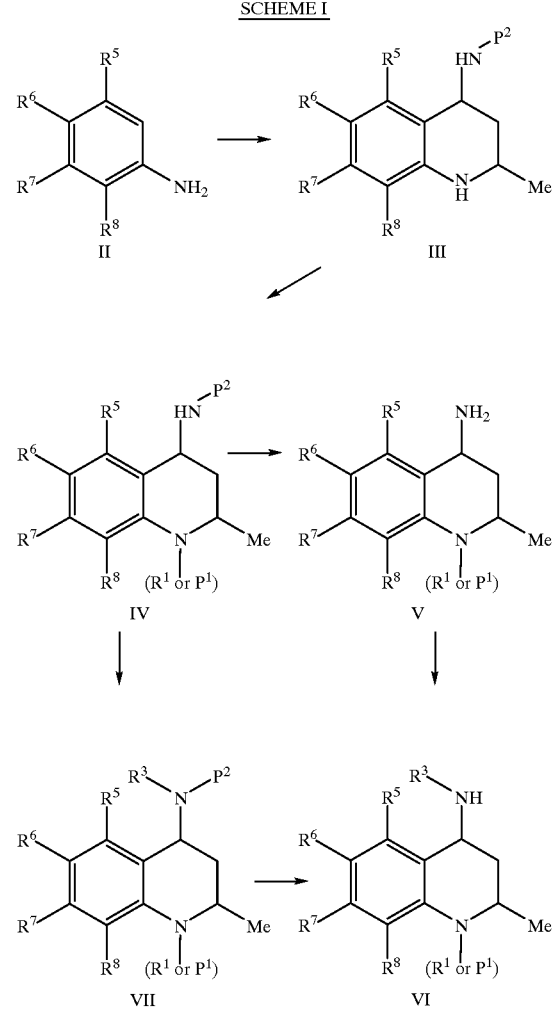

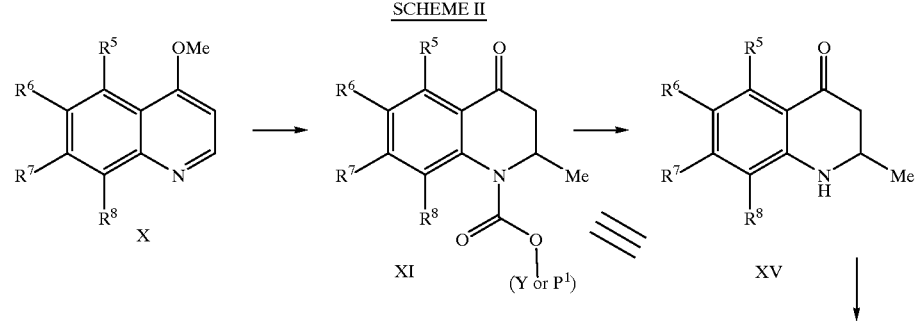

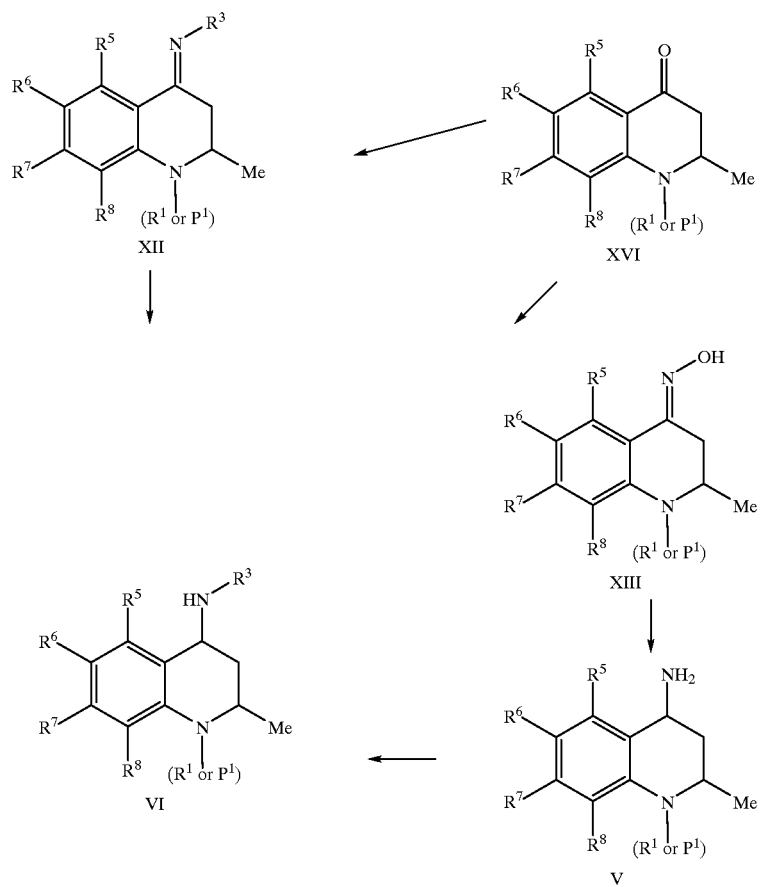
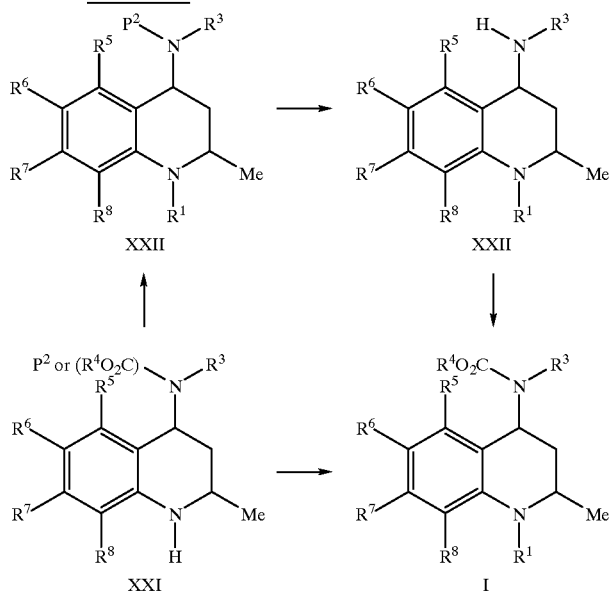

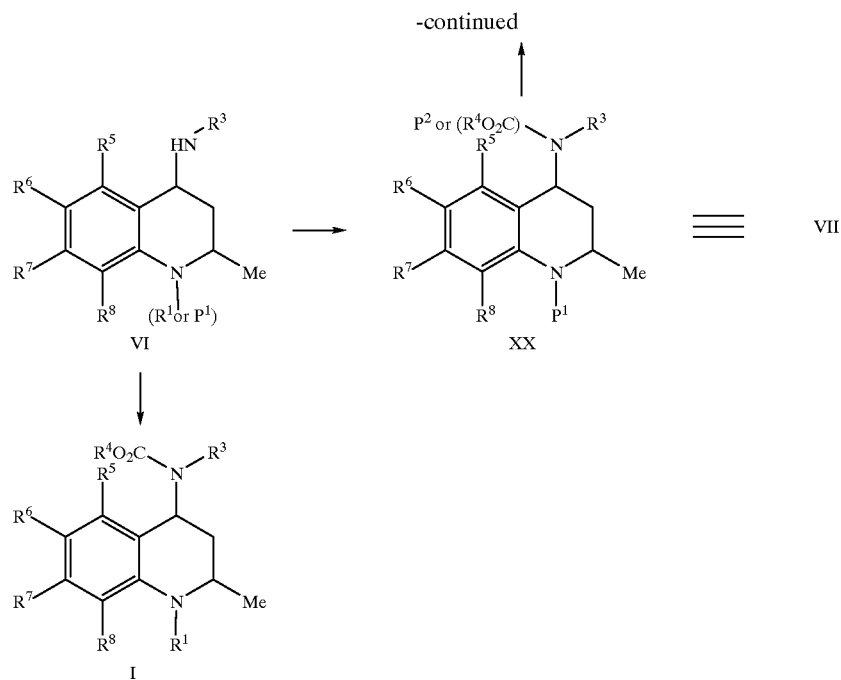

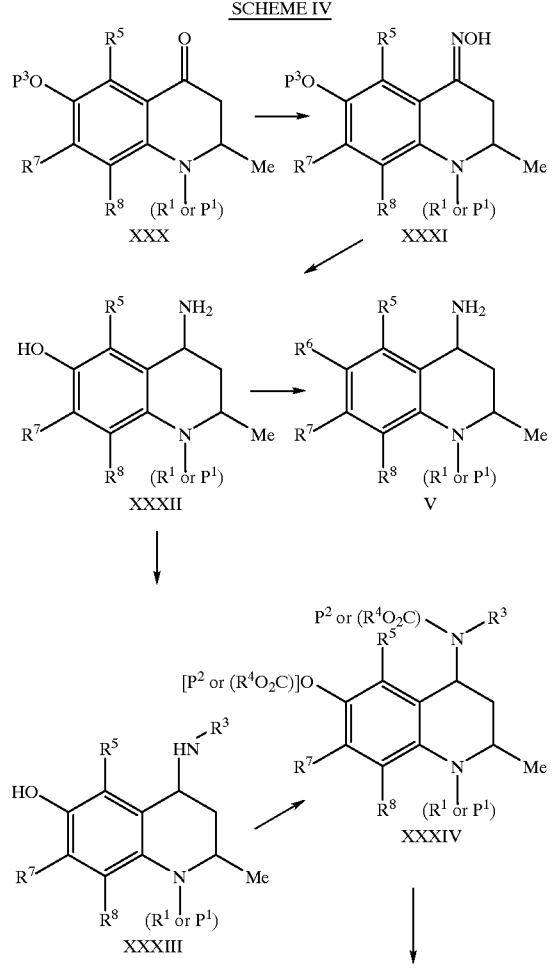

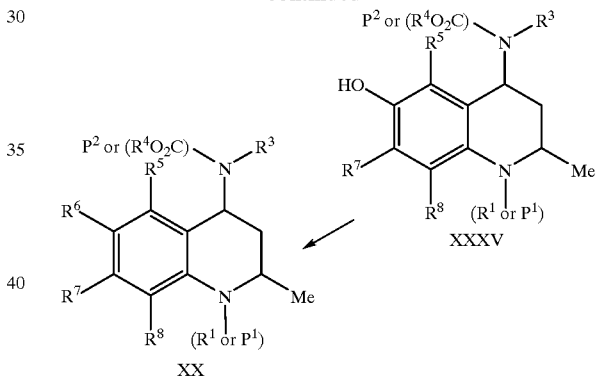

As an initial note, in the preparation of the Formula I compounds it is noted that some of the preparation methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, in Reaction Schemes I and II certain Formula I compounds contain primary amines or carboxylic acid functionalities which may interfere with reactions at other sites of the molecule if left unprotected. Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl, benzyloxycarbonyl, and 9-fluorenylmethylenoxycarbonyl for amines and lower alkyl or benzyl esters for carboxylic acids) which are generally not chemically reactive under the reaction conditions described and can typically be removed without chemically altering other functionality in the Formula I compound.

According to Reaction Scheme I, the Formula III compounds wherein $R^5$, $R^6$, $R^7$, and $R^8$ are as described above and $P^2$ is an appropriate protecting group may be prepared from the appropriate Formula II aromatic amine wherein $R^5$, $R^6$, $R^7$ and $R^8$ are as described above.

The Formula III tetrahydroquinoline is prepared by treating the appropriate Formula II aromatic amine with the requisite acetaldehyde in an inert solvent such as a hydrocarbon (e.g., hexanes, pentanes or cyclohexane), an aromatic hydrocarbon (e.g., benzene, toluene or xylene), a halocarbon (e.g., dichloromethane, chloroform, carbon tetrachloride or dichloroethane), an ether (e.g., diethyl ether, diisopropyl ether, tetrahydrofuran, tetrahydropyran, dioxane, dimethoxyethane, methyl tert-butyl ether, etc.), a nitrile (e.g., acetonitrile or propionitrile), a nitroalkane (e.g., nitromethane or nitrobenzene), preferably dichloromethane with a dehydrating agent (e.g., sodium sulfate or magnesium sulfate) at a temperature of about 0° C. to about 100° C. (preferably ambient temperature) for 1–24 hours (preferably 1 hour). The resulting solution is treated with a suitably substituted (e.g., benzyloxycarbonyl, t-butoxycarbonyl, methoxycarbonyl, formyl-, acetyl-, diallyl- or dibenzyl-), preferably carboxybenzyloxy-, N-vinyl species and with a Lewis acid (e.g., boron trifluoride, boron trifluoride etherate, zinc chloride, titanium tetrachloride, iron trichloride, aluminum trichloride, alkyl aluminum dichloride, dialkyl aluminum chloride or ytterbium (III) triflate; preferably boron trifluoride etherate) or a protic acid such as a hydrohalogenic acid (e.g., fluoro, chloro, bromo or iodo), an alkyl sulfonic acid (e.g., p-toluene, methane or trifloromethane) or carboxylic acid (e.g., formic, acetic, trifluoroacetic or benzoic) at a temperature of from about –78° C. to about 50° C. (preferably ambient temperature) for 0.1 to 24 hours (preferably 1 hour).

Alternatively, the Formula II amine and acetaldehyde may be condensed by treating a solution of the amine and an alkyl amine base (preferably triethyl amine) in a polar aprotic solvent (preferably dichloromethane) with titanium tetrachloride in a polar aprotic solvent (preferably in dichloromethane) at a temperature between about –78° C. to about 40° C. (preferably 0° C.) followed by treatment with acetaldehyde at a temperature between about –78° C. to about 40° C. (preferably 0° C.). The reaction is allowed to proceed for about 0.1 to about 10 hours (preferably 1 hour) at a temperature between about 0° C. to about 40° C. (preferably room temperature) yielding the imine which is reacted with the N-vinyl species as above.

The compounds of Formula IV wherein $R^1$, $R^5$, $R^6$, $R^7$ and $R^8$ are as described above and $P^2$ and $P^2$ are protecting groups may be prepared from the corresponding Formula III amine by various amine reaction routes known to those skilled in the art.

Thus, the Formula IV compounds wherein $R^1$, $R^5$, $R^6$, $R^7$, and $R^8$ are as described above and $P^1$ and $P^2$ are appropriately differentiated protecting groups for the amine moieties are prepared from the corresponding Formula III tetrahydroquinoline employing standard methods for derivatizing amines into the functional groups described for $R^1$ above, see Richard Larock, *Comprehensive Organic Transformations*, VCH Publishers Inc., New York, 1989 and Jerry March, *Advanced Organic Chemistry*, John Wiley & Sons, New York, 1985. For example, a Formula III compound is treated with the appropriate thiocarbonyl chloride, sulfonyl chloride, or sulfinyl chloride, isocyanate or thioisocyanate in a polar aprotic solvent (preferably dichloromethane) in the presence of a base (preferably pyridine) at a temperature of from about –78° C. to about 100° C. (preferably starting at 0° C. and letting warm to room temperature) for a period of 1 to 24 hours (preferably 12 hours).

Formula IV carbamate and urea compounds (wherein $R^1$ is W=C(O), X=O—Y, S—Y, N(H)—Y, or NY$_2$) may be prepared from the Formula III amines via the corresponding carbamoyl chlorides by treating the Formula III amine with a phosgene solution in a hydrocarbon solvent (preferably toluene) at a temperature between about 0° C. and about 200° C. (preferably at reflux) for between 0.1 and 24 hours (preferably 2 hours).

The corresponding ureas may be prepared by treating a solution of the carbamoyl chlorides (prepared as described above) with the appropriate amine in a polar solvent (preferably dichloromethane) at a temperature between about –78° C. and about 100° C. (preferably ambient temperature) for between 1 and 24 hours (preferably 12 hours).

The corresponding carbamate may be prepared by treating a solution of the carbamoyl chlorides (prepared as described above) with the appropriate alcohol and a suitable base (preferably sodium hydride) in a polar solvent (preferably dioxane) at a temperature between about –78° C. and about 100° C. (preferably ambient temperature) for between 1 and 24 hours (preferably 12 hours).

Alternatively, the corresponding carbamate may be prepared by treating a solution of the carbamoyl chlorides at a temperature between about 0° C. and about 200° C. in the appropriate alcohol for between 1 and 240 hours (preferably 24 hours).

The Formula IV compound wherein $R^1$ is Y may be prepared using methods known to those skilled in the art to introduce Y substituents such as an alkyl or alkyl linked substituent. Methods include, for example, formation of the amide from the amine of Formula III and an activated carboxylic acid followed by reduction of the amide with borane in an etheral solvent such as tetrahydrofuran. Alternatively, the alkyl or alkyl linked substituent may be appended by reduction after condensing the amine of Formula III with the required carbonyl containing reactant. Also, the amine of Formula III may be reacted with the appropriate alkyl or aryl halide according to methods known to those skilled in the art.

Thus, the Formula III amine and an acid (e.g., halogenic, sulfuric, sulfonic or carboxylic, preferably acetic) are treated with the appropriate carbonyl containing reactant in a polar solvent (preferably ethanol) at a temperature of about 0° C. to about 100° C. (preferably room temperature) for about 0.1 to 24 hours (preferably 1 hour) followed by treatment with a hydride source (e.g., sodium borohydride, sodium cyanoborohydride, preferably sodium triacetoxyborohydride) at a temperature of about 0° C. to about 100° C. (preferably ambient temperature) for 0.1 to 100 hours (preferably 5 hours).

The Formula V amine wherein $R^1$, $R^5$, $R^6$, $R^7$, and $R^8$ are as described above and $P^1$ is a protecting group may be prepared from the corresponding Formula IV compound by deprotection ($P^2$) using methods known to those skilled in the art, including hydrogenolysis, treatment with an acid (e.g., trifluoroacetic acid, hydrobromic), a base (sodium hydroxide), or reaction with a nucleophile (e.g. sodium methylthiolate, sodium cyanide, etc.) and for the trialkylsilylethoxy carbonyl group a fluoride is used (e.g., tetrabutyl ammonium fluoride). For removal of a benzyloxycarbonyl group, hydrogenolysis is performed by treating the Formula IV compound with a hydride source (e.g., 1 to 10 atmospheres of hydrogen gas: cyclohexene or ammonium formate, in the presence of a suitable catalyst (e.g., 5–20% palladium on carbon, palladium hydroxide; preferably 10% palladium on carbon) in a polar solvent (e.g., methanol, ethanol or ethyl acetate; preferably ethanol) at a temperature between about −78° C. and about 100° C., preferably ambient temperature, for 0.1 to 24 hours, preferably 1 hour.

The compounds of Formula VI wherein $R^1$, $R^3$, $R^5$, $R^6$, $R^7$ and $R^8$ are as described above and $P^1$ is a protecting group as described above may be prepared from the corresponding Formula V amine by various amine reaction routes known to those skilled in the art.

The Formula VI secondary amine wherein $R^3$ is as described above may be prepared using methods known to those skilled in the art to introduce $R^8$ substituents such as an alkyl or alkyl linked substituent. Methods include, for example, formation of an amide from the amine and an activated carboxylic acid followed by reduction of the amide with borane in an etheral solvent such as tetrahydrofuran. Alternatively, an alkyl or alkyl linked substituent may be appended by reduction of the appropriate imine, the imine being formed by condensing the amine with the required carbonyl containing reactant. Also, the amine may be reacted with the appropriate alkyl halide according to methods known to those skilled in the art.

Thus, the Formula V amine and an acid (e.g., halogenic, sulfuric, sulfonic or carboxylic, preferably hydrochloric) are treated with the appropriate carbonyl containing reagent in a polar solvent (preferably dichloromethane) at a temperature of about 0° C. to about 100° C. (preferably room temperature) for about 0.1 to 24 hours (preferably 1 hour) followed by treatment with a hydride source (e.g., sodium borohydride or sodium cyanoborohydride; preferably sodium triacetoxyborohydride) at a temperature of about 0° C. to about 100° C. (preferably ambient temperature) for 0.1 to 100 hours (preferably 5 hours).

The Formula VII compound wherein $R^1$, $R^3$, $R^5$, $R^6$, $R^7$ and $R^8$ are as described above and $P^1$ and $P^2$ are protecting groups may be prepared from the corresponding Formula IV compound by methods known to those skilled in the art; for example, the methods described for the introduction of the $R^8$ substituent above in the transformation of the Formula V compound to the Formula VI compound. Following this, the corresponding Formula VI compound may be prepared from the Formula VII compound by appropriate deprotection such as the methods described above for the transformation of the Formula IV compound to the Formula V compound.

When $R^3$ is H and $R^4$ is as described above, $R^4$ may be represented by $R^3$ in the Formulas VI and VII in Scheme I, thus providing a synthetic scheme for such compounds.

According to Scheme II, the Formula XI dihydroquinolone compounds wherein $R^5$, $R^6$, $R^7$, $R^8$ and Y are as described above, and $P^1$ is a protecting group, may be prepared from the corresponding Formula X quinolines by treatment with a metallo-methyl species and a chloroformate followed by hydrolysis.

Thus, a mixture of the Formula X quinoline and an excess (preferably 1.5 equivalents) of a methyl magnesium species (Grignard reagent) in a polar aprotic solvent (e.g., diethyl ether or dichloromethane; preferably tetrahydrofuran) is treated with an excess (preferably 1.5 equivalents) of a Y— or $P^1$-chloroformate at a temperature between about −100° C. and about 70° C. (preferably −78° C.) followed by warming to a temperature between about 0° C. and about 70° C. (preferably ambient temperature) for between 0.1 and 24 hours (preferably 1 hour). The resulting mixture is combined with an excess (preferably 2 equivalents) of an aqueous acid (preferably 1 molar hydrochloric acid) and mixed vigorously for between 0.1 and 24 hours (preferably 1 hour, or until hydrolysis of the intermediate enol ether is determined to be complete).

Of course, the Formula XI compounds are the final Formula XVI compounds wherein $R^1$ is —C(O)OY or $P^1$ is —C(O)O$P^1$ without further transformation.

The Formula XV compounds wherein $R^5$, $R^6$, $R^7$ and $R^8$ are as described above may be prepared from the corresponding Formula XI dihydroquinolone by appropriate deprotection (including spontaneous decarboxylation) as described for the transformation of the Formula IV compound to the Formula V compound.

The Formula XVI compounds wherein $R^1$, $R^5$, $R^6$, $R^7$ and $R^8$ are as described above and $P^1$ is a protecting group may be prepared from the corresponding Formula XV dihydroquinolone as described for the transformation of the Formula III compound to the Formula IV compound. In certain cases where the reagent has also reacted on the 4-position carbonyl oxygen, the substituent may be conveniently removed by treatment with acid (e.g., aqueous HCl) or base (e.g., aqueous sodium hydroxide).

Again, for those Formula XVI compounds wherein $R^1$ or $P^1$ is the same as for the Formula XI compound such transformation as described above is not needed.

The Formula VI amine compounds wherein $R^1$, $R^3$, $R^5$, $R^6$, $R^7$ and $R^8$ are as described above and $P^1$ is a protecting group may be prepared from the corresponding Formula XVI dihydroquinolone by a reductive amination sequence. The Formula XVI dihydroquinolone, an excess (preferably 1.1 equivalents) of an $R^8$-amine and an excess (preferably 7 equivalents) of an amine base (preferably triethylamine) in a polar solvent (preferably dichloromethane) are treated with 0.5 to 1.0 equivalents (preferably 0.55 equivalents) of titanium tetrachloride as a solution in a suitable polar solvent (preferably dichloromethane) at a temperature between about 0° C. and about 40° C. (preferably ambient temperature) for between 1 to 24 hours (preferably 12 hours). The resulting Formula XII imine is reduced by treatment with a reducing agent (preferably sodium borohydride) in an appropriate polar solvent (preferably ethanol) at a temperature between about 0° C. and about 80° C. (preferably room temperature) for between 1 and 24 hours (preferably 12 hours) resulting in a mixture of diastereomeric Formula VI amines, generally favoring the trans isomer. Alternatively, the reduction may be performed by treating the Formula XII imine directly with an excess (preferably 5 equivalents) of zinc borohydride as a solution in ether (preferably 0.2 molar) at a temperature between about 0° C. and about 40° C. (preferably ambient temperature) for between 1 and 24 hours (preferably 12 hours) resulting in a mixture of diastereomeric Formula VI, amines, generally favoring the cis isomer.

Alternatively, the Formula VI amine wherein $R^1$, $R^3$, $R^5$, $R^6$, $R^7$ and $R^8$ are as described above and $P^1$ is a protecting group may be prepared from the corresponding Formula XVI dihydroquinolones by formation of an oxime, reduction and substitution of the amine. Thus, the Formula XVI dihydroquinolone, excess (preferably 3 equivalents) hydroxylamine hydrochloride and an excess (preferably 2.5 equivalents) of base (preferably sodium acetate) are reacted at a temperature between about 0° C. and about 100° C. (preferably at reflux) for between 1 and 24 hours (preferably 2 hours) in a polar solvent (preferably ethanol). The resulting Formula XIII oxime is treated with excess (preferably 6 equivalents) aqueous base (preferably 2N potassium hydroxide) in a polar solvent (preferably ethanol) and an excess (preferably 4 equivalents) of a nickel-aluminum alloy (preferably 1:1 by weight) at a temperature between about 0° C. and about 100° C. (preferably ambient temperature) for between 0.25 and 24 hours (preferably 1 hour). The resulting Formula V amine is obtained as a diastereomeric mixture generally (favoring the cis isomer).

The Formula VI secondary amine wherein $R^1$, $R^3$, $R^5$, $R^7$ and $R^8$ are as described above and $P^1$ is a protecting group may be prepared from the appropriate Formula V amine as described in Scheme I for the transformation of the Formula V compound to the Formula VI compound.

According to Scheme III the Formula I compounds as described above may be prepared from the appropriate Formula VI compounds by conversion to the desired carbamate. Thus, the Formula VI amine is treated with the appropriate activated carbonate (e.g., chloroformate, dicarbonate or carbonyl diimidazole) followed by the appropriate alcohol) in a polar solvent (preferably dichloromethane) in the presence of an excess of amine base (preferably pyridine) at a temperature between about −20° C. and about 40° C. (preferably ambient temperature) for between 1 and 24 hours (preferably 12 hours) to yield the Formula I compound.

Alternatively, according to Scheme III, where appropriate, if the functionality at $R^1$ is incompatible with the reaction to form the Formula I compound, then the P protected Formula VI compound may be transformed to the Formula I compound through protection/deprotection sequences and introduction of the desired substituents. Thus, the Formula VI amine is treated with the appropriate reagent (e.g., protecting group precursor, activated carbonate (e.g., chloroformate, dicarbonate or carbonyl imidazole)) in a polar solvent (preferably dichloromethane) in the presence of an excess of amine base (preferably pyridine) at a temperature between about −20° C. and about 40° C. (preferably ambient temperature) for between 1 and 24 hours (preferably 12 hours) to yield the Formula XX compound.

Also, the Formula XX compounds, wherein $P^2$ is present may be obtained as shown in Scheme I for the Formula VII compounds (having $P^4$).

The Formula XXI amines wherein $R^3$, $R^5$, $R^6$, $R^7$, $R^8$ and $R^4$ are as described above and $P^2$ is a protecting group may be prepared from the Formula XX compound by selective deprotection of $P^1$.

When $P^1$ is, for example, t-butoxycarbonyl, the Formula XXI compound is conveniently prepared by treatment with an acid (preferably trifluorooacetic acid) at a temperature between about 0° C. and about 100° C. (preferably room temperature) for 0.1 to 24 hours (preferably 1 hour).

The compounds of Formula I or compounds of Formula XXII (wherein $R^4$ is as described above) may be prepared from the corresponding Formula XXI amine (wherein $R^4$ or $P^2$ is present respectively) by various amine reaction routes known to those skilled in the art, for example, those described in Scheme I for the transformation of the Formula III compound to the Formula IV compound.

The Formula XXIII amines may be prepared from the Formula XXII compounds by suitable deprotection. When $P^2$ is, for example, benzyloxycarbonyl, the Formula XXIII compound is prepared by treatment with an excess of a hydride source (e.g., cyclohexene, hydrogen gas or preferably ammonium formate) in the presence of 0.01 to 2 equivalents (preferably 0.1 equivalent) of a suitable catalyst (preferably 10% palladium on carbon) in a polar solvent (preferably ethanol) at a temperature between about 0° C. and about 100° C. (preferably room temperature) for 0.1 to 24 hours (preferably 1 hour).

The Formula I compound wherein $R^4$ is as described above may be prepared using the methods described for the conversion of the Formula VI compound to the Formula I compound in Scheme III above.

According to Scheme IV the Formula V compounds wherein $R^4$, $R^5$, $R^7$ and $R^8$ are as described above, and $R^6$ is an ether linked moiety can be obtained from the Formula XXX quinolones having a $OP^3$ moiety, wherein $P^3$ is a protecting group, at the $R^6$ position employing the following methods. In addition, in an analogous manner such processes may be used to prepare the corresponding compounds wherein $R^6$, $R^7$, or $R^8$ are an ether linked moiety starting from the corresponding Formula XXX compound having an $OP^3$ moiety at either the $R^6$, $R^7$, or $R^8$ positions.

Thus, the Formula XXX quinolone is combined with hydroxylamine hydrochloride and a mineral base (preferably sodium acetate) in a polar solvent (preferably ethanol) at a temperature between about 0° C. and about 100° C. (preferably at reflux) for between 1 and 24 hours (preferably 2 hours) to yield the Formula XXXI oxime.

The Formula XXXI oxime is treated with an excess (preferably six equivalents) of an aqueous base (preferably 2N potassium hydroxide) and an excess (preferably four equivalents) of a nickel-aluminum alloy (preferably 1:1 by weight) in a polar solvent (preferably ethanol) at a temperature between about 0° C. and about 100° C. (preferably ambient temperature) for between 0.25 and 24 hours (preferably 2 hours) to prepare the corresponding Formula XXXII amine. If necessary, the $P^3$ protecting group may be removed using standard methods if the oxime transformation does not result in such cleavage.

Alternatively, the Formula XXX compound may be deprotected (removal of the $P^3$) by methods known to those skilled in the art prior to formation of the Formula XXXI oxime which can then be reduced to form the Formula XXXII amine.

The Formula V compound wherein $R^6$ is an oxy-linked moiety may be prepared by treating the Formula XXXII alcohol under, for example, Mitsunobu conditions. Thus, the appropriate phenol is treated with a phosphine (preferably triphenylphosphine) and an azodicarboxylate (preferably bis-(N-methylpiperazinyl)-azodicarboxamide) and the required alcohol in a polar solvent (preferably benzene).

Of course, via Schemes I and II the resulting Formula V compound may be transformed into the Formula VI precursors for the Formula I compounds of this invention.

Alternatively, the Formula XX compound wherein $R^6$ is an ether linked moiety and wherein $R^1$, $R^3$ and $R^4$ are as described above (secondary amines) and $P^1$ and $P^2$ are protecting groups may be prepared from the Formula XXXII alcohols as described below. In addition, in an analogous manner such processes may be used to prepare the corresponding compounds wherein $R^5$, $R^7$, or $R^8$ are an ether linked moiety starting from the corresponding Formula XXXII compound and thus ultimately the Formula XXX compound (i.e., the Formula XXX compound having a $P^3O$— at either the $R^5$, $R^7$, or $R^8$ positions).

The Formula XXXIII secondary amine wherein $R^3$ is as described above may be prepared from the corresponding Formula XXXII compound according to methods in Scheme I described above for the conversion of the Formula V compound to the Formula VI compound.

The Formula XXXIV compounds wherein $R^4$ is as described above may be prepared from Formula XXXIII amines by methods analogous to that described in Scheme III for the transformation of the Formula VI compound to the Formula XX compound.

The Formula XXXV phenol may be selectively deprotected for example when $R^4O_2CO$— is present by treating the Formula XXXIV carbonate with potassium carbonate in a polar solvent (preferably methanol) at a temperature between about 0° C. and about 100° C. (preferably ambient temperature) for between 1 and 24 hours (preferably 12 hours).

The corresponding XX ethers may be prepared from the Formula XXXV phenol using for example, the Mitsunobu conditions described above for the conversion of the Formula XXXII compounds to the Formula V compounds. Of course, one skilled in the art will appreciate that the phenol may be derivatized to a variety of functional groups using standard methods, for example, as described in March or Larock, or by conversion to the corresponding triflate for use in a variety of reactions involving transition metal catalysis.

Prodrugs of the compounds of Formula I may be prepared according to methods known to those skilled in the art. Exemplary processes are described below.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0 to 100° C. for about 1 to about 24 hours. Alternatively the acid is combined with appropriate alcohol as solvent in the presence of a catalytic amount of acid such as concentrated sulfuric acid at a temperature of about 20 to 100° C., preferably at a reflux, for about 1 hour to about 24 hours. Another method is the reaction of the acid with a stoichiometric amount of the alcohol in the presence of a catalytic amount of acid in an inert solvent such as toluene or tetrahydrofuran, with concomitant removal of the water being produced by physical (e.g., Dean-Stark trap) or chemical (e.g., molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0 to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl)amides, N-(1-hydroxy-1-(alkoxycarbonyl)methyl)amides may be prepared by the reaction of the parent amide with the appropriate aldehyde under neutral or basic conditions (e.g., sodium ethoxide in ethanol) at temperatures between 25 and 70° C. N-alkoxymethyl or N-1-(alkoxy)alkyl derivatives can be obtained by reaction of the N-unsubstituted compound with the necessary alkyl halide in the presence of a base in an inert solvent.

The compounds of this invention may also be used in conjunction with other pharmaceutical agents (e.g., LDL-cholesterol lowering agents, triglyceride lowering agents) for the treatment of the disease/conditions described herein. For example, they may be used in combination with cholesterol synthesis inhibitors, cholesterol absorption inhibitors, MTP/Apo B secretion inhibitors, and other cholesterol lowering agents such as fibrates, niacin, ion-exchange resins, antioxidants, ACAT inhibitors and bile acid sequestrants. In combination therapy treatment, both the compounds of this invention and the other drug therapies are administered to mammals (e.g., humans, male or female) by conventional methods.

Any HMG-CoA reductase inhibitor may be used as the second compound in the combination aspect of this invention. The term HMG-COA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e. g., Meth. Enzymol. 1981; 71:455–509 and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus Aspergillus, such as lovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as rivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin.

Any MTP/Apo B secretion (microsomal triglyceride transfer protein and or apolipoprotein B) inhibitor may be used as the second compound in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e. g., Wetterau, J. R. 1992; Science 258:999). A variety of these compounds are described and referenced below however other MTP/Apo B secretion inhibitors will be known to those skilled in the art.

WO 96/40640 and WO 98/23593 are two exemplary publications.

For example, the following MTP/Apo B secretion inhibitors are particularly useful:

4'-trifluoromethyl-biphenyl-2-carboxylic acid [2-(1H-[1,2,4,]triazol-3-ylmethyl)-1,2,3,4-tetrahydro-isoquinolin-6-yl]-amide;

4'-trifluoromethyl-biphenyl-2-carboxylic acid [2-(2-acetylamino-ethyl)-1,2,3,4-tetrahydro-isoquinolin-6-yl]-amide;

(2-{6-[(4'-trifluoromethyl-biphenyl-2-carbonyl)-amino]-3,4-dihydro-1H-isoquinolin-2-yl)}ethyl)-carbamic acid methyl ester;

4'-trifluoromethyl-biphenyl-2-carboxylic acid [2-(1H-imidazol-2-ylmethyl)-1,2,3,4-tetrahydro-isoquinolin-6-yl]-amide;

4'-trifluoromethyl-biphenyl-2-carboxylic acid [2-(2,2-diphenyl-ethyl)-1,2,3,4-tetrahydro-isoquinolin-6-yl]-amide; and 4'-trifluoromethyl-biphenyl-2-carboxylic acid [2-(2-ethoxy-ethyl)-1,2,3,4-tetrahydro-isoquinolin-6-yl]-amide.

Any HMG-CoA synthase inhibitor may be used as the second compound in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth Enzymol. 1975; 35:155–160: Meth. Enzymol. 1985; 110:19–26 and references cited therein). A variety of these compounds are described and referenced below, however other HMG-CoA synthase inhibitors will be known to those skilled in the art. U.S. Pat. No. 5,120,729 (the disclosure of which is hereby incorporated by reference) discloses certain beta-lactam derivatives. U.S. Pat. No. 5,064,856 (the disclosure of which is hereby incorporated by reference) discloses certain spiro-lactone derivatives prepared by culturing a microorganism (MF5253). U.S. Pat. No. 4,847,271 (the disclosure of which is hereby incorporated by reference) discloses certain oxetane compounds such as 11-(3-hydroxymethyl-4-oxo-2-oxetayl)-3,5,7-trimethyl-2,4-undeca-dienoic acid derivatives.

Any compound that decreases HMG-CoA reductase gene expression may be used as the second compound in the combination aspect of this invention. These agents may be HMG-CoA reductase transcription inhibitors that block the transcription of DNA or translation inhibitors that prevent translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such regulation is readily determined by those skilled in the art according to standard assays (Meth. Enzymol. 1985; 110:9–19). Several compounds are described and referenced below, however other inhibitors of HMG-COA reductase gene expression will be known to those skilled in the art. U.S. Pat. No. 5,041,432 (the disclosure of which is incorporated by reference) discloses certain 15-substituted lanosterol derivatives. Other oxygenated sterols that suppress synthesis of HMG-CoA reductase are discussed by E. I. Mercer (Prog. Lip. Res. 1993;32:357–416).

Any squalene synthetase inhibitor may be used as the second compound of this invention. The term squalene synthetase inhibitor refers to compounds which inhibit the condensation of 2 molecules of famesylpyrophosphate to form squalene, catalyzed by the enzyme squalene synthetase. Such inhibition is readily determined by those skilled in the art according to standard assays (Meth. Enzymol. 1969; 15: 393–454 and Meth. Enzymol. 1985; 110:359–373 and references contained therein). A variety of these compounds are described in and referenced below however other squalene synthetase inhibitors will be known to those skilled in the art. U.S. Pat. No. 5,026,554 (the disclosure of which is incorporated by reference) discloses fermentation products of the microorganism MF5465 (ATCC 74011) including zaragozic acid. A summary of other patented squalene synthetase inhibitors has been compiled (Curr. Op. Ther. Patents (1993) 861–4).

Any squalene epoxidase inhibitor may be used as the second compound in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta 1984; 794:466–471). A variety of these compounds are described and referenced below, however other squalene epoxidase inhibitors will be known to those skilled in the art. U.S. Pat. Nos. 5,011,859 and 5,064,864 (the disclosures of which are incorporated by reference) disclose certain fluoro analogs of squalene. EP publication 395,768 A (the disclosure of which is incorporated by reference) discloses certain substituted allylamine derivatives. PCT publication WO 9312069 A (the disclosure of which is hereby incorporated by reference) discloses certain amino alcohol derivatives. U.S. Pat. No. 5,051,534 (the disclosure of which is hereby incorporated by reference) discloses certain cyclopropyloxy-squalene derivatives.

Any squalene cyclase inhibitor may be used as the second component in the combination aspect of this invention. The term squalene cyclase inhibitor refers to compounds which inhibit the bioconversion of squalene-2,3-epoxide to lanosterol, catalyzed by the enzyme squalene cyclase. Such inhibition is readily determined by those skilled in the art according to standard assays (FEBS Lett. 1989;244:347–350.). In addition, the compounds described and referenced below are squalene cyclase inhibitors, however other squalene cyclase inhibitors will also be known to those skilled in the art. PCT publication WO09410150 (the disclosure of which is hereby incorporated by reference) discloses certain 1,2,3,5,6,7,8,8α-octahydro-5,5,8α(beta)-trimethyl-6-isoquinolineamine derivatives, such as N-trifluoroacetyl-1,2,3,5,6,7,8,α-octahydro-2-allyl-5,5,8α (beta)-trimethyl-6(beta)-isoquinolineamine. French patent publication 2697250 (the disclosure of which is hereby incorporated by reference) discloses certain beta, beta-dimethyl-4-piperidine ethanol derivatives such as 1-(1,5,9-trimethyidecyl)-beta,beta-dimethyl-4-piperidineethanol.

Any combined squalene epoxidase/squalene cyclase inhibitor may be used as the second component in the combination aspect of this invention. The term combined qualene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 (the disclosures of which are incorporated by reference) disclose certain azadecalin derivatives. EP publication 468,434 (the disclosure of which is incorporated by reference) discloses certain piperidyl ether and thio-ether derivatives such as 2-(1-piperidyl) pentyl isopentyl sulfoxide and 2-(1-piperidyl)ethyl ethyl sulfide. PCT publication WO9401404 (the disclosure of which is hereby incorporated by reference) discloses certain acyl-piperidines such as 1-(1-oxopentyl-5-phenylthio)-4-(2-hydroxy-1-methyl)-ethyl)piperidine. U.S. Pat. No. 5,102,915 (the disclosure of which is hereby incorporated by reference) discloses certain cyclopropyloxy-squalene derivatives.

The starting materials and reagents for the above described Formula I compounds, are also readily available or can be easily synthesized by those skilled in the art using conventional methods of organic synthesis. For example, many of the compounds used herein, are related to, or are derived from compounds in which there is a large scientific interest and commercial need, and accordingly many such compounds are commercially available or are reported in the literature or are easily prepared from other commonly available substances by methods which are reported in the literature.

Some of the Formula I compounds of this invention or intermediates in their synthesis have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by, for example, chiral HPLC methods or converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. Also, an enantiomeric mixture of the Formula I compounds or an intermediate in their synthesis which contain an acidic or basic moiety may be separated into their corresponding pure enantiomers by forming a diastereomeric salt with an optically pure chiral base or acid (e.g., 1-phenyl-ethyl amine or tahtaric acid) and separating the diasteromers by fractional crystallization followed by neutralization to break the salt, thus providing the corresponding pure enantiomers. All such isomers, including diastereomers, enantiomers and mixtures thereof are considered as part of this invention. Also, some of the compounds of this invention are atropisomers (e.g., substituted biaryls) and are considered as part of this invention.

More specifically, the Formula I compounds of this invention may be obtained in enantiomerically enriched form by resolving the racemate of the final compound or an intermediate in its synthesis (preferably the final compound) employing chromatography (preferably high pressure liquid chromatography [HPLC]) on an asymmetric resin (preferably Chiralcel™ AD or OD [obtained from Chiral Technologies, Exton, Pa.]) with a mobile phase consisting of a hydrocarbon (preferably heptane or hexane) containing between 0 and 50% isopropanol (preferably between 2 and 20%) and between 0 and 5% of an alkyl amine (preferably 0.1% of diethylamine). Concentration of the product containing fractions affords the desired materials.

Some of the Formula I compounds of this invention are acidic and they form a salt with a pharmaceutically acceptable cation. Some of the Formula I compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds can be obtained in crystalline form by dissolution in an appropriate solvent(s) such as ethanol, hexanes or water/ethanol mixtures.

In addition, when the Formula I compounds of this invention form hydrates or solvates they are also within the scope of the invention.

The Formula I compounds of this invention, their prodrugs and the salts of such compounds and prodrugs are all adapted to therapeutic use as agents that inhibit cholesterol ester transfer protein activity in mammals, particularly humans. Thus, the compounds of this invention elevate plasma HDL cholesterol, its associated components, and the functions performed by them in mammals, particularly humans. By virtue of their activity, these agents also reduce plasma levels of triglycerides, LDL cholesterol, VLDL cholesterol and their associated components in mammals, particularly humans.

Hence, these compounds are useful for the treatment and correction of the various dyslipidemias observed to be associated with the development and incidence of atherosclerosis and cardiovascular disease, including hypoalphalipoproteinemia, hyperbetalipoproteinemia, hypertriglyceridemia, and familial-hypercholesterolemia.

Further, introduction of a functional CETP gene into an animal lacking CETP (mouse) results in reduced HDL levels (Agellon, L. B., et al: *J. Biol. Chem.* (1991) 266: 10796–10801.) increased susceptibility to atherosclerosis. (Marotti, K. R., et al: *Nature* (1993) 364: 73–75.). Also, inhibition of CETP activity with an inhibitory antibody raises HDL-cholesterol in hamster (Evans, G. F., et al: *J. of Lipid Research* (1994) 35: 1634–1645.) and rabbit (Whitlock, M. E., et al: *J. Clin. Invest* (1989) 84: 129–137). Suppression of increased plasma CETP by intravenous injection with antisense oligodeoxynucleotides against CETP mRNA reduced atherosclerosis in cholesterol-fed rabbits (Sugano, M., et al: *J. of Biol. Chem.* (1998) 273: 5033–5036.) Importantly, human subjects deficient in plasma CETP, due to a genetic mutation possess markedly elevated plasma HDL-cholesterol levels and apolipoprotein A-I, the major apoprotein component of HDL. In addition, most demonstrate markedly decreased plasma LDL cholesterol and apolipoprotein B (the major apolipoprotein component of LDL. (Inazu, A., et al.: *N. Engl. J. Med.* (1990) 323: 1234–1238.)

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the Formula I compounds of this invention, their prodrugs and the salts of such compounds and prodrugs, by virtue of their pharmacologic action, are useful for the prevention, arrestment and/or regression of atherosclerosis and its associated disease states. These include cardiovascular disorders (e.g., angina, cardiac ischemia and myocardial infarction), complications due to cardiovascular disease therapies (e.g., reperfusion injury and angioplastic restenosis), hypertension, stroke, and atherosclerosis associated with organ transplantation.

Because of the beneficial effects widely associated with elevated HDL levels, an agent which inhibits CETP activity in humans, by virtue of its HDL increasing ability, also provides valuable avenues for therapy in a number of other disease areas as well.

Thus, given the ability of the Formula I compounds of this invention, their prodrugs and the salts of such compounds and prodrugs to alter lipoprotein composition via inhibition of cholesterol ester transfer, they are of use in the treatment of vascular complications associated with diabetes. Hyperlipidemia is present in most Lu subjects with diabetes mellitus (Howard, B. V. 1987. J. Lipid Res. 28, 613). Even in the presence of normal lipid levels, diabetic subjects experience a greater risk of cardiovascular disease (Kannel, W. B. and McGee, D. L. 1979. Diabetes Care 2, 120). CETP-mediated cholesteryl ester transfer is known to be abnormally increased in both insulin-dependent (Bagdade, J. D., Subbaiah, P. V. and Ritter, M. C. 1991. Eur. J. Clin. Invest. 21, 161) and non-insulin dependent diabetes (Bagdade. J. D., Ritter, M. C., Lane, J. and Subbaiah. 1993. Atherosclerosis 104, 69). It has been suggested that the abnormal increase in cholesterol transfer results in changes in lipoprotein composition, particularly for VLDL and LDL, that are more atherogenic (Bagdade, J. D., Wagner, J. D., Rudel, L. L., and Clarkson, T. B. 1995. J. Lipid Res. 36, 759). These changes would not necessarily be observed during routine lipid screening. Thus the present invention will be useful in reducing the risk of vascular complications as a result of the diabetic condition.

The described agents are useful in the treatment of obesity. In both humans (Radeau, T., Lau, P., Robb, M., McDonnell, M., Ailhaud, G. and McPherson, R., 1995. *Journal of Lipid Research*. 36 (12):2552–61) and nonhuman primates (Quinet, E., Tall, A., Ramakrishnan, R. and Rudel, L., 1991. *Journal of Clinical Investigation*. 87 (5):1559–66) mRNA for CETP is expressed at high levels in adipose tissue. The adipose message increases with fat feeding (Martin, L. J., Connelly, P. W., Nancoo, D., Wood, N., Zhang, Z. J., Maguire, G., Quinet, E., Tall, A. R., Marcel, Y. L. and McPherson, R., 1993. *Journal of Lipid Research*. 34 (3):437–46), and is translated into functional transfer protein and through secretion contributes significantly to plasma CETP levels. In human adipocytes the bulk of cholesterol is provided by plasma LDL and HDL (Fong, B. S., and Angel, A., 1989. *Biochimica et Biophysica Acta* 1004 (1):53–60). The uptake of HDL cholesteryl ester is dependent in large part on CETP (Benoist, F., Lau, P., McDonnell, M., Doelle, H., Milne, R. and McPherson, R., 1997. *Journal of Biological Chemistry*. 272 (38):23572–7). This ability of CETP to stimulate HDL cholesteryl uptake, coupled with the enhanced binding of HDL to adipocytes in obese subjects (Jimenez, J. G., Fong, B., Julien, P., Despres, J. P., Rotstein, L., and Angel, A., 1989. *International Joumal of Obesity*. 13 (5):699–709), suggests a role for CETP, not only in generating the low HDL phenotype for these subjects, but in the development of obesity itself by promoting cholesterol accumulation. Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J., Johhston, A. R., and Weinstein, D. B., 1981. J. Clin. Invest. 67, 827–37). In vitro studies have demonstrated that binding of LPS to HDL substantially reduces the production and release of mediators of inflammation (Ulevitch, R. J., Johhston, A. R., 1978. J. Clin. Invest. 62, 1313–24). In vivo studies show that transgenic mice expressing human apo-AI and elevated HDL levels are protected from septic shock (Levine, D. M., Parker, T. S., Donnelly, T. M., Walsh, A. M., and Rubin, A. L. 1993. Proc. Natl. Acad. Sci. 90, 12040–44). Importantly, administration of reconstituted HDL to humans challenged with endotoxin resulted in a decreased inflammatory response (Pajkrt, D., Doran, J. E., Koster, F., Lerch, P. G., Amet, B., van der Poll, T., ten Cate, J. W., and van Deventer, S. J. H. 1996. J. Exp. Med. 184, 1601–08). The CETP inhibitors, by virtue of the fact that they raise HDL levels, attenuate the development of inflammation and septic shock.

The utility of the Formula I compounds of the invention, their prodrugs and the salts of such compounds and prodrugs as medical agents in the treatment of the above described disease/conditions in mammals (e.g. humans, male or female) is demonstrated by the activity of the compounds of this invention in conventional assays and the in vivo assay described below. The in vivo assay (with appropriate modifications within the skill in the art) may be used to determine the activity of other lipid or triglyceride controlling agents as well as the compounds of this invention. The combination protocol described below is useful for demonstrating the utility of the combinations of the lipid and triglyceride agents (e.g., the compounds of this invention) described herein. Such assays also provide a means whereby the activities of the Formula I compounds of this invention, their prodrugs and the salts of such compounds and prodrugs (or the other agents described herein) can be compared to each other and with the activities of other known compounds. The results of these comparisons are useful for determining dosage levels in mammals, including humans, for the treatment of such diseases.

The following protocols can of course be varied by those skilled in the art.

The hyperalphacholesterolemic activity of the Formula I compounds can be determined by assessing the effect of these compounds on the action of cholesteryl ester transfer protein by measuring the relative transfer ratio of radiolabeled lipids between lipoprotein fractions, essentially as previously described by Morton in J. Biol.

Chem. 256, 11992, 1981 and by Dias in Clin. Chem. 34, 2322, 1988.

CETP In Vitro Assay

The following is a brief description of the assay of cholesteryl ester transfer in human plasma (in vitro) and animal plasma (ex vivo): CETP activity in the presence or absence of drug is assayed by determining the transfer of $^3$H-labeled cholesteryl oleate (CO) from exogenous tracer HDL to the nonHDL lipoprotein fraction in human plasma, or from $^3$H-labeled LDL to the HDL fraction in transgenic mouse plasma. Labeled human lipoprotein substrates are prepared similarly to the method described by Morton in which the endogenous CETP activity in plasma is employed to transfer $^3$H-CO from phospholipid liposomes to all the lipoprotein fractions in plasma. $^3$H-labeled LDL and HDL are subsequently isolated by sequential ultracentrifugation at the density cuts of 1.019–1.063 and 1.10–1.21 g/ml, respectively. For the activity assay, $^3$H-labeled lipoprotein is added to plasma at 10–25 nmoles CO/ml and the samples incubated at 37° C. for 2.5–3 hrs. Non-HDL lipoproteins are then precipitated by the addition of an equal volume of 20% (wt/vol) polyethylene glycol 8000 (Dias). The samples are centrifuged 750 g×20 minutes and the radioactivity contained in the HDL containing supernatant determined by liquid scintillation. Introducing varying quantities of the compounds of this invention as a solution in dimethylsulfoxide to human plasma, before addition of the radiolabeled cholesteryl oleate, and comparing the relative amounts of radiolabel transferred allows relative cholesteryl ester transfer inhibitory activities to be determined.

CETP In Vivo Assay

Activity of these compounds in vivo can be determined by the amount of agent required to be administered, relative to control, to inhibit cholesteryl ester transfer activity by 50% at various time points ex vivo or to elevate HDL cholesterol by a given percentage in a CETP-containing animal species. Transgenic mice expressing both human CETP and human apolipoprotein AI (Charles River, Boston, Mass.) may be used to assess compounds in vivo. The compounds to be examined are administered by oral gavage in an emulsion vehicle containing olive oil and sodium taurocholate. Blood is taken from mice retroorbitally before dosing. At various times after dosing, ranging from 4 h to 24 h, the animals are sacrificed, blood obtained by heart puncture, and lipid parameters measured, including total cholesterol, HDL and LDL cholesterol, and triglycerides. CETP activity is determined by a method similar to that described above except that $^3$H-cholesteryl oleate containing LDL is used as the donor source as opposed to HDL. The values obtained for lipids and transfer activity are compared to those obtained prior to dosing and/or to those from mice receiving vehicle alone.

Plasma Lipids Assay

The activity of these compounds may also be demonstrated by determining the amount of agent required to alter plasma lipid levels, for example HDL cholesterol levels, LDL cholesterol levels, VLDL cholesterol levels, or triglycerides, in the plasma of certain mammals, for example marmosets that possess CETP activity and a plasma lipoprotein profile similar to that of humans (Crook et al. Arteriosclerosis 10, 625, 1990). Adult marmosets are assigned to treatment groups so that each group has a similar mean ±SD for total, HDL, and/or LDL plasma cholesterol concentrations. After group assignment, marmosets are dosed daily with compound as a dietary admix or by intragastric intubation for from one to eight days. Control marmosets receive only the dosing vehicle. Plasma total, LDL, VLDL, and HDL cholesterol values can be determined at any point during the study by obtaining blood from an antecubital vein and separating plasma lipoproteins into their individual subclasses by density gradient centrifugation, and by measuring cholesterol concentration as previously described (Crook et al. Arteriosclerosis 10, 625, 1990).

In Vivo Atherosclerosis Assay

Anti-atherosclerotic effects of the compounds can be determined by the amount of compound required to reduce the lipid deposition in rabbit aorta. Male New Zealand White rabbits are fed a diet containing 0.2% cholesterol and 10% coconut oil for 4 days (meal-fed once per day). Rabbits are bled from the marginal ear vein and total plasma cholesterol values are determined from these samples. The rabbits are then assigned to treatment groups so that each group has a similar mean ±SD for total plasma cholesterol concentration, HDL cholesterol concentration, triglyceride concentration and/or cholesteryl ester transfer protein activity. After group assignment, rabbits are dosed daily with compound given as a dietary admix or on a small piece of gelatin based confection. Control rabbits receive only the dosing vehicle, be it the food or the gelatin confection. The cholesterol/coconut oil diet is continued along with the compound administration throughout the study. Plasma cholesterol values and cholesteryl ester transfer protein activity can be determined at any point during the study by obtaining blood from the marginal ear vein. After 3–5 months, the rabbits are sacrificed and the aortae are removed from the thoracic arch to the branch of the iliac arteries. The aortae are cleaned of adventitia, opened longitudinally and then stained with Sudan IV as described by Holman et. al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the compound-receiving group in comparison with the control rabbits.

Antiobesity Protocol

The ability of CETP inhibitors to cause weight loss can be assessed in obese human subjects with body mass index (BMI)≧30 kg/m$^2$. Doses of inhibitor are administered sufficient to result in an increase of ≧25% in HDL cholesterol levels. BMI and body fat distribution, defined as waist (W) to hip (H) ratio (WHR), are monitored during the course of the 3–6 month studies, and the results for treatment groups compared to those receiving placebo.

In Vivo Sepsis Assay

In vivo studies show that transgenic mice expressing human apo-AI and elevated HDL levels are protected from septic shock. Thus the ability of CETP inhibitors to protect from septic shock can be demonstrated in transgenic mice expressing both human apo-AI and human CETP transgenes (Levine, D. M., Parker, T. S., Donnelly, T. M., Walsh, A. M. and Rubin, A. L., 1993. Proc. Natl. Acad. Sci. 90, 12040–44). LPS derived from *E. coli* is administered at 30 mg/kg by i.p. injection to animals which have been administered a CETP inhibitor at an appropriate dose to result in elevation of HDL. The number of surviving mice is determined at times up to 48 h after LPS injection and compared to those mice administered vehicle (minus CETP inhibitor) only.

Administration of the compounds of this invention can be via any method which delivers a compound of this invention systemically and/or locally. These methods include oral routes, parenteral, intraduodenal routes, etc. Generally, the compounds of this invention are administered orally, but parenteral administration (e. g., intravenous, intramuscular, subcutaneous or intramedullary) may be utilized, for example, where oral administration is inappropriate for the target or where the patient is unable to ingest the drug.

In general an amount of a compound of this invention is used that is sufficient to achieve the therapeutic effect desired (e. g., HDL elevation).

In general an effective dosage for the Formula I compounds of this invention, their prodrugs and the salts of such compounds and prodrugs is in the range of 0.01 to 10 mg/kg/day, preferably 0.1 to 5 mg/kg/day.

A dosage of the combination pharmaceutical agents to be used in conjuction with the CETP inhibitors is used that is effective for the indication being treated.

For example, typically an effective dosage for HMG-CoA reductase inhibitors is in the range of 0.01 to 100 mg/kg/day. In general an effect dosage for the MTP/Apo B secretion inhibitors is in the range of 0.01 to 100 mg/kg/day.

The compounds of the present invention are generally admhistered in the form of a pharmaceutical composition comprising at least one of the compounds of this invention together with a pharmaceutically acceptable vehicle, diluent or carrier. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. A preferred formulation is a solution or suspension in an oil, for example olive oil, Miglyol™ or Capmul™, in a soft gelatin capsule. Antioxidants may be added to prevent long term degradation as appropriate. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e. g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated, e. g., atherosclerosis.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e. g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e. g., in the form of numbers next to the tablets or capsules whereby the numbers correspond with the days of the regimen which the tablets or capsules so specified should be ingested. Another example of such a memory aid is a calendar printed on the card, e. g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of this invention either alone or in combination with each other or other compounds generally will be administered in a convenient formulation. The following formulation examples only are illustrative and are not intended to limit the scope of the present invention.

In the formulations which follow, "active ingredient" means a compound of this invention.

Formulation 1: Gelatin Capsules

Hard gelatin capsules are prepared using the following:

| Ingredient | Quantity (mg/capsule) |
| --- | --- |
| Active ingredient | 0.25–100 |
| Starch, NF | 0–650 |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredients, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |

-continued

| Ingredient | Quantity (mg/5 ml) |
| --- | --- |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume.

An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient dissolved in ethanol 1% | 20 mg |
| Intralipid ™ emulsion | 1,000 mL |

The solution of the above ingredients is intravenously administered to a patient at a rate of about 1 mL per minute.

Soft gelatin capsules are prepared using the following:

Formulation 8: Soft Gelatin Capsule with Oil Formulation

| Ingredient | Quantity (mg/capsule) |
| --- | --- |
| Active ingredient | 10–500 |
| Olive Oil or Miglyol ™ Oil | 500–1000 |

GENERAL EXPERIMENTAL PROCEDURES

NMR spectra were recorded on a Varian XL-300 (Varian Ca, Palo Alto, Calif.), a Bruker AM-300 spectrometer (Bruker Co., Billerica, Mass.) or a Varian Unity 400 at about 23° C. at 300 MHz for proton and 75.4 mHz for carbon nuclei. Chemical shifts are expressed in parts per million downfield from tetramethylsilane. The peak shapes are denoted as follows: s, singlet; d, doublet; t, triplet, q, quartet; m, multiplet; bs=broad singlet. Resonances designated as exchangeable did not appear in a separate NMR experiment where the sample was shaken with several drops of $D_2O$ in the same solvent. Atmospheric pressure chemical ionization (APCI) mass spectra were obtained on a Fisons Platform II Spectrometer. Chemical ionization mass spectra were obtained on a Hewlett-Packard 5989 instrument (Hewlett-Packard Co., Palo Alto, Calif.) (ammonia ionization, PBMS). Where the intensity of chlorine or bromine-containing ions are described, the expected intensity ratio was observed (approximately 3:1 for $^{35}Cl/^{37}Cl$-containing ions) and 1:1 for $^{79}Br/^{81}Br$-containing ions) and the intensity of only the lower mass ion is given.

Column chromatography was performed with either Baker Silica Gel (40 μm) (J. T. Baker, Phillipsburg, N.J.) or Silica Gel 60 (EM Sciences, Gibbstown, N.J.) in glass columns under low nitrogen pressure. Radial Chromatography was performed using a Chromatron (model 7924T, Harrison Research). Unless otherwise specified, reagents were used as obtained from commercial sources. Dimethylformamide, 2-propanol, tetrahydrofuran, and dichloromethane used as reaction solvents were the anhydrous grade supplied by Aldrich Chemical Company (Milwaukee, Wis.).

Microanalyses were performed by Schwarzkopf Microanalytical Laboratory, Woodside, N.Y. The terms "concentrated" and "evaporated" refer to removal of solvent at water aspirator pressure on a rotary evaporator with a bath temperature of less than 45° C. Reactions conducted at "0–20° C." or "0–25° C."were conducted with initial cooling of the vessel in an insulated ice bath which was allowed to warm to room temperature over several hours. The abbreviation "min" and "h" stand for "minutes" and "hours" respectively.

EXAMPLE 1

Example 1

6,7-Dimethoxy-2-methyl-4-oxo-3,4-dihydro-2H-quinoline-1-carboxylic acid benzyl ester 4,6,7-Trimethoxyquinoline (1.0 g, 4.6 mmol) was dissolved in anhydrous tetrahydrofuran (15 mL). The mixture was cooled to −78° C., and methyl magnesium chloride (2.3 mL of a 3.0M solution in tetrahydrofuran, 6.9 mmol) was added. The mixture was stirred at −78° C. for 1 h, then benzyl chloroformate (1.0 mL, 6.9 mmol) was added. The reaction was warmed to room temperature over 30 min, then 8 mL of a 1N aqueous HCl solution was added. After 30 minutes, the tetrahydrofuran was removed in vacuo, and the remaining aqueous phase was extracted with ethyl acetate (3×30 mL). The organic phases were combined and washed with water (15 mL), dried over sodium sulfate, filtered, and concentrated in vacuo to give 1.5 g of crude product. Purification by silica gel chromatography using 0–50% ethyl acetate/hexanes as eluent afforded 0.91 g of the desired product (57%). $^1H$ NMR (CDCl$_3$) δ 1.25 (d, 3H), 2.5 (d, 1H), 3.0 (dd, 1H), 3.7 (s, 3H), 3.9 (s, 3H), 5.1–5.3 (m, 5.2 (d, 1H), 5.4 (d, 1H), 7.3–7.5 (m, 7H).

Example 2A

4-Benzylimino-6,7-dimethoxy-2-methyl-3,4-dihydro-2H-quinoline-1-carboxylic acid benzyl ester 6,7-Dimethoxy-2-methyl-4-oxo-3,4-dihydro-2H-quinoline-1-carboxylic acid benzyl ester (0.83 g, 2.3 mmol) was dissolved in a solution of triethylamine (2.2 mL, 2.3 mmol), benzylamine (0.55 mL, 5.1 mmol), and anhydrous dichloromethane (15 mL). This solution was stirred in a room temperature water bath as 2.5 mL of 1M solution of titanium tetrachloride (TiCl$_4$) in dichloromethane (2.5 mmol) was slowly added. The reaction was allowed to stir at room temperature for 48 h. The reaction mixture was then poured into a stirred solution of water (50 mL) and potassium carbonate (10 g). After filtration, the filtrate was extracted with ethyl acetate (3×100 mL), the combined organic phases washed with water (100 mL), brine (50 mL), dried over sodium sulfate, filtered, and concentrated in vacuo to give the desired imine (1.12 g, ca. 100%). $^1H$ NMR (CDCl$_3$) δ 1.2 (d, 3H), 2.7–2.9 (m, 2H), 3.7 (s, 3H), 3.9 (s, 3H), 4.6 (d, 1H), 4.7 (d, 1H), 5.0–5.2 (m, 2H), 5.4 (d, 1H), 7.2–7.5 (m, 11H), 7.8 (s, 1H).

Example 2B cis-4-Benzylamino-6,7-dimethyoxy-2-methyl-3,4-dihydro-2H-quinoline-1-carboxylic acid benzyl ester 4-Benzylimino-6,7-dimethoxy-2-methyl-3,4-dihydro-2H-quinoline-1-carboxylic acid benzyl ester (1.02 g, 2.29 mmol) was dissolved in ethanol (12 mL), and sodium borohydride (96 mg, 2.5 mmol) was added. After the reaction was stirred overnight, additional sodium borohydride (43 mg, 1.1 mmol) was added, and the reaction was stirred for 20 min. The reaction mixture was then concentrated in vacuo to about 8 mL and then neutralized with 1N HCl. The mixture was extracted with ethyl acetate (3×12 mL). The organic phases were combined and washed with water (10 mL), brine (5 mL), dried over sodium sulfate, filtered, and concentrated in vacuo to give 1.07 g of a crude mixture of product amines. Purification by silica gel chromatography using 0–20% ethyl acetate/hexanes as eluent afforded the cis amine (160 mg, 16%). $^1H$ NMR (CDCl$_3$) δ 1.1–1.3 (m, 4H), 2.6 (ddd, 1H), 3.5 (dd, 1H), 3.7 (s, 3H), 3.9 (s, 3H), 3.9 (d, 1H), 4.1 (d, 1H), 4.4–4.6 (m, 1H), 5.0 (d, 1H), 5.3 (d, 1H), 6.9 (s, 1H), 7.1 (s, 1H), 7.2–7.5 (m, 10H). Continued elutions using increasing concentrations of ethyl acetate provide the trans amine.

Example 3A

4-Hydroxyimino-6,7-dimethoxy-2-methyl-3,4-dihydro-2H-quinoline-1-carboxylic acid ethyl ester A stirred solution of 6,7-dimethoxy-2-methyl-4-oxo-3,4-dihydro-2H-quinoline-1-carboxylic acid ethyl ester (10.0 g, 34.1 mmol), hydroxylamine hydrochloride (7.1 g, 102 mmol), and sodium acetate (7.0 g, 85 mmol) in ethanol (50 mL) was heated at reflux for 2 h. Water (50 mL) was added, and the volatiles were removed in vacuo. Ethyl acetate (175 mL) was added, and the mixture was stirred vigorously for The active ingredient above may also be a combination of agents.

10 min. The aqueous phase was separated and extracted with ethyl acetate (2×60 mL). The combined organic layers were washed with brine (25 mL), dried over magnesium sulfate, filtered and concentrated in vacuo to give the title compound as a white foam (12.28 g, ca. 100%). $^1$H NMR (CDCl$_3$) δ 1.1 (d, 3H), 1.32 (t, 3H), 2.77 (dd, 1H), 3.07 (dd, 1H), 3.89 (s, 6H), 4.2–4.4 (m, 2H), 5.0 (m, 1H), 7.18 (s, 1H), 7.26 (s, 1H).

Example 3B cis-4-Amino-6,7-dimethoxy-2-methyl-3,4-dihydro-2H-quinoline-1-carboxylic acid ethyl ester To a stirred solution of 4-hydroxyimino-6,7-dimethoxy-2-methyl-3,4-dihydro-2H-quinoline-1-carboxylic acid ethyl ester (11.0 g, 34.1 mmol) in ethanol (100 mL) and aqueous 2N KOH (102 mL, 205 mmol) was added aluminum-nickel alloy (11.7 g, 136 mmol) in portions over 15 min. The reaction was stirred for 35 min, then filtered through a pad of Celite®, rinsing with ethanol. The volatiles were removed in vacuo, and the resulting aqueous phase was extracted with ethyl acetate (3×150 mL). The combined organic phases were washed with brine, dried over sodium sulfate, filtered, and concentrated in vacuo to give 16.32 g of crude product. Purification by silica gel chromatography using 0–4% methanol in dichloromethane as eluent afforded the title compound (6.51 g, 65%): $^1$H NMR (CDCl$_3$) δ 1.19 (d, 3H, J=6 Hz), 1.25 (m, 1H), 1.28 (t, 3H, J=7 Hz), 2.4 (m, 1H), 3.76 (m, 1H), 3.86 (s, 3H), 3.90 (s, 3H), 4.10–4.35 (m, 2H), 4.5 (m, 1H), 6.96 (s, 1H), 7.0 (s, 1H).

Example 3C cis-4-[(3,5-Bis-trifluoromethyl-benzyl)-amino]-6,7-dimethoxy-2-methyl-3,4-dihydro-2H-quinoline-1-carboxylic acid ethyl ester A solution of cis-4-amino-6,7-dimethoxy-2-methyl-3,4-dihydro-2H-quinoline-1-carboxylic acid ethyl ester (527 mg, 1.8 mmol) in dichloroethane (12 mL) was treated sequentially with acetic acid (0.1 mL, 1.8 mmol) and 3,5-bis-trifluoromethyl-benzaldehyde (0.30 mL, 1.8 mmol). After stirring 35 minutes at room temperature, sodium triacetoxyborohydride (570 mg, 2.7 mmol) was added to the mixture. After 3 days, 20 mL of water was added and the mixture made basic (pH 10) with potassium carbonate. The mixture was extracted with ethyl acetate (3×35 mL), the combined organic layers were washed with brine (20 mL), dried over sodium sulfate, filtered, and concentrated in vacuo. The residue was purified by silica gel chromatography eluting with 0–20% ethyl acetate in hexanes to provide the title compound (663 mg). $^1$H NMR (CDCl$_3$) δ 1.22 (d, 3H), 1.3 (t, 3H), 1.5 (m, 1H), 2.6 (m, 1H), 3.55 (dd, 1H), 3.87 (s, 3H), 3.89 (s, 3H), 4.1–4.6 (m, 5H), 7.06 (s, 1H), 7.08 (s, 1H), 7.8 (s, 1H), 7.95 (s, 2H).

Example 4 cis-4-(Benzyl-ethoxycarbonyl-amino)-6,7-dimethoxy-2-methyl-3,4-dihydro-2H-quinoline-1-carboxylic acid benzyl ester To a solution of cis-4-benzylamino-6,7-dimethyoxy-2-methyl-3,4-dihydro-2H-quinoline-1-carboxylic acid benzyl ester (Example 2B) (150 mg, 0.34 mmol) in anhydrous dichloromethane (5 mL) were added pyridine (0.20 mL, 2.3 mmol) and ethyl chloroformate (0.16 mL, 1.7 mmol). The reaction was stirred at room temperature overnight. The reaction mixture was then poured into water (20 mL), and aqueous 2N KOH (10 mL) was added. The solution was stirred for 30 min, then the mixture was extracted with ether (3×25 mL). The organic phases were combined and washed with 1N HCl (3×10 mL) and then a saturated sodium bicarbonate solution (10 mL). The organic layer was dried over sodium sulfate, filtered and concentrated in vacuo to give 190 mg of crude product. Purification by silica gel chromatography using 0–40% ethyl acetate/hexanes as eluent afforded the desired final product (146 mg, 83%): MS m/z 519 (M$^+$+1), 537 (M$^+$+19), 340 (M$^+$–178); $^1$H NMR (CDCl$_3$) δ 6.99 (C8, s, 1H), 6.42 (C5, s, 1H).

Using the appropriate starting materials, Examples 5–10, 49, 63 and 65 were prepared in an analogous manner to the sequence of reactions described for Examples 1, 2A, 2B and 4, and Examples 11–48, 50–62 and 64 were prepared in an analogous manner to the sequence of reactions described for Examples 1, 3A, 3B, 3C and 4.

Example 5 cis-4-(Benzyl-isobutoxycarbonyl-amino)-6,7-dimethoxy-2-methyl-3,4-dihydro-2H-quinoline-1-carboxylic acid ethyl ester MS m/z 484 (M$^+$), 502 (M$^+$+18); $^1$H NMR (CDCl$_3$) δ 6.45 (C5, s, 1H), 1.19 (C2-Me, d, 3H, J=6.2 Hz).

Example 6 cis-4-(Benzyl-methoxycarbonyl-amino)-6,7-dimethoxy-2-methyl-3,4-dihydro-2H-quinoline-1-carboxylic acid ethyl ester MS m/z 443 (M$^+$+1), 460 (M$^+$+18); $^1$H NMR (CDCl$_3$) δ 7.10 (C8, s, 1H), 1.19 (C2-Me, d, 3H, J=6.2 Hz).

Example 7 cis-4-(Benzyl-isopropoxycarbonyl-amino)-6,7-dimethoxy-2-methyl-3,4-dihydro-2H-quinoline-1-carboxylic acid ethyl ester MS m/z 470 (M$^+$), 488 (M$^+$+18); $^1$H NMR (CDCl$_3$) δ 6.41 (C5, s, 1H), 1.14 (C2-Me, d, 3H, J=6.2 Hz).

Example 8 cis-4-(Benzyl-hexyloxycarbonyl-amino)-6,7-dimethoxy-2-methyl-3,4-dihydro-2H-quinoline-1-carboxylic acid ethyl ester MS m/z 512 (M$^+$); $^1$H NMR (CDCl$_3$) δ 6.41 (C5, s, 1H), 1.14 (C2-Me, d, 3H).

Example 9 cis-4-(Benzyl-butoxycarbonyl-amino)-6,7-dimethoxy-2-methyl-3,4-dihydro-2H-quinoline-1-carboxylic acid ethyl ester MS m/z 484 (M$^+$), 502 (M$^+$+18); $^1$H NMR (CDCl$_3$) δ 7.04 (C8, s, 1H), 1.41 (C2-Me, d, 3H, J=6.20 Hz).

Example 10 cis-4-(Benzyl-benzyloxycarbonyl-amino)-6,7-dimethoxy-2-methyl-3,4-dihydro-2H-quinoline-1-carboxylic acid ethyl ester MS m/z 520 (M$^+$+2), 537 (M$^+$+19); $^1$H NMR (CDCl$_3$) δ 7.28–7.11 (m, 10H), 6.33 (C5, s, 1H).

Example 11 cis-6,7-Dimethoxy-4-(methoxycarbonyl-naphthalen-2-ylmethyl-amino)-2-methy-3,4-dihydro-2H-quinoline-1-carboxylic acid ethyl ester MS m/z 493 ($M^+$+1), 510 ($M^+$+18); $^1$H NMR (CDCl$_3$) δ 7.05 (C8, s, 1H), 6.43 (C5, s, 1H), 2.34–2.28 (m, 1H).

Example 12 cis-4-[(4-Chloro-benzyl)-methoxycarbonyl-amino]-6,7-dimethoxy-2-methyl-3,4-dihydro-2H-quinoline-1-carboxylic acid ethyl ester MS m/z 477 ($M^+$+1), 494 ($M^+$+17); $^1$H NMR (CDCl$_3$) δ 6.44 (C5, s, 1H), 2.29–2.18 (m, 1H).

Example 13 cis-6,7-Dimethoxy-4-[(4-methoxy-benzyl)-methoxycarbonyl-amino]-2-methyl-3,4-dihydro-2H-quinoline-1-carboxylic acid ethyl ester MS m/z 473 ($M^+$+1), 490 ($M^+$+18); $^1$H NMR (CDCl$_3$) δ 6.41 (C5, s, 1H), 3.75–3.70 (bs, 12H).

Example 14 cis-6,7-Dimethoxy-4-(methoxycarbonyl-thiophen-2-ylmethyl-amino)-2-methyl-3,4-dihydro-2H-quinoline-1-carboxylic acid ethyl ester MS m/z 449 ($M^+$+1), 466 ($M^+$+18); $^1$H NMR (CDCl$_3$) δ 6.34 (C5, s, 1H), 3.84 (s, 6H).

Example 15 cis-6,7-Dimethoxy-4-[methoxycarbonyl-(4-methyl-benzyl)-amino]-2-methyl-3,4-dihydro-2H-quinoline-1-carboxylic acid ethyl ester MS 457 ($M^+$+1), 474 ($M^+$+18); $^1$H NMR (CDCl$_3$) δ 6.45 (C5, s, 1H), 2.29 (s, 3H).

Example 16 cis-4-[(3,5-Bis-trifluoromethyl-benzyl)-methoxycarbonyl-amino]-6,7-dimethoxy-2-methyl-3,4-dihydro-2H-quinoline-1-carboxylic acid ethyl ester MS m/z 596 ($M^+$+18); $^1$H NMR (CDCl$_3$) δ 7.09 (C8, s, 1H), 6.39 (C5, s, 1H), 3.81 (s, 6H).

Example 17 cis-6,7-Dimethoxy-4-[methoxycarbonyl-(3-trifluoromethyl-benzyl)-amino]-2-methyl-3,4-dihydro-2H-quinoline-1-carboxylic acid ethyl ester MS m/z 572 ($M^+$+2), 539 ($M^+$+19); $^1$H NMR (CDCl$_3$) δ 7.07 (s, 1H), 6.40 (s, 1H), 3.78 (s, 6H).

Example 18 cis-6,7-Dimethoxy-4-[methoxycarbonyl-(2-trifluoromethyl-benzyl)-amino]-2-methyl-3,4-dihydro-2H-quinoline-1-carboxylic acid ethyl ester MS m/z 511 ($M^+$+1), 528 ($M^+$+18); $^1$H NMR (CDCl$_3$) δ 7.06 (C8, s, 1H), 6.46 (C5, s, 1H).

Example 19 cis-6,7-Dimethoxy-4-[methoxycarbonyl-(4-trifluoromethyl-benzyl)-amino]-2-methyl-3,4-dihydro-2H-quinoline-1-carboxylic acid ethyl ester MS m/z 511 ($M^+$+1), 528 ($M^+$+18); $^1$H NMR (CDCl$_3$) δ 7.06 (C8, s, 1H), 6.40 (C5, s, 1H).

Example 20 cis-6,7-Dimethoxy-4-[methoxycarbonyl-(3-nitro-5-trifluoromethyl-benzyl)-amino]-2-methyl-3,4-dihydro-2H-quinoline-1-carboxylic acid ethyl ester MS m/z 556 ($M^+$+1), 573 ($M^+$+18); $^1$H NMR (CDCl$_3$) δ 6.39 (s, 1H), 7.10 (s, 1H), 7.85 (s, 1H), 8.32 (s, 1H), 8.40 (s, 1H).

Example 21 cis-6,7-Dimethoxy-4-[methoxycarbonyl-(3-nitro-benzyl)-amino]-2-methyl-3,4-dihydro-2H-quinoline-1-carboxylic acid ethyl ester MS m/z 488 ($M^+$+1), 505 ($M^+$+18); $^1$H NMR (CDCl$_3$) δ 6.42 (s, 1H), 7.09 (s, 1H), 7.5–7.7 (m, 2H), 8.2–8.3 (m, 2H).

Example 22 cis-6,7-Dimethoxy-4-[methoxycarbonyl-(3-phenyl-propyl)-amino]-2-methyl-3,4-dihydro-2H-quinoline-1-carboxylic acid ethyl ester MS m/z 470 ($M^+$), 488 ($M^+$+18); $^1$H NMR (CDCl$_3$) δ 6.36 (C8, s, 1H), 1.21 (C2-Me, d, 3H).

Example 23 cis-6,7-Dimethoxy-4-(methoxycarbonyl-phenethyl-amino)-2-methyl-3,4-dihydro-2H-quinoline-1-carboxylicacid ethyl ester MS m/z 456 ($M^+$), 474 ($M^+$+18); $^1$H NMR (CDCl$_3$) δ 6.36 (C5, s, 1H).

Example 24 cis-6,7-Dimethoxy-4-(methoxycarbonyl-pyridin-2-ylmethyl-amino)-2-methyl-3,4-dihydro-2H-quinoline-1-carboxylic acid ethyl ester MS m/z 444 ($M^+$+1); $^1$H NMR (CDCl$_3$) δ 6.51 (C5, s, 1H), 1.13 (C2-Me, d, 3H).

Example 25 cis-6,7-Dimethoxy-4-(methoxycarbonyl-pyridin-3-ylmethyl-amino)-2-methyl-3,4-dihydro-2H-quinoline-1-carboxylicacid ethyl ester MS m/z 444 ($M^+$+1); $^1$H NMR (CDCl$_3$) δ 7.03 (C8, s, 1H), 6.39 (C5, s, 1H).

Example 26 cis-4-[(3-Cyano-benzyl)-methoxycarbonyl-amino]-6,7-dimethoxy-2-methyl-3,4-dihydro-2H-quinoline-1-carboxylic acid ethyl ester 468 ($M^+$+1), 484 ($M^+$+17) $^1$H NMR (CDCl$_3$) δ 7.09 (C8, s, 1H), 6.39 (C5, s, 1H).

Example 27 cis-4-[(3-Chloro-benzyl)-methoxycarbonyl-amino]-6,7-dimethoxy-2-methyl-3,4-dihydro-2H-quinoline-1-carboxylic acid ethyl ester MS m/z 477 ($M^+$), 494 ($M^++19$); $^1$H NMR (CDCl$_3$) δ 6.40 (C5, s, 1H), 1.17 (C2-Me, d, 3H).

Example 28 cis-4-[(3,5-Difluoro-benzyl)-methoxycarbonyl-amino]-6,7-dimethoxy-2-methyl-3,4-dihydro-2H-quinoline-1-carboxylic acid ethyl ester MS m/z 479 ($M^++1$), 496 ($M^++18$); $^1$H NMR (CDCl$_3$) δ 6.39 (C5, s, 1H), 1.16 (C2-Me, d, 3H).

Example 29 cis-6,7-Dimethoxy-4-(methoxycarbonyl-pyridin-4-ylmethyl-amino)-2-methyl-3,4-dihydro-2H-quinoline-1-carboxylic acid ethyl ester MS m/z 444 ($M^++1$); $^1$H NMR (CDCl$_3$) δ 6.40 (C5, s, 1H), 1.17 (C2-Me, d, 3H).

Example 30 cis-4-[(3,5-Dichloro-benzyl)-methoxycarbonyl-amino]-6,7-dimethoxy-2-methyl-3,4-dihydro-2H-quinoline-1-carboxylic acid ethyl ester MS m/z 511 ($M^+$), 528 ($M^{++17}$); $^1$H NMR (CDCl$_3$) δ 6.39 (C5, s, 1H), 1.17 (C2-Me, d, 3H).

Example 31 cis-4-[(3,5-Bis-trifluoromethyl-benzyl)-ethoxycarbonyl-amino]-2-methyl-6-phenoxy-3,4-dihydro-2H-quinoline-1-carboxylic acid ethyl ester MS m/z 625 ($M^++1$); $^1$H NMR (CDCl$_3$) δ 5.26–5.44 (br., 1H), 6.56 (s, 1H).

Example 32 cis-4-[(3-Carboxy-benzyl)-methoxycarbonyl-amino]-6,7-dimethoxy-2-methyl-3,4-dihydro-2H-quinoline-1-carboxylic acid ethyl ester MS m/z 487 ($M^++1$), 504 ($M^++18$); $^1$H NMR (CDCl$_3$) δ 6.47 (C5, s, 1H), 1.18 (C2-Me, d, 3H, J=6.2 Hz).

Example 33 cis-4-[(2-Chloro-5-methanesulfinyl-benzyl)-methoxycarbonyl-amino]-6,7-dimethoxy-2-methyl-3,4-dihydro-2H-quinoline-1-carboxylic acid ethyl ester $^1$H NMR (CDCl$_3$) δ 6.49 (s, 1H), 7.1 (s, 1H).

Example 34 cis-6,7-Dimethoxy-4-[methoxycarbonyl-(2-nitro-benzyl)-amino]-2-methyl-3,4-dihydro-2H-quinoline-1-carboxylic acid ethyl ester MS m/z 488 ($M^++1$), 505 ($M^++18$); $^1$H NMR (CDCl$_3$) δ 6.47 (s, 1H), 3.85 (s, 6H).

Example 35 cis-4-[(2,4-Dinitro-benzyl)-methoxycarbonyl-amino]-6,7-dimethoxy-2-methyl-3,4-dihydro-2H-quinoline-1-carboxylic acid ethyl ester MS m/z 533 ($M^++1$), 550 ($M^++18$); $^1$H NMR (CDCl$_3$) δ 8.95 (s, 1H), 6.43 (C5, s, 1H), 3.87 (s, 6H).

Example 36 cis-4-[(3,5-Dinitro-benzyl)-methoxycarbonyl-amino]-6,7-dimethoxy-2-methyl-3,4-dihydro-2H-quinoline-1-carboxylic acid ethyl ester MS m/z 533 ($M^++1$), 550 ($M^++18$); $^1$H NMR (CDCl$_3$) δ 8.43 (s, 2H), 6.38 (C5, s, 1H), 3.84–3.82 (2s, 9H).

Example 37 cis-4-[(3-Dimethylsulfamoyl-5-trifluoromethyl-benzyl)-methoxycarbonyl-amino]-6,7-dimethoxy-2-methyl-3,4-dihydro-2H-quinoline-1-carboxylic acid ethyl ester MS m/z 617 ($M^+$), 635 ($M^++18$); $^1$H NMR (CDCl$_3$) δ 6.25 (C5, s, 1H), 3.84 (s, 3H), 3.77 (s, 6H), 2.69 (s, 6H).

Example 38 cis-4-[(2-Chloro-benzyl)-methoxycarbonyl-amino]-6,7-dimethoxy-2-methyl-3,4-dihydro-2H-quinoline-1-carboxylic acid ethyl ester MS m/z 477 ($M^+$), 494 ($M^++17$); $^1$H NMR (CDCl$_3$) δ 6.49 (C5, s, 1H), 1.14 (C2-Me, d, 3H, J=6.2 Hz).

Example 39 cis-6,7-Dimethoxy-4-[methoxycarbonyl-(4-nitro-benzyl)-amino]-2-methyl-3,4-dihydro-2H-quinoline-1-carboxylic acid ethyl ester MS m/z 488 ($M^++1$), 505 ($M^++18$); $^1$H NMR (CDCl$_3$) δ 6.39 (C5, s, 1H), 3.84 (s, 3H), 3.80–3.77 (2s, 6H).

Example 40 cis-6,7-Dimethoxy-4-[methoxycarbonyl-(3-sulfamoyl-5-trifluoromethyl-benzyl)-amino]-2-methyl-3,4-dihydro-2H-quinoline-1-carboxylic acid ethyl ester MS m/z 607 ($M^++18$); $^1$H NMR (CDCl$_3$) δ 8.12 (s, 2H), 6.38 (C5, s, 1H), 3.85 (s, 3H), 3.78 (s, 3H).

Example 41 cis-4-[(2,6-Dichloro-pyridin-4-ylmethyl)-methoxycarbonyl-amino]-6,7-dimethoxy-2-methyl-3,4-dihydro-2H-quinoline-1carboxylic acid ethyl ester MS m/z 512 ($M^+$), 278 ($M^+-233$); $^1$H NMR (CDCl$_3$) δ 6.33 (C5, s, 1H), 1.19 (C2-Me, d, 3H, J=6.2 Hz).

Example 42 cis-6,7-Dimethoxy-4-[methoxycarbonyl-(3-methoxycarbonyl-benzyl)-amino]-2-methyl-3,4-dihydro-2H-quinoline-1-carboxylic acid ethyl ester MS m/z 501 ($M^++1$), 518 ($M^++18$); $^1$H NMR (CDCl$_3$) δ 1.14 (d, 3H, J=6.2 Hz), 1.29 (t, 3H, J=7.4 Hz), 3.81 (s, 6H), 3.86 (s, 3H), 3.91 (s, 3H), 6.42 (s, 1H), 7.06 (s, 1H), 7.4–7.5 (m, 2H), 7.9–8.0 (m, 2H).

Example 43 cis-6,7-Dimethoxy-4-{methoxycarbonyl-[3-(4-methyl-piperazine-1-sulfonyl)-5-trifluoromethyl-benzyl]-amino}-2-methyl-3,4-dihydro-2H-quinoline-1-carboxylic acid ethyl ester MS m/z 533 ($M^++1$), 550 ($M^++18$); $^1$H NMR (CDCl$_3$) δ 8.95 (s, 1H), 6.43 (C5, s, 1H), 3.87 (s, 6H).

Example 44 cis-4-[(3,5-Bis-trifluoromethyl-benzyl)-ethoxycarbonyl-amino]-6,7-dimethoxy-2-methyl-3,4-dihydro-2H-quinoline-1-carboxylic acid ethyl ester MS m/z 593 (M$^+$+1), 611 (M$^+$+18); $^1$H NMR (CDCl$_3$) δ 7.08 (C8, s, 1H), 6.39 (C5, s, 1H), 1.31–1.22 (m, 6H).

Example 45 cis-4-[(3,5-Bis-trifluoromethyl-benzyl)-butoxycarbonyl-amino]-6,7-dimethoxy-2-methyl-3,4-dihydro-2H-quinoline-1-carboxylic acid ethyl ester MS m/z 621 (M$^+$+1); $^1$H NMR (CDCl$_3$) δ 6.38 (C5, s, 1H), 3.84 (s, 3H).

Example 46 cis-4-[(3,5-Bis-trifluoromethyl-benzyl)-hexyloxycarbonyl-amino]-6,7-dimethoxy-2-methyl-3,4-dihydro-2H-quinoline-1-carboxylic acid ethyl ester MS m/z 649 (M$^+$+1), 666 (M$^+$+18); $^1$H NMR (CDCl$_3$) δ 6.38 (C5, s, 1H), 3.84 (s, 3H).

Example 47 cis-4-[(3,5-Bis-trifluoromethyl-benzyl)-methoxycarbonyl-amino]-6-methoxy-2-methyl-3,4-dihydro-2H-quinoline-1-carboxylic acid ethyl ester MS m/z 549 (M$^+$+1), 566 (M$^+$18); $^1$H NMR (CDCl$_3$) δ 6.50 (C5, s, 1H), 1.14 (C2-Me, d, 3H, J=6.1 Hz).

Example 48 cis-4-[(3,5-Bis-trifluoromethyl-benzyl)-methoxycarbonyl-amino]-7-methoxy-2-methyl-3,4-dihydro-2H-quinoline-1-carboxylicacid ethyl ester MS m/z 566 (M$^+$+1); $^1$H NMR (CDCl$_3$) δ 7.76–7.64 (m, 3H), 3.78 (s, 6H).

Example 49 cis-4-[(3,5-Bis-trifluoromethyl-benzyl)-methoxycarbonyl-amino]-6,7-dimethoxy-2-methyl-3,4-dihydro-2H-quinoline-1-carboxylic acid benzyl ester MS m/z 641 (M$^+$+1), 658 (M$^+$+18); $^1$H NMR (CDCl$_3$) δ 6.38 (s, 1H), 7.0 (s, 1H), 7.7 (s, 2H), 7.8 (s, 1H).

Example 50 cis-4-[(3,5-Bis-trifluoromethyl-benzyl)-methoxycarbonyl-amino]-5,7-dimethoxy-2-methyl-3,4-dihydro-2H-quinoline-1-carboxylic acid ethyl ester MS m/z 579 (M$^+$+1), 597 (M$^+$+18); $^1$H NMR (CDCl$_3$) δ 7.63 (s, 1H), 3.78 (s, 3H).

Example 51 cis-4-[(3,5-Bis-trifluoromethyl-benzyl)-isopropoxycarbonyl-amino]-6,7-dimethoxy-2-methyl-3,4-dihydro-2H-quinoline-1-carboxylic acid ethyl ester MS m/z 607 (M$^+$+1), 624 (M$^+$+18); $^1$H NMR (CDCl$_3$) δ 6.41 (s, 1H), 3.86 (s, 3H), 3.79 (s, 3H).

Example 52 cis-4-[(3,5-Bis-trifluoromethyl-benzyl)-propoxycarbonyl-amino]-6,7-dimethoxy-2-methyl-3,4-dihydro-2H-quinoline-1-carboxylic acid ethyl ester MS m/z 606 (M$^+$), 624 (M$^+$+18); $^1$H NMR (CDCl$_3$) δ 6.39 (C5, s, 1H), 3.86 (s, 3H).

Example 53 cis-4-[(3,5-Bis-trifluoromethyl-benzyl)-tert-butoxycarbonyl-amino]-6,7-dimethoxy-2-methyl-3,4-dihydro-2H-quinoline-1-carboxylic acid ethyl ester MS m/z 639 (M$^+$+19); $^1$H NMR (CDCl$_3$) δ 6.47 (C5, s, 1H), 3.86–3.79 (m, 6H).

Example 54 cis-4-[(3,5-Bis-trifluoromethyl-benzyl)-isobutoxycarbonyl-amino]-6,7-dimethoxy-2-methyl-3,4-dihydro-2H-quinoline-1-carboxylic acid ethyl ester MS m/z 622 (M$^+$+1), 639 (M$^+$+19); $^1$H NMR (CDCl$_3$) δ 6.40 (C5, s, 1H), 3.88 (s, 3H), 3.79 (s, 3H).

Example 55 cis-4-[(3,5-Bis-trifluoromethyl-benzyl)-propoxycarbonyl-amino]-6,7-dimethoxy-2-methyl-3,4-dihydro-2H-quinoline-1-carboxylic acid propyl ester MS m/z 621 (M$^+$+1), 639 (M$^+$+19); $^1$H NMR (CDCl$_3$) δ 7.08 (C8, s, 1H), 6.40 (C5, s, 1H), 1.18 (C2-Me, d, 3H).

Example 56 cis-4-[(3,5-Bis-trifluoromethyl-benzyl)-methoxycarbonyl-amino]-6,7-dimethoxy-2-methyl-3,4-dihydro-2H-quinoline-1-carboxylic acid propyl ester MS m/z 593 (M$^+$+1), 611 (M$^+$+19); $^1$H NMR (CDCl$_3$) δ 7.08 (C8, s, 1H), 6.38 (C5, s, 1H), 1.17 (C2-Me, d 3H).

Example 57 cis-4-[(3,5-Dichloro-benzyl)-ethoxycarbonyl-amino]-6,7-dimethoxy-2-methyl-3,4-dihydro-2H-quinoline-1-carboxylic acid ethyl ester MS m/z 525 (M$^+$), 542 (M$^+$+17); $^1$H NMR (CDCl$_3$) δ 6.34 (s, 1H), 3.81 (s, 3H), 3.80 (s, 3H).

Example 58 cis-4-[(3-Chloro-5-trifluoromethyl-benzyl)-ethoxycarbonyl-amino]-6,7-dimethoxy-2-methyl-3,4-dihydro-2H-quinoline-1-carboxylic acid ethyl ester MS m/z 533 (M$^+$+1), 550 (M$^+$+18); $^1$H NMR (CDCl$_3$) δ 6.38 (C5, s, 1H), 3.86 (s, 2H), 3.80 (s, 3H).

Example 59 cis-4-[(3-Chloro-5-trifluoromethyl-benzyl)-methoxycarbonyl-amino]-6,7-dimethoxy-2-methyl-3,4-dihydro-2H-quinoline-1-carboxylic acid ethyl ester MS m/z 545 (M$^+$+1), 562 (M$^+$+18); $^1$H NMR (CDCl$_3$) δ 6.26 (s, 1H), 3.84 (s, 3H).

Example 60 cis-4-[Ethoxycarbonyl-(3-fluoro-5-trifluoromethyl-benzyl)-amino]-6,7-dimethoxy-2-methyl-3,4-dihydro-2H-quinoline-1-carboxylic acid ethyl ester MS m/z 543 ($M^+$+1), 560 ($M^+$+18); $^1$H NMR (CDCl$_3$) δ 6.38 (C5, s, 1H), 1.17 (C2-Me, d, 3H, J=6.2 Hz).

Example 61 cis-4-[(3-Fluoro-5-trifluoromethyl-benzyl)-methoxycarbonyl-amino]-6,7-dimethoxy-2-methyl-3,4-dihydro-2H-quinoline-1-carboxylic acid ethyl ester MS m/z 529 ($M^+$+1), 546 ($M^+$+18); $^1$H NMR (CDCl$_3$) δ 6.38 (C5, s, 1H), 1.17 (C2-Me, d, 3H, J=6.1 Hz).

Example 62 cis-4-[(3,5-Dimethyl-benzyl)-methoxycarbonyl-amino]-6,7-dimethoxy-2-methyl-3,4-dihydro-2H-quinoline-1-carboxylic acid ethyl ester $^1$H NMR (CDCl$_3$) δ 1.2 (d, 3H), 2.3 (s, 6H), 3.7 (s, 6H), 3.8 (s, 3H), 6.4 (s, 1H), 6.8 (s, 3H), 7.1 (s, 1H).

Example 63 cis-4-[(3,5-Bis-trifluoromethyl-benzyl)-methoxycarbonyl-amino]-2-methyl-6-trifluoromethoxy-3,4-dihydro-2H-quinoline-1-carboxylic acid ethyl ester MS m/z 602 ($M^+$); $^1$H NMR (CDCl$_3$) δ 3.8 (s, 3H), 6.75 (s, 1H).

Example 64 cis-4-[(3,5-Bis-trifluoromethyl-benzyl)-(2-dimethylamino-ethoxycarbonyl)-amino]-6,7-dimethoxy-2-methyl-3,4-dihydro-2H-quinoline-1-carboxylic acid ethyl ester MS m/z 636 ($M^+$+1); $^1$H NMR (CDCl$_3$) δ 7.07 (C8, s, 1H), 6.41 (C5, s, 1H), 3.86 (s, 3H), 3.80 (s, 3H).

Example 65 trans-4-[(3,5-Bis-trifluoromethyl-benzyl)-methoxycarbonyl-amino]-6,7-dimethoxy-2-methyl-3,4-dihydro-2H-quinoline-1-carboxylic acid ethyl ester MS m/z 597 ($M^+$+18); $^1$H NMR (CDCl$_3$) δ 7.66 (s, 1H), 3.83 (s, 6H).

Example 66 cis-Benzyl-(6,7-dimethoxy-2-methyl-1,2,3,4-tetrahydro-quinolin-4-yl)-carbamic acid ethyl ester A solution of cis-4-(benzyl-ethoxycarbonyl-amino)-6,7-dimethoxy-2-methyl-3,4-dihydro-2H-quinoline-1-carboxylic acid benzyl ester (Example 4) (1.0 g, 1.9 mmol) in ethanol (20 mL) was placed in a Parr bottle, charged with 10% palladium on carbon (100 mg), and agitated under 50 psi of hydrogen gas on a Parr shaker for 2 h. The mixture was then filtered through a bed of Celite®, eluting with ethyl acetate, and the filtrate concentrated in vacuo. The residue was purified by silica gel chromatography using 30% ethyl acetate/hexanes as eluent to afford 660 mg of the desired final product (89%): MS m/z 204 ($M^+$—PhCH$_2$NHCO$_2$Et—H$_2$+1); $^1$H NMR (CDCl$_3$) δ 1.12 (d, 3H), 1.17 (t, 3H), 3.65 (s, 3H), 3.8 (s, 3H), 6.10 (C5, s, 1H), 6.44 (C8, s, 1H), 7.1–7.3 (m, 5H).

Example 67 cis-(3,5-Bis-trifluoromethyl-benzyl)-(6,7-dimethoxy-2-methyl-1,2,3,4-tetrahydro-quinolin-4-yl)-carbamic acid methyl ester Prepared in a manner analogous to Example 66 using cis-4-[(3,5-bis-trifluoromethyl-benzyl)-methoxycarbonyl-amino]-6,7-dimethoxy-2-methyl-3,4-dihydro-2H-quinoline-1-carboxylic acid benzyl ester (Example 49) MS m/z 507 ($M^+$+1); $^1$H NMR (CDCl$_3$) δ 6.1 (s, 1H), 6.3–6.4 (m, 1H), 7.5–7.6 (m, 2H), 7.7 (s, 1H).

Example 68 cis-4-(Benzyl-ethoxycarbonyl-amino)-6,7-dimethoxy-2-methyl-3,4-dihydro-2H-quinoline-1-carboxylic acid methyl ester A solution of cis-benzyl-(6,7-dimethoxy-2-methyl-1,2,3,4-tetrahydro-quinolin-4-yl)-carbamic acid ethyl ester (Example 66) (111 mg, 0.29 mmol) in anhydrous dichloromethane (2 mL), was treated sequentially with anhydrous pyridine (1 mL), and methyl chloroformate (38 μL, 0.49 mmol). After stirring at room temperature overnight, water (10 mL) and an aqueous 10% KOH solution (10 mL) were added, and the mixture was extracted with ethyl acetate (3×10 mL). The combined organic phases were then washed with 1N HCl (2×10 mL), and then a saturated sodium bicarbonate solution (10 mL). The organic layer was dried over sodium sulfate, filtered and concentrated in vacuo to give 112 mg crude product. Purification by silica gel chromatography using 0–50% ethyl acetate/hexanes as eluent afforded the desired final product (12.6 mg, 10%): MS m/z 443 ($M^+$+1), 460 ($M^{++}$18); $^1$H NMR (CDCl$_3$) δ 7.02 (C8, s, 1H), 6.42 (C5, s, 1H).

Examples 69–106 were prepared from cis-benzyl-(6,7-dimethoxy-2-methyl-1,2,3,4-tetrahydro-quinolin-4-yl)-carbamic acid ethyl ester (Example 66) according to procedures analogous to those of Examples 68, employing the appropriate starting materials.

Example 69 cis-4-(Benzyl-ethoxycarbonyl-amino)-6,7-dimethoxy-2-methyl-3,4-dihydro-2H-quinoline-1-carboxylic acid tert-butyl ester

Example 70 cis-(1-Acetyl-6,7-dimethoxy-2-methyl-1,2,3,4-tetrahydro-quinolin-4-yl)-benzyl-carbamic acid ethyl ester MS m/z 428 ($M^+$+2), 445 ($M^+$+19); $^1$H NMR (CDCl$_3$) δ 6.68 (C8, s, 1H), 6.51 (C5, s, 1H).

Example 71 cis-Benzyl-(1-methanesulfonyl-6,7-dimethoxy-2-methyl-1,2,3,4-tetrahydro-quinolin-4-yl)-carbamic acid ethyl ester MS m/z 463 ($M^+$+1), 480 ($M^+$+18); $^1$H NMR (CDCl$_3$) δ 6.10 (C5, s, 1H), 2.73 (N1, s, 3H).

Example 72 cis-Benzyl-(1-ethylcarbamoyl-6,7-dimethoxy-2-methyl-1,2,3,4-tetrahydro-quinolin-4-yl)-carbamic acid ethyl ester MS m/z 456 (M$^+$+1), 473 (M$^+$+18); $^1$H NMR (CDCl$_3$) δ 6.81 (C8, s, 1H), 6.48 (C5, s, 1H).

Example 73 cis-4-(Benzyl-ethoxycarbonyl-amino)-6,7-dimethoxy-2-methyl-3,4-dihydro-2H-quinoline-1-carboxylic acid butyl ester MS m/z 485 (M$^+$+1), 502 (M$^+$+18); $^1$H NMR (CDCl$_3$) δ 7.04 (C8, s, 1H), 6.43 (C5, s, 1H).

Example 74 cis-Benzyl-(1-butyryl-6,7-dimethoxy-2-methyl-1,2,3,4-tetrahydro-quinolin-4-yl)-carbamic acid ethyl ester MS m/z 455 (M$^+$+1), 472 (M$^+$+18); $^1$H NMR (CDCl$_3$) δ 6.67 (C8, s, 1H), 6.48 (C5, s, 1H).

Example 75 cis-4-(Benzyl-ethoxycarbonyl-amino)-6,7-dimethoxy-2-methyl-3,4-dihydro-2H-quinoline-1-carboxylic acid 2,2,2-trichloro-1,1-dimethyl-ethyl ester MS m/z 588 (M$^+$+1), 606 (M$^+$+19); $^1$H NMR (CDCl$_3$) δ 7.11 (C8, s, 1H), 6.43 (C5, s, 1H).

Example 76 cis-4-(Benzyl-ethoxycarbonyl-amino)-6,7-dimethoxy-2-methyl-3,4-dihydro-2H-quinoline-1-carbothioic acid S-methyl ester MS m/z 459 (M$^+$+1), 467 (M$^+$+18), 280 (M$^+$−178); $^1$H NMR (CDCl$_3$) δ 7.06 (C8, s, 1H), 6.48 (C5, s, 1H), 2.29 (N1, s, 3H).

Example 77 cis-4-(Benzyl-ethoxycarbonyl-amino)-6,7-dimethoxy-2-methyl-3,4-dihydro-2H-quinoline-1-carboxylic acid hexyl ester MS m/z 512 (M$^+$), 530 (M$^+$+18); $^1$H NMR (CDCl$_3$) δ 7.04 (C8, s, 1H), 6.42 (C5, s, 1H).

Example 78 cis-4-(Benzyl-ethoxycarbonyl-amino)-6,7-dimethoxy-2-methyl-3,4-dihydro-2H-quinoline-1-carboxylic acid 2-chloro-ethyl ester MS m/z 490 (M$^+$), 508 (M$^+$+18), 312 (M$^+$−178); $^1$H NMR (CDCl$_3$) δ 7.09 (C8, s, 1H), 6.44 (C5, s, 1H).

Example 79 cis-4-(Benzyl-ethoxycarbonyl-amino)-6,7-dimethoxy-2-methyl-3,4-dihydro-2H-quinoline-1-carboxylic acid phenyl ester MS m/z 504 (M$^+$), 522 (M$^+$+18); $^1$H NMR (CDCl$_3$) δ 6.49 (C5, s, 1H), 3.85 (C6/7, s, 3H), 2.29 (C6/7, s, 3H).

Example 80 cis-4-(Benzyl-ethoxycarbonyl-amino)-6,7-dimethoxy-2-methyl-3,4-dihydro-2H-quinoline-1-carboxylic acid isopropyl ester MS m/z 471 (M$^+$+1), 488 (M$^+$+18); $^1$H NMR (CDCl$_3$) δ 7.07 (C8, s, 1H), 6.43 (C5, s, 1H), 3.86 (C6/7, s, 3H), 3.79 (C6/7, s, 3H).

Example 81 cis-4-(Benzyl-ethoxycarbonyl-amino)-6,7-dimethoxy-2-methyl-3,4-dihydro-2H-quinoline-1-carboxylic acid isobutyl ester MS m/z 485 (M$^+$+1), 502 (M$^+$+18); $^1$H NMR (CDCl$_3$) δ 7.04 (C8, s, 1H), 6.42 (C5, s, 1H), 3.86 (C6/7, s, 3H), 3.80 (C6/7, s, 3H).

Example 82 cis-Benzyl-(1-isobutyryl-6,7-dimethoxy-2-methyl-1,2,3,4-tetrahydro-quinolin-4-yl)-carbamic acid ethyl ester MS m/z 455 (M$^+$+1), 472 (M$^+$+18); $^1$H NMR (CDCl$_3$) δ 6.65 (C8, s, 1H), 6.48 (C5, s, 1H), 1.19 (N1-iPr, d, 6H).

Example 83 cis-Benzyl-(6,7-dimethoxy-2-methyl-1-methylcarbamoyl-1,2,3,4-tetrahydro-quinolin-4-yl)-carbamic acid ethyl ester MS m/z 442 (M$^+$+1), 459 (M$^+$+18); $^1$H NMR (CDCl$_3$) δ 6.81 (C8, s, 1H), 6.49 (C5, s, 1H), 2.77 (N1, s, 3H).

Example 84 cis-Benzyl-[6,7-dimethoxy-2-methyl-1-(3-phenyl-propionyl)-1,2,3,4-tetrahydro-quinolin-4-yl]-carbamic acid ethyl ester MS m/z 517 (M$^+$+1); $^1$H NMR (CDCl$_3$) δ 3.76 (C6/7, s, 3H), 3.75 (C6/7, s, 3H).

Example 85 cis-Benzyl-(6,7-dimethoxy-2-methyl-1-propionyl-1,2,3,4-tetrahydro-quinolin-4-yl)-carbamic acid ethyl ester MS m/z 441 (M$^+$+1), 458 (M$^+$+18); $^1$H NMR (CDCl$_3$) δ 6.69 (C8, s, 1H), 6.50 (C5, s, 1H), 3.84 (C6/7, s, 3H), 3.79 (C6/7, s, 3H).

Example 86 cis-Benzyl-(6,7-dimethoxy-2-methyl-1-trifluoromethanesulfonyl-1,2,3,4-tetrahydro-quinolin-4-yl)-carbamic acid ethyl ester MS m/z 518 (M$^+$+2); $^1$H NMR (CDCl$_3$) δ 3.86 (C6/7, s, 3H), 3.68 (C6/7, s, 3H).

Example 87 cis-Benzyl-[1-(2,2-dimethyl-propionyl)-6,7-dimethoxy-2-methyl-1,2,3,4-tetrahydro-quinolin-4-yl]-carbamic acid ethyl ester MS m/z 469 (M$^+$+1), 486 (M$^+$+18); $^1$H NMR (CDCl$_3$) δ 6.73 (C8, s, 1H), 6.47 (C5, s, 1H), 3.85 (C6/7, s, 3H), 3.79 (C6/7, s, 3H), 1.10 (N1, s, 9H).

Example 88 cis-Benzyl-(1-formyl-6,7-dimethoxy-2-methyl-1,2,3,4-tetrahydro-quinolin-4-yl)-carbamic acid ethyl ester MS m/z 413 (M$^+$+1), 430 (M$^+$+18); $^1$H NMR (CDCl$_3$) δ 8.44 (N1, s, 1H), 6.62 (C8, s, 1H), 6.49 (C5, s, 1H), 3.88 (C6/7, s, 3H), 3.67 (C6/7, s, 3H).

Example 89 cis-Benzyl-(6,7-dimethoxy-2-methyl-1-trifluoroacetyl-1,2,3,4-tetrahydro-quinolin-4-yl)-carbamic acid ethyl ester MS m/z 481 (M$^+$+1), 499 (M$^+$+19); $^1$H NMR (CDCl$_3$) δ 6.81 (C8, s, 1H), 6.49 (C5, s, 1H), 3.85 (C6/7, s, 3H), 3.78 (C6/7, s, 3H).

Example 90 cis-4-(Benzyl-ethoxycarbonyl-amino)-6,7-dimethoxy-2-methyl-3,4-dihydro-2H-quinoline-1-carboxylic acid propyl ester MS m/z 471 (M$^+$+1), 439 (M$^+$+19); $^1$H NMR (CDCl$_3$) δ 7.06 (C8, s, 1H), 6.42 (C5, s, 1H), 3.86 (C6/7, s, 3H), 3.79 (C6/7, s, 3H).

Example 91 cis-4-(Benzyl-ethoxycarbonyl-amino)-6,7-dimethoxy-2-methyl-3,4-dihydro-2H-quinoline-1-carboxylic acid 2,2,2-trichloro-ethyl ester MS m/z 576 (M$^+$+17), 578 (M$^+$+19); $^1$H NMR (CDCl$_3$) δ 7.10 (C8, s, 1H), 6.45 (C5, s, 1H), 3.88 (C6/7, s, 3H), 3.79 (C6/7, s, 3H).

Example 92 cis-Benzyl-[6,7-dimethoxy-2-methyl-1-(2,2,2-trifluoro-ethanesulfonyl)-1,2,3,4-tetrahydro-quinolin-4-yl]-carbamic acid ethyl ester MS m/z 531 (M$^+$+1), 548 (M$^+$+18); $^1$H NMR (CDCl$_3$) δ 6.45 (C5, s, 1H), 3.87 (C6 or 7, s, 3H), 3.78 (C6 or C7, s, 3H).

Example 93 cis-4-(Benzyl-ethoxycarbonyl-amino)-6,7-dimethoxy-2-methyl-3,4-dihydro-2H-quinoline-1-carboxylic acid 2-bromo-ethyl ester MS m/z 536 (M$^+$+1), 554 (M$^+$+19); $^1$H NMR (CDCl$_3$) δ 7.11 (C8, s, 1H), 6.45 (C5, s, 1H).

Example 94 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2,2,2-trichloro-ethyl ester MS m/z 700 (M$^+$+19); $^1$H NMR (CDCl$_3$) δ 7.12 (C8, s, 1H), 6.41 (C5, s, 1H), 1.23 (C2-Me, d, 3H, J=6.2 Hz).

Example 95 cis-4-[(3,5-Bis-trifluoromethyl-benzyl)-methoxycarbonyl-amino]-6,7-dimethoxy-2-methyl-3,4-dihydro-2H-quinoline-1-carboxylic acid isobutyl ester MS m/z 607 (M$^+$+1), 625 (M$^+$+19); $^1$H NMR (CDCl$_3$) δ 7.09 (C8, s, 1H), 6.39 (C5, s, 1H), 1.18 (C2-Me, d, 3H, J=6.1 Hz), 0.94 (iPr, d, 6H, J=6.6 Hz).

Example 96 cis-4-[(3,5-Bis-trifluoromethyl-benzyl)-methoxycarbonyl-amino]-6,7-dimethoxy-2-methyl-3,4-dihydro-2H-quinoline-1-carboxylic acid isopropyl ester MS m/z 593 (M$^+$+1), 611 (M$^+$+19); $^1$H NMR (CDCl$_3$) δ 7.10 (C8, s, 1H), 6.38 (C5, s, 1H), 1.17 (C2-Me, d, 3H, J=6.1 Hz).

Example 97 cis-4-[(3,5-Bis-trifluoromethyl-benzyl)-methoxycarbonyl-amino]-6,7-dimethoxy-2-methyl-3,4-dihydro-2H-quinoline-1-carboxylic acid butyl ester MS m/z 607 (M$^+$+1), 624 (M$^+$+18); $^1$H NMR (CDCl$_3$) δ 7.08 (C8, s, 1H), 6.39 (C5, s, 1H), 1.17 (C2-Me, d, 3H, J=6.2 Hz).

Example 98 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2-chloro-ethyl ester MS m/z 630 (M$^+$+17); $^1$H NMR (CDCl$_3$) δ 7.12 (C8, s, 1H), 6.40 (C5, s, 1H), 1.20 (C2-Me, d, 3H, J=6.2 Hz).

Example 99 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2-bromo-ethyl ester MS m/z 676 (M$^+$+19); $^1$H NMR (CDCl$_3$) δ 7.14 (C8, s, 1H), 6.40 (C5, s, 1H), 1.20 (C2-Me, d, 3H, J=6.2 Hz).

Example 100 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2,2,2-trichloro-1,1-dimethyl-ethyl ester MS m/z 727 (M$^+$+18); $^1$H NMR (CDCl$_3$) δ 7.14 (C8, s, 1H), 6.40 (C5, s, 1H), 1.20 (C2-Me, d, 3H, J=6.2 Hz).

Example 101 cis-4-[(3,5-Bis-trifluoromethyl-benzyl)-methoxycarbonyl-amino]-6,7-dimethoxy-2-methyl-3,4-dihydro-2H-quinoline-1-carboxylic acid tert-butyl ester MS m/z 607 (M$^+$+1), 625 (M$^+$+19); $^1$H NMR (CDCl$_3$) δ 7.08 (C8, s, 1H), 6.39 (C5, s, 1H), 1.15 (C2-Me, d, 3H, J=6.1 Hz).

Example 102 cis-4-[(3,5-Bis-trifluoromethyl-benzyl)-methoxycarbonyl-amino]-6,7-dimethoxy-2-methyl-3,4-dihydro-2H-quinoline-1-carboxylic acid cyclopentyl ester MS m/z 637 (M$^+$+19); $^1$H NMR (CDCl$_3$) δ 7.08 (C8, s, 1H), 6.38 (C5, s, 1H), 1.16 (C2-Me, d, 3H, J=6.2 Hz).

Example 103 cis-4-[(3,5-Bis-trifluoromethyl-benzyl)-methoxycarbonyl-amino]-6,7-dimethoxy-2-methyl-3,4-dihydro-2H-quinoline-1-carboxylic acid methyl ester MS m/z 565 ($M^+$+1), 582 ($M^+$+18); $^1$H NMR (CDCl$_3$) δ 7.06 (C8, s, 1H), 6.39 (C5, s, 1H), 1.17 (C2-Me, d, 3H, J=6.2 Hz).

Example 104 cis-(3,5-Bis-trifluoromethyl-benzyl)-[1-(2,2-dimethyl-propionyl)-6,7-dimethoxy-2-methyl-1,2,3,4-tetrahydro-quinolin-4-yl]-carbamic acid methyl ester MS m/z 592 ($M^+$+2), 609 ($M^+$+19); $^1$H NMR (CDCl$_3$) δ 6.78 (C8, s, 1H), 6.47 (C5, s, 1H), 1.00 (C2-Me, d, 3H, J=6.5 Hz).

Example 105 cis-(3,5-Bis-trifluoromethyl-benzyl)-(6,7-dimethoxy-2-methyl-1-trifluoroacetyl-1,2,3,4-tetrahydro-quinolin-4-yl)-carbamic acid methyl ester MS m/z 602 ($M^+$), 620 ($M^+$+18); $^1$H NMR (CDCl$_3$) δ 6.85 (C8, s, 1H), 6.48 (C5, s, 1H), 1.14 (C2-Me, d, 3H, J=6.4 Hz).

Example 106 cis-(3,5-Bis-trifluoromethyl-benzyl)-(1-butyryl-6,7-dimethoxy-2-methyl-1,2,3,4-tetrahydro-quinolin-4-yl)-carbamic acid methyl ester MS m/z 577 ($M^+$+1); $^1$H NMR (CDCl$_3$) δ 6.72 (C8, s, 1H), 6.47 (C6, s, 1H), 1.08 (C2-Me, d, 3H, J=6.3 Hz).

Example 107A cis-Benzyl-(1-chlorocarbonyl-6,7-dimethoxy-2-methyl-1,2,3,4-tetrahydro-quinolin-4-yl)-carbamic acid ethyl ester To a solution of cis-benzyl-(6,7-dimethoxy-2-methyl-1,2,3,4-tetrahydro-quinolin-4-yl)-carbamic acid ethyl ester (Example 66) (103 mg, 0.268 mmol) in toluene (2.5 mL) was added phosgene (1.0 mL of a 1.93M solution in toluene) and the reaction mixure was heated at reflux for 2 h. The reaction mixture was then concentrated in vacuo to give the desired carbamoyl chloride (110 mg, 92%).

Example 107B cis-4-(Benzyl-ethoxycarbonyl-amino)-6,7-dimethoxy-2-methyl-3,4-dihydro-2H-quinoline-1-carboxylic acid 2,2,2-trifluoro-ethyl ester A solution of benzyl-(1-chlorocarbonyl-6,7-dimethoxy-2-methyl-1,2,3,4-tetrahydro-quinolin-4-yl)-carbamic acid ethyl ester (Example 107A) (24 mg, 0.054 mmol), 2,2,2-trifluoroethanol (0.10 mL, 1.4 mmol), and sodium hydride (56 mg, 60% dispersion in mineral oil, 1.4 mmol) in anhydrous dioxane (1 mL) was stirred at room temperature overnight. The reaction mixture was quenched with 10 mL of water and extracted with ethyl acetate (3×15 mL). The combined organic phases were washed with 10 ml of brine, dried over sodium sulfate, filtered and concentrated in vacuo to give 43 mg of an oil. Purification by silica gel chromatography using 0–50% ethyl acetate/hexanes as eluent afforded the desired final product (15 mg, 58%): MS m/z 510 ($M^+$), 528 ($M^+$+18); $^1$H NMR (CDCl$_3$) δ 6.99 (C8, s, 1H), 6.44 (C5, s, 1H).

Examples 108A and 108B cis-Benzyl-(1-dimethylcarbamoyl-6,7-dimethoxy-2-methyl-1,2,3,4-tetrahydro-quinolin-4-yl)-carbamic acid ethyl ester; and cis-Benzyl-[6,7-dimethoxy-2-methyl-1-(5-oxo-penta-1,3-dienylcarbamoyl)-1,2,3,4-tetrahydro-quinolin-4-yl]-carbamic acid ethyl ester A solution of cis-4-benzyl-(1-chlorocarbonyl-6,7-dimethoxy-2-methyl-1,2,3,4-tetrahydro-quinolin-4-yl)-carbamic acid ethyl ester (Example 107A) (38 mg, 0.085 mmol), pyridine (0.5 mL), and dimethylamine hydrochloride (12 mg, 0.14 mmol) in anhydrous dichloromethane (1 mL) was stirred at room temperature overnight. Then, 10 mL water and 10 mL 2N KOH were added followed by extration with ethyl acetate (3×10 mL). The combined organic phases were washed with 1N HCl (2×10 mL), 10 mL of a saturated sodium bicarbonate solution, and 10 ml of brine. The combined washed organic extracts were dried over sodium sulfate, filtered and concentrated in vacuo. Purification by silica gel chromatography using 0–75% ethyl acetate/hexanes as eluent afforded cis-benzyl-(1-dimethylcarbamoyl-6,7-dimethoxy-2-methyl-1,2,3,4-tetrahydro-quinolin-4-yl)-carbamic acid ethyl ester (Example 108A) (10 mg, 24%) MS m/z 455 ($M^+$), 277 ($M^+$–178); $^1$H NMR (CDCl$_3$) δ 3.79 (C6/7, s, 3H), 3.70 (C6/7, s, 3H), 2.79 (N1, s, 6H); and cis-benzyl-[6,7-dimethoxy-2-methyl-1-(5-oxo-penta-1,3-dienylcarbamoyl)-1,2,3,4-tetrahydro-quinolin-4-yl]-carbamic acid ethyl ester (Example 108B) (7 mg, 15%): MS m/z 508 ($M^+$+1), 329 ($M^+$–178); $^1$H NMR (CDCl$_3$) δ 9.46 (aldehyde, d, 1H), 3.85 (C6/7, s, 3H), 3.79 (C6/7, s, 3H).

Example 109 cis-Benzyl-[6,7-dimethoxy-2-methyl-1-(morpholine-4-carbonyl)-1,2,3,4-tetrahydro-quinolin-4-yl]-carbamic acid ethyl ester Prepared from cis-benzyl-(1-chlorocarbonyl-6,7-dimethoxy-2-methyl-1,2,3,4-tetrahydro-quinolin-4-yl)-carbamic acid ethyl ester (Example 107A) and morpholine in a procedure analgous to Example 108. MS m/z 497 ($M^+$), 319 ($M^+$–178); $^1$H NMR (CDCl$_3$) δ 3.82 (C6/7, s, 3H), 3.72 (C6/7, s, 3H).

Examples 110–120 were prepared from cis-benzyl-(1-chlorocarbonyl-6,7-dimethoxy-2-methyl-1,2,3,4-tetrahydro-quinolin-4-yl)-carbamic acid ethyl ester (Example 107A) and the appropriate alcohol according to procedures analogous to Example 107B.

Example 110 cis-4-(Benzyl-ethoxycarbonyl-amino)-6,7-dimethoxy-2-methyl-3,4-dihydro-2H-quinoline-1-carboxylic acid 2-methoxy-ethyl ester.

MS m/z 488 ($M^+$+2), 505 ($M^+$+19); $^1$H NMR (CDCl$_3$) δ 7.10 (C8, s, 1H), 6.41 (C5, s, 1H), 3.87 (C6/7, s, 3H), 3.79 (C6/7, s, 3H), 3.37 (N1-OMe, s, 3H).

Example 111 cis-4-(Benzyl-ethoxycarbonyl-amino)-6,7-dimethoxy-2-methyl-3,4-dihydro-2H-quinoline-1-carboxylic acid pentyl ester MS m/z 500 ($M^+$+2), 517 ($M^+$+19); $^1$H NMR (CDCl$_3$) δ 7.05 (C8, s, 1H), 6.42 (C5, s, 1H), 3.85 (C6/7, s, 3H), 3.79 (C6/7, s, 3H).

Example 112 cis-4-(Benzyl-ethoxycarbonyl-amino)-6,7-dimethoxy-2-methyl-3,4-dihydro-2H-quinoline-1-carboxylic acid 2,2-dimethyl-propyl ester MS m/z 500 (M$^+$+2), 517 (M$^+$+19); $^1$H NMR (CDCl$_3$) δ 7.06 (C8, s, 1H), 6.42 (C5, s, 1H), 0.93 (N1-tBu, s, 9H).

Example 113 cis-4-(Benzyl-ethoxycarbonyl-amino)-6,7-dimethoxy-2-methyl-3,4-dihydro-2H-quinoline-1-carboxylic acid cyclopentyl ester MS m/z 497 (M$^+$+1), 514 (M$^+$+18); $^1$H NMR (CDCl$_3$) δ 7.06 (C8, s, 1H), 6.41 (C5, s, 1H).

Example 114 cis-4-(Benzyl-ethoxycarbonyl-amino)-6,7-dimethoxy-2-methyl-3,4-dihydro-2H-quinoline-1-carboxylic acid but-2-enyl ester MS m/z 483 (M$^+$+1), 500 (M$^+$+18); $^1$H NMR (CDCl$_3$) δ 7.02 (C8, s, 1H), 6.41 (C5, s, 1H).

Example 115 cis-4-(Benzyl-ethoxycarbonyl-amino)-6,7-dimethoxy-2-methyl-3,4-dihydro-2H-quinoline-1-carboxylic acid allyl ester MS m/z 469 (M$^+$+1), 486 (M$^+$+18); $^1$H NMR (CDCl$_3$) δ 7.05 (C8, s, 1H), 6.43 (C5, s, 1H).

Example 116 cis-4-(Benzyl-ethoxycarbonyl-amino)-6,7-dimethoxy-2-methyl-3,4-dihydro-2H-quinoline-1-carboxylic acid 2-methyl-allyl ester MS m/z 483 (M$^+$+1), 500 (M$^+$+18); $^1$H NMR (CDCl$_3$) δ 7.06 (C8, s, 1H), 6.43 (C5, s, 1H), 1.76 (N1-Me, s, 3H).

Example 117 cis-4-(Benzyl-ethoxycarbonyl-amino)-6,7-dimethoxy-2-methyl-3,4-dihydro-2H-quinoline-1-carboxylic acid thiophen-2-ylmethyl ester MS m/z 525 (M$^+$+1), 542 (M$^+$+18); $^1$H NMR (CDCl$_3$) δ 6.42 (C5, s, 1H), 1.15 (C2-Me, d, 3H).

Example 118 cis-4-(Benzyl-ethoxycarbonyl-amino)-6,7-dimethoxy-2-methyl-3,4-dihydro-2H-quinoline-1-carboxylic acid thiophen-3-ylmethyl ester MS m/z 525 (M$^+$+1), 542 (M$^+$+18); $^1$H NMR (CDCl$_3$) δ 6.96 (C8, s, 1H), 6.43 (C5, s, 1H).

Example 119 cis-4-(Benzyl-ethoxycarbonyl-amino)-6,7-dimethoxy-2-methyl-3,4-dihydro-2H-quinoline-1-carboxylic acid furan-2-ylmethyl ester MS m/z 509 (M$^+$+1), 526 (M$^+$+18) $^1$H NMR (CDCl$_3$) δ 6.98 (C8, s, 1H), 1.15 (C2-Me, d, 3H).

Example 120 cis-4-(Benzyl-ethoxycarbonyl-amino)-6,7-dimethoxy-2-methyl-3,4-dihydro-2H-quinoline-1-carboxylic acid furan-3-ylmethyl ester MS m/z 509 (M$^+$+1), 526 (M$^+$+18); $^1$H NMR (CDCl$_3$) δ 6.96 (C8, s, 1H), 6.41 (C5, s, 1H).

Examples 121–124 were prepared from cis-(3,5-bis-trifluoromethyl-benzyl)-(6,7-dimethoxy-2-methyl-1,2,3,4-tetrahydro-quinolin-4-yl)-carbamic acid methyl ester (Example 67) employing the appropriate starting materials according to procedures analogous to the sequence of Examples 107A and 107B.

Example 121 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2,2-dimethyl-propyl ester.

MS m/z 621 (M$^+$+1), 639 (M$^+$+19); $^1$H NMR (CDCl$_3$) δ 7.10 (C8, s, 1H), 6.39 (C5, s, 1H), 1.19 (C2-Me, d, 3H, J=6.2 Hz).

Example 122 cis-4-[(3,5-Bis-trifluoromethyl-benzyl)-methoxycarbonyl-amino]-6,7-dimethoxy-2-methyl-3,4-dihydro-2H-quinoline-1-carboxylic acid 2,2,2-trifluoro-ethyl ester MS m/z 632 (M$^+$), 651 (M+19); $^1$H NMR (CDCl$_3$) δ 7.00 (C8, s, 1H), 6.40 (C5, s, 1H), 1.20 (C2-Me, d, 3H, J=6.3 Hz).

Example 123 cis-4-[(3,5-Bis-trifluoromethyl-benzyl)-methoxycarbonyl-amino]-6,7-dimethoxy-2-methyl-3,4-dihydro-2H-quinoline-1-carboxylic acid 1-ethyl-propyl ester MS m/z 622 (M$^+$+2), 639 (M$^+$+19); $^1$H NMR (CDCl$_3$) δ 7.10 (C8, s, 1H), 6.39 (C5, s, 1H).

Example 124 cis-4-[(3,5-Bis-trifluoromethyl-benzyl)-methoxycarbonyl-amino]-6,7-dimethoxy-2-methyl-3,4-dihydro-2H-quinoline-1-carboxylic acid 3,3-dimethyl-butyl ester MS m/z 636 (M$^+$+2), 653 (M$^+$+19); $^1$H NMR (CDCl$_3$) δ 7.08 (C8, s, 1H), 6.37 (C5, s, 1H), 1.16 (C2-Me, d, 3H).

Example 125 cis-(3,5-Bis-trifluoromethyl-benzyl)-(1-butyl-6,7-dimethoxy-2-methyl-1,2,3,4-tetrahydro-quinolin-4-yl)-carbamic acid methyl ester A solution of cis-(3,5-bis-trifluoromethyl-benzyl)-(6,7-dimethoxy-2-methyl-1,2,3,4-tetrahydro-quinolin-4-yl)-carbamic acid methyl ester (Example 67) (34 mg, 0.067 mmol), acetic acid (4 μL, 0.067 mmol), butyraldehyde (17 μL, 0.34 mmol), and sodium triacetoxyborohydride (71 μL, 0.34 mmol) in anhydrous dichloroethane (1 mL) were stirred at room temperature overnight. Water (5 mL) was added, the aqueous phase made basic with potassium carbonate, and the mixture was extracted with ethyl acetate (3×10 mL). The combined organic extracts were washed with brine, dried over sodium sulfate, filtered and concentrated in vacuo. Purification by silica gel chromatography using 0–15% ethyl acetate/hexanes as eluent afforded 32 mg of the title compound (82%):MS m/z 563 (M$^+$+1); $^1$H NMR (CDCl$_3$) δ 6.31 (C8, s, 1H), 3.64 (CO$_2$Me, s, 3H), 1.20 (C2-Me, d, 3H, J=6.3 Hz). The hydrochloride salt was prepared by treating an ethereal solution of the free base with an ethereal solution of HCl. Hydrochloride salt:$^1$H NMR (CDCl$_3$) δ 3.83 (CO$_2$Me, s, 3H), 1.20 (C2-Me, d, 3H, J=6.4 Hz).

Examples 126–142 were prepared from cis-(3,5-bis-trifluoromethyl-benzyl)-(6,7-dimethoxy-2-methyl-1,2,3,4-tetrahydro-quinolin-4-yl)-carbamic acid methyl ester (Examples 67) using an analogous procedure to that of Example 125, with the appropriate carboxaldehyde.

Example 126 cis-(3,5-Bis-trifluoromethyl-benzyl)-(1-ethyl-6,7-dimethoxy-2-methyl-1,2,3,4-tetrahydro-quinolin-4-yl)-carbamic acid methyl ester MS m/z 535 (M$^+$+1); $^1$H NMR (CDCl$_3$) δ 3.64 (CO$_2$Me, s, 3H), 1.21 (C2-Me, d, 3H, J=6.3 Hz).

Example 127 cis-(3,5-Bis-trifluoromethyl-benzyl)-(6,7-dimethoxy-2-methyl-1-propyl-1,2,3,4-tetrahydro-quinolin-4-yl)-carbamic acid methyl ester, hydrochloride MS m/z 549 (M$^+$+1); $^1$H NMR (CDCl$_3$) δ 6.28 (C8, s, 1H), 3.64 (CO$_2$Me, s, 3H), 1.20 (C2-Me, d, 3H, J=6.3 Hz).

Example 128 cis-(3,5-Bis-trifluoromethyl-benzyl)-(6,7-dimethoxy-2-methyl-1-pentyl-1,2,3,4-tetrahydro-quinolin-4-yl)-carbamic acid methyl ester, hydrochloride MS m/z 577 (M$^+$+1); $^1$H NMR (CDCl$_3$) δ 6.30 (C8, s, 1H), 3.64 (CO$_2$Me, s, 3H), 1.20 (C2-Me, d, 3H, J=6.3 Hz).

Example 129 cis-(3,5-Bis-trifluoromethyl-benzyl)-(1-hexyl-6,7-dimethoxy-2-methyl-1,2,3,4-tetrahydro-quinolin-4-yl)-carbamic acid methyl ester, hydrochloride MS m/z 591 (M$^+$+1); $^1$H NMR (CDCl$_3$) δ 6.30 (C8, s, 1H), 3.64 (CO$_2$Me, s, 3H), 1.20 (C2-Me, d, 3H, J=6.3 Hz).

Example 130 cis-(3,5-Bis-trifluoromethyl-benzyl)-(6,7-dimethoxy-2-methyl-1-phenethyl-1,2,3,4-tetrahydro-quinolin-4-yl)-carbamic acid methyl ester, hydrochloride
MS m/z 611 (M$^+$+1); $^1$H NMR (CDCl$_3$) δ 6.39 (C8, s, 1H), 3.66 (CO$_2$Me, s, 3H), 1.27 (C2-Me, d, 3H, J=6.2 Hz).

Example 131 cis-(3,5-Bis-trifluoromethyl-benzyl)-[6,7-dimethoxy-2-methyl-1-(3-phenyl-propyl)-1,2,3,4-tetrahydro-quinolin-4-yl]-carbamic acid methyl ester, hydrochloride MS m/z 625 (M$^+$+1); $^1$H NMR (CDCl$_3$) δ 6.06 (C8, s, 1H), 1.17 (C2-Me, d, 3H, J=6.2 Hz).

Example 132 cis-(1-Benzyl-6,7-dimethoxy-2-methyl-1,2,3,4-tetrahydro-quinolin-4-yl)-(3,5-bis-trifluoromethyl-benzyl)-carbamic acid methyl ester, hydrochloride MS m/z 597 (M$^+$+1); $^1$H NMR (CDCl$_3$) δ 6.15 (C8, s, 1H), 1.18 (C2-Me, d, 3H, J=6.3 Hz).

Example 133 cis-(3,5-Bis-trifluoromethyl-benzyl)-(1-isobutyl-6,7-dimethoxy-2-methyl-1,2,3,4-tetrahydro-quinolin-4-yl)-carbamic acid methyl ester, hydrochloride MS m/z 563 (M$^+$+1); $^1$H NMR (CDCl$_3$) δ 6.28 (C8, s, 3H), 3.83 (CO$_2$Me, s, 3H), 1.19 (C2-Me, d, 3H, J=6.3 Hz).

Example 134 cis-(3,5-Bis-trifluoromethyl-benzyl)-[6,7-dimethoxy-2-methyl-1-(3-methyl-butyl)-1,2,3,4-tetrahydro-quinolin-4-yl]-carbamic acid methyl ester, hydrochloride MS m/z 577 (M$^+$+1); $^1$H NMR (CDCl$_3$) δ 3.64 (CO$_2$Me, s, 3H), 1.20 (C2-Me, d, 3H, J=6.3 Hz), 0.95 (iPr, d, 6H, J=6.6 Hz).

Example 135 cis-(3,5-Bis-trifluoromethyl-benzyl)-[1-(3,3-dimethyl-butyl)-6,7-dimethoxy-2-methyl-1,2,3,4-tetrahydro-quinolin-4-yl]-carbamic acid methyl ester, hydrochloride MS m/z 591 (M$^+$+1); $^1$H NMR (CDCl$_3$) δ 3.63 (CO$_2$Me, s, 3H), 0.98 (tBu, d, 9H).

Example 136 cis-(3,5-Bis-trifluoromethyl-benzyl)-(1-but-2-enyl-6,7-dimethoxy-2-methyl-1,2,3,4-tetrahydro-quinolin-4-yl)-carbamic acid methyl ester, hydrochloride MS m/z 561 (M$^+$+1); $^1$H NMR (CDCl$_3$) δ 3.64 (CO$_2$Me, s, 3H), 1.18 (C2-Me, d, 3H, J=6.1 Hz).

Example 137 cis-(3,5-Bis-trifluoromethyl-benzyl)-(1-cyclopropylmethyl-6,7-dimethoxy-2-methyl-1,2,3,4-tetrahydro-quinolin-4-yl)-carbamic acid methyl ester, hydrochloride MS m/z 561 (M$^+$+1); $^1$H NMR (CDCl$_3$) δ 6.50 (C8, s, 1H), 3.64 (CO$_2$Me, s, 3H).

Example 138 cis-(3,5-Bis-trifluoromethyl-benzyl)-[1-(2-ethyl-butyl)-6,7-dimethoxy-2-methyl-1,2,3,4-tetrahydro-quinolin-4-yl)-carbamic acid methyl ester, hydrochloride MS m/z 591 (M$^+$+1); $^1$H NMR (CDCl$_3$) δ 3.63 (CO$_2$Me, s, 3H), 1.16 (C2-Me, d, 3H, J=6.2 Hz).

Example 139 cis-(3,5-Bis-trifluoromethyl-benzyl)-(6,7-dimethoxy-2-methyl-1-thiophen-3-ylmethyl-1,2,3,4-tetrahydro-quinolin-4-yl)-carbamic acid methyl ester, hydrochloride MS m/z 603 (M$^+$+1); $^1$H NMR (CDCl$_3$) δ 6.29 (C8, s, 1H), 1.22 (C2-Me, d, 3H).

Example 140 cis-(3,5-Bis-trifluoromethyl-benzyl)-[6,7-dimethoxy-2-methyl-1-(4,4,4-trifluoro-butyl)-1,2,3,4-tetrahydro-quinolin-4-yl]-carbamic acid methyl ester, hydrochloride MS m/z 617 (M$^+$+1); $^1$H NMR (CDCl$_3$) δ 3.65 (CO$_2$Me, s, 3H), 1.21 (C2-Me, d, 3H, J=6.0 Hz).

Example 141 cis-(3,5-Bis-trifluoromethyl-benzyl)-[6,7-dimethoxy-2-methyl-1-(2-methyl-butyl)-1,2,3,4-tetrahydro-quinolin-4-yl]-carbamic acid methyl ester, hydrochloride MS m/z 577 (M$^+$+1); $^1$H NMR (CDCl$_3$) δ 3.64 (CO$_2$Me, s, 3H), 1.18 (C2-Me, d, 3H, J=6.2 Hz).

Example 142 cis-(3,5-Bis-trifluoromethyl-benzyl)-(1-cyclohexylmethyl-6,7-dimethoxy-2-methyl-1,2,3,4-tetrahydro-quinolin-4-yl)-carbamic acid methyl ester, hydrochloride MS m/z 603 (M$^+$+1); $^1$H NMR (CDCl$_3$) δ 3.64 (CO$_2$Me, s, 3H), 1.19 (C2-Me, d, 3H, J=6.3 Hz).

Example 143A

7-Hydroxy-6-methoxy-2-methyl-4-oxo-3,4-dihydro-2H-quinoline-1-carboxylic acid ethyl ester A solution of 6,7-dimethoxy-2-methyl-4-oxo-3,4-dihydro-2H-quinoline-1-carboxylic acid ethyl ester (10.0 g, 34.1 mmol) and sodium cyanide (8.35 g, 170 mmol) in dimethylsulfoxide (35 mL) was heated at 130° C. for 16 h. Water (100 mL) was added, the mixture was saturated with ammonium chloride, and then extracted with ethyl acetate (4×100 mL). The combined organic extracts were washed with saturated sodium bicarbonate solution (50 mL), brine (25 mL), dried over sodium sulfate, filtered and concentrated in vacuo. Purification by silica gel chromatography using 0–50% ethyl acetate/hexanes as eluent afforded the title compound (5.10 g, 54%).

Example 143B

7-Hydroxy-4-hydroxyimino-6-methoxy-2-methyl-3,4-dihydro-2H-quinoline-1-carboxylic acid ethyl ester 7-Hydroxy-6-methoxy-2-methyl-4-oxo-3,4-dihydro-2H-quinoline-1-carboxylic acid ethyl ester (5.10 g, 18.3 mmol) was dissolved in ethanol (100 mL), and hydroxylamine hydrochloride (3.81 g, 54.8 mmol) was added, followed by sodium acetate (3.74 g, 45.7 mmol). The mixture was heated at reflux for 2 h and then left to stand at room temperature overnight. Water (100 mL) was added, and the volatiles were removed in vacuo to give a yellow slurry. This slurry was filtered and washed with water to give the title compound as a fine powder (4.755 g, 89%).

Example 143C cis- and trans-4-Amino-7-hydroxy-6-methoxy-2-methyl-3,4-dihydro-2H-quinoline-1-carboxylic acid ethyl ester To a stirred solution of 7-hydroxy-4-hydroxyimino-6-methoxy-2-methyl-3,4-dihydro-2H-quinoline-1-carboxylic acid ethyl ester (4.76 g, 16.2 mmol) in ethanol (100 mL) and aqueous 2N KOH (50 mL, 97 mmol) was added nickel-aluminum alloy (7.6 g, 50% Ni, 65 mmol) in portions. Additional nickel-aluminum catalyst was added after 75 min. (0.95 g, 8.9 mmol), and after 30 min more (0.95 g, 8.9 mmol). After stirring 2 h more, the reaction mixture was filtered through a pad of Celite®, rinsing with ethanol, and then water. To the filtrate was added 6N HCl (15 mL) with stirring, followed by the dropwise addition of saturated sodium bicarbonate solution. Ethyl acetate (50 mL) was added, and the solution was stirred vigorously for 20 min. The aqueous layer was separated and extracted with ethyl acetate (2×150 mL). The aqueous layer was then saturated with sodium chloride, and extracted with ethyl acetate (4×75 mL). The organic phases were combined, washed with brine, dried over sodium sulfate, filtered, and concentrated in vacuo to give the title compound as a mixture of stereoisomers (4.49 g, 99%).

Example 143D cis-4-(3,5-Bis-trifluoromethyl-benzylamino)-7-hydroxy-6-methoxy-2-methyl-3,4-dihydro-2H-quinoline-1-carboxylic acid ethyl ester To a stirred suspension of cis-4-amino-7-hydroxy-6-methoxy-2-methyl-3,4-dihydro-2H-quinoline-1-carboxylic acid ethyl ester (4.49 g, 16.0 mmol) in 1,2-dichloroethane (100 mL) was added 3,5-bis(trifluoromethyl)benzaldehyde (2.6 mL, 16.0 mmol), followed by acetic acid (0.9 mL, 16.0 mmol). After 45 min, sodium triacetoxyborohydride (5.1 g, 24.0 mmol) was added, and the reaction was stirred at room temperature overnight. Water (75 mL) and ethyl acetate (75 mL) were added to the mixture which was then made basic to pH 10 with solid potassium carbonate. The mixture was then extracted with ethyl acetate (2×100 mL). The combined organic phases were washed with brine, dried over sodium sulfate, filtered, and concentrated in vacuo to give 8.17 g of crude product. Purification by silica gel chromatography using 0–30% ethyl acetate/hexanes as eluent afforded 4.90 g of the title compound (60%).

Example 143E cis-4-[(3,5-Bis-trifluoromethyl-benzyl)-methoxycarbonyl-amino]-6-methoxy-7-methoxycarbonyloxy-2-methyl-3,4-dihydro-2H-quinoline-1-carboxylic acid ethyl ester To a stirred solution of cis-4-(3,5-bis-trifluoromethyl-benzylamino)-7-hydroxy-6-methoxy-2-methyl-3,4-dihydro-2H-quinoline-1-carboxylic acid ethyl ester (4.9 g, 9.7 mmol) and anhydrous pyridine (30 mL, 371 mmol) in anhydrous dichloromethane (60 mL) cooled to 0° C. was slowly added methyl chloroformate (7.5 mL, 97 mmol). After stirring at room temperature for 2 days, water (50 mL) and an aqueous 2N KOH solution (50 mL) were added to the reaction mixture, which was then extracted with ethyl acetate (3×100 mL). The combined organic phases were washed with saturated sodium bicarbonate solution (50 mL), brine, dried over sodium sulfate, filtered and concentrated in vacuo to give 5.89 g of crude product. Purification by silica gel chromatography using 0–25% ethyl acetate/hexanes as eluent afforded 5.05 g of the title compound (84%): MS m/z 623 (M$^+$+1), 641 (M$^+$+19); $^1$H NMR (CDCl$_3$) δ 7.32 (C8, s, 1H), 6.49 (C5, s, 1H), 1.15 (C2-Me, d, 3H, J=6.1 Hz).

Example 144 cis-4-[(3,5-Bis-trifluoromethyl-benzyl)-methoxycarbonyl-amino]-7-hydroxy-6-methoxy-2-methyl-3,4-dihydro-2H-quinoline-1-carboxylic acid ethyl ester A solution of cis-4-[(3,5-bis-trifluoromethyl-benzyl)-methoxycarbonyl-amino]-6-methoxy-7- methoxycarbonyloxy-2-methyl-3,4-dihydro-2H-quinoline-1-carboxylic acid ethyl ester (5.0 g, 8.0 mmol) and potassium carbonate (2.2 g, 16 mmol) in methanol (45 mL) was stirred at room temperature. After 12 hours, water (100 mL) was added, and the volatiles were removed in vacuo. The mixture was then extracted with ethyl acetate (3×100 mL), the combined organic extracts were washed with saturated sodium bicarbonate solution (50 mL), dried over sodium sulfate, filtered and concentrated in vacuo to give 4.67 g of crude product. Purification by silica gel chromatography using 0–25% ethyl acetate/hexanes as eluent afforded 2.27 g of the title compound (50%). MS m/z 566 ($M^+$+2), 583 ($M^+$+19); $^1$H NMR (CDCl$_3$) δ 7.07 (C8, s, 1H), 6.36 (C5, s, 1H).

Example 145 cis-4-[(3,5-Bis-trifluoromethyl-benzyl)-methoxycarbonyl-amino]-6-methoxy-2-methyl-7-octyloxy-3,4-dihydro-2H-quinoline-1-carboxylic acid ethyl ester A solution of cis-4-[(3,5-bis-trifluoromethyl-benzyl)-methoxycarbonyl-amino]-7-hydroxy-6-methoxy-2-methyl-3,4-dihydro-2H-quinoline-1-carboxylic acid ethyl ester (30 mg, 0.053 mmol), triphenylphosphine (28 mg, 0.11 mmol), 1-octanol (33 μL, 0.21 mmol), and bis-(N-methylpiperazinyl)-azodicarboxamide (30 mg, 0.11 mmol) in benzene (1 mL) was stirred at room temperature for 2 days. Purification of the solution directly by silica gel chromatography using 0–20% ethyl acetate/hexanes as eluent afforded the title compound (18 mg, 50%). MS m/z 695 ($M^+$+19), 376 ($M^+$–300); $^1$H NMR (CDCl$_3$) δ 7.08 (C8, s, 1H), 6.40 (C5, s, 1H), 1.17 (C2-Me, d, 3H, J=6.1 Hz).

Examples 146–163 were prepared in a manner analogous to Example 145 by substituting the appropriate alcohol in the reaction with cis-4-[(3,5-bis-trifluoromethyl-benzyl)-methoxycarbonyl-amino]-7-hydroxy-6-methoxy-2-methyl-3,4-dihydro-2H-quinoline-1-carboxylic acid ethyl ester.

Example 146 cis-4-[(3,5-Bis-trifluoromethyl-benzyl)-methoxycarbonyl-amino]-7-(2-dimethylamino-ethoxy)-6-methoxy-2-methyl-3,4-dihydro-2H-quinoline-1-carboxylic acid ethyl ester MS m/z 637 ($M^+$+2); $^1$H NMR (CDCl$_3$) δ 7.09 (C8, s, 1H), 6.39 (C5, s, 1H), 1.15 (C2-Me, d, 3H, J=6.2 Hz).

Example 147 cis-4-[(3,5-Bis-trifluoromethyl-benzyl)-methoxycarbonyl-amino]-7-cyclopentyloxy-6-methoxy-2-methyl-3,4-dihydro-2H-quinoline-1-carboxylic acid ethyl ester MS m/z 623 ($M^+$–300); $^1$H NMR (CDCl$_3$) δ 7.06 (C8, s, 1H), 6.40 (C5, s, 1H).

Example 148 cis-4-[(3,5-Bis-trifluoromethyl-benzyl)-methoxycarbonyl-amino]-7-isopropoxy-6-methoxy-2-methyl-3,4-dihydro-2H-quinoline-1-carboxylic acid ethyl ester MS m/z 306 ($M^+$–300); $^1$H NMR (CDCl$_3$) δ 7.09 (C8, s, 1H), 6.41 (C5, s, 1H).

Example 149 cis-7-Benzyloxy-4-[(3,5-bis-trifluoromethyl-benzyl)-methoxycarbonyl-amino]-6-methoxy-2-methyl-3,4-dihydro-2H-quinoline-1-carboxylic acid ethyl ester MS m/z 656 ($M^+$+2), 673 ($M^+$+19); $^1$H NMR (CDCl$_3$) δ 7.12 (C8, s, 1H), 6.43 (C6, s, 1H), 1.14 (C2-Me, d, 3H, J=6.2 Hz).

Example 150 cis-4-[(3,5-Bis-trifluoromethyl-benzyl)-methoxycarbonyl-amino]-6-methoxy-2-methyl-7-(3-methyl-butoxy)-3,4-dihydro-2H-quinoline-1-carboxylic acid ethyl ester MS m/z 636 ($M^+$+2), 653 ($M^+$+19); $^1$H NMR (CDCl$_3$) δ 7.09 (C8, s, 1H), 6.39 (C6, s, 1H), 1.17 (C2-Me, d, 3H, J=6.2 Hz), 0.96 (C7-iPr, d, 6H, J=6.1 Hz).

Example 151 cis-4-[(3,5-Bis-trifluoromethyl-benzyl)-methoxycarbonyl-amino]-7-butoxy-6-methoxy-2-methyl-3,4-dihydro-2H-quinoline-1-carboxylic acid ethyl ester MS m/z 622 ($M^+$+2), 639 ($M^+$+19); $^1$H NMR (CDCl$_3$) δ 7.08 (C8, s, 1H), 6.40 (C6, s, 1H), 1.17 (C2-Me, d, 3H, J=6.1 Hz), 0.97 (C7-O-nBu, d, 3H, J=7.4 Hz).

Example 152 cis-4-[(3,5-Bis-trifluoromethyl-benzyl)-methoxycarbonyl-amino]-6-methoxy-2-methyl-7-(pyridin-2-ylmethoxy)-3,4-dihydro-2H-quinoline-1-carboxylic acid ethyl ester MS m/z 657 ($M^+$+2); $^1$H NMR (CDCl$_3$) δ 7.08 (C8, s, 1H), 6.44 (C6, s, 1H).

Example 153 cis-4-[(3,5-Bis-trifluoromethyl-benzyl)-methoxycarbonyl-amino]-6-methoxy-2-methyl-7-(pyridin-3-ylmethoxy)-3,4-dihydro-2H-quinoline-1-carboxylic acid ethyl ester MS m/z 657 ($M^+$+2); $^1$H NMR (CDCl$_3$) δ 1.24 (CO$_2$Et, t, 3H, J=7.1 Hz), 1.14 (C2-Me, d, 3H, J=6.0 Hz).

Example 154 cis-4-[(3,5-Bis-trifluoromethyl-benzyl)-methoxycarbonyl-amino]-6-methoxy-7-(2-methoxy-ethoxy)-2-methyl-3,4-dihydro-2H-quinoline-1-carboxylic acid ethyl ester MS m/z 624 ($M^+$+2), 641 ($M^+$+19); $^1$H NMR (CDCl$_3$) δ 7.10 (C8, s, 1H), 6.39 (C6, s, 1H), 1.15 (C2-Me, d, 3H, J=6.0 Hz).

Example 155 cis-4-[(3,5-Bis-trifluoromethyl-benzyl)-methoxycarbonyl-amino]-7-hexyloxy-6-methoxy-2-methyl-3,4-dihydro-2H-quinoline-1-carboxylic acid ethyl ester MS m/z 650 ($M^+$+2), 667 ($M^+$+19); $^1$H NMR (CDCl$_3$) δ 7.07 (C8, s, 1H), 6.40 (C5, s, 1H), 1.17 (C2-Me, d, 3H, J=6.1 Hz).

Example 156 cis-4-[(3,5-Bis-trifluoromethyl-benzyl)-methoxycarbonyl-amino]-7-decyloxy-6-methoxy-2-methyl-3,4-dihydro-2H-quinoline-1-carboxylic acid ethyl ester MS m/z 723 ($M^+$+19), 405 ($M^+$–300); $^1$H NMR (CDCl$_3$) δ 7.09 (C8, s, 1H), 6.39 (C5, s, 1H), 1.17 (C2-Me, d, 3H, J=6.1 Hz).

Example 157 cis-4-[(3,5-Bis-trifluoromethyl-benzyl)-methoxycarbonyl-amino]-7-ethoxy-6-methoxy-2-methyl-3,4-dihydro-2H-quinoline-1-carboxylic acid ethyl ester $^1$H NMR (CDCl$_3$) δ 7.08 (C8, s, 1H), 6.39 (C5, s, 1H), 1.46 (C7 OEt, t, 3H, J=7.0 Hz), 1.29 (CO$_2$Et, t, 3H, J=7.1 Hz), 1.16 (C2-Me, d, 3H, J=6.2 Hz).

Example 158 cis-4-[(3,5-Bis-trifluoromethyl-benzyl)-methoxycarbonyl-amino]-7-(5-dimethylamino-pentyloxy)-6-methoxy-2-methyl-3,4-dihydro-2H-quinoline-1-carboxylic acid ethyl ester MS m/z 678 (M$^+$+1); $^1$H NMR (CDCl$_3$) δ 7.06 (C8, s, 1H), 6.39 (C5, s, 1H).

Example 159 cis-4-[(3,5-Bis-trifluoromethyl-benzyl)-methoxycarbonyl-amino]-6-methoxy-2-methyl-7-(pyridin-4-ylmethoxy)-3,4-dihydro-2H-quinoline-1-carboxylic acid ethyl ester MS m/z 656 (M$^+$+1); $^1$H NMR (CDCl$_3$) δ 7.07 (C8, s, 1H), 6.44 (C5, s, 1H), 1.14 (C2-Me, d, 3H, J=6.1 Hz).

Example 160 cis-4-[(3,5-Bis-trifluoromethyl-benzyl)-methoxycarbonyl-amino]-6-methoxy-2-methyl-7-pentyloxy-3,4-dihydro-2H-quinoline-1-carboxylic acid ethyl ester MS m/z 635 (M$^+$+1), 652 (M$^+$+18); $^1$H NMR (CDCl$_3$) δ 7.08 (C8, s, 1H), 6.40 (C5, s, 1H).

Example 161 cis-4-[(3,5-Bis-trifluoromethyl-benzyl)-methoxycarbonyl-amino]-7-(6-hydroxy-hexyloxy)-6-methoxy-2-methyl-3,4-dihydro-2H-quinoline-1-carboxylic acid ethyl ester MS m/z 665 (M$^+$+1), 682 (M$^+$+18); $^1$H NMR (CDCl$_3$) δ 7.10 (C8, s, 1H), 6.39 (C5, s, 1H), 1.16 (C2-Me, d, 3H, J=6.2 Hz).

Example 162 cis-4-[(3,5-Bis-trifluoromethyl-benzyl)-methoxycarbonyl-amino]-7-(10-hydroxy-decyloxy)-6-methoxy-2-methyl-3,4-dihydro-2H-quinoline-1-carboxylic acid ethyl ester MS m/z 721 (M$^+$+1); $^1$H NMR (CDCl$_3$) δ 7.08 (C8, s, 1H), 1.16 (C2-Me, d, 3H, J=6.0 Hz).

Example 163 cis-4-[(3,5-Bis-trifluoromethyl-benzyl)-methoxycarbonyl-amino]-7-(5-ethoxycarbonyl-pentyloxy)-6-methoxy-2-methyl-3,4-dihydro-2H-quinoline-1-carboxylic acid ethyl ester MS m/z 707 (M$^+$+1), 725 (M$^+$+19); $^1$H NMR (CDCl$_3$) δ 7.08 (C8, s, 1H), 6.39 (C5, s, 1H), 1.16 (C2-Me, d, 3H, J=6.1 Hz).

Example 164 cis-4-[(3,5-Bis-trifluoromethyl-benzyl)-methoxycarbonyl-amino]-7-(5-carboxy-pentyloxy)-6-methoxy-2-methyl-3,4-dihydro-2H-quinoline-1-carboxylic acid ethyl ester Prepared by treating a solution of cis-4-[(3,5-bis-trifluoromethyl-benzyl)-methoxycarbonyl-amino]-7-(5-ethoxycarbonyl-pentyloxy)-6-methoxy-2-methyl-3,4-dihydro-2H-quinoline-1-carboxylic acid ethyl ester (Example 163) (27 mg, 0.04 mmol) in 0.6 mL THF and 0.2 mL methanol with an aqueous 1M lithium hydroxide solution (0.2 mL, 0.2 mmol) at room temperature. After 45 minutes, acidification with 1N HCl and extraction with ethyl acetate, drying the organic extracts over sodium sulfate, and concentration under reduced pressure provided 25 mg of the title compound. MS m/z 697 (M$^+$+19), 378 (M$^+$−300); $^1$H NMR (CDCl$_3$) δ 6.39 (C5, s, 1H), 3.79 (C6-OMe, s, 3H), 1.16 (Me, d, 3H, J=6.1 Hz).

Example 165A

6-Benzyloxy-7-methoxy-2-methyl-4-oxo-3,4-dihydro-2H-quinoline-1-carboxylic acid ethyl ester 6-Benzyloxy-4,7-dimethoxy-quinoline (1.6 g, 5.5 mmol) was dissolved in anhydrous tetrahydrofuran (20 mL). The mixture was cooled to −78° C., and methyl magnesium chloride (3.8 mL of a 3.0M solution in tetrahydrofuran, 11.4 mmol) was added. The mixture was stirred at −78° C. for 1 h, then methyl chloroformate (1.1 mL, 11.4 mmol) was added. The reaction was warmed to room temperature overnight, then 12 mL of a 1N aqueous HCl solution was added. After 30 minutes, 15 mL of water was added and the tetrahydrofuran was removed in vacuo. After adding 40 mL of water, the resulting aqueous phase was extracted with ethyl acetate (3×40 mL). The organic phases were combined and washed with 20 mL each of 1N HCL, saturated aqueous sodium bicarbonate, and brine, before being dried over sodium sulfate, filtered, and concentrated in vacuo to give 1.99 g of the title product (99%).

Example 165B

6-Benzyloxy-4-hydroxyimino-7-methoxy-2-methyl-3,4-dihydro-2H-quinoline-1-carboxylic acid ethyl ester To a stirred solution of 6-benzyloxy-7-methoxy-2-methyl-4-oxo-3,4-dihydro-2H-quinoline-1-carboxylic acid ethyl ester (1.99 g, 5.39 mmol) in 95% ethanol (20 mL) was added hydroxylamine hydrochloride (1.1 g, 16 mmol) and sodium acetate (1.1 g, 14 mmol), and the mixture was heated at reflux. After 2 h, water (50 mL) was added, and the mixture was extracted with ethyl acetate (3×50 mL). The combined organic phases were washed with brine (30 mL), dried over sodium sulfate, filtered and concentrated in vacuo to give 2.05 g of the title compound (99%).

Example 165C cis-4-Amino-6-hydroxy-7-methoxy-2-methyl-3,4-dihydro-2H-quinoline-1-carboxylic acid ethyl ester To a stirred solution of 6-benzyloxy-4-hydroxyimino-7-methoxy-2-methyl-3,4-dihydro-2H-quinoline-1-carboxylic acid ethyl ester (2.05 g, 5.33 mmol), in ethanol (20 mL) and aqueous 2N KOH (16 mL, 32 mmol) was added aluminum-nickel alloy (1.82 g, 50% Ni, 21.2 mmol) in portions. The reaction was stirred at room temperature for 1.5 h, then additional aluminum-nickel alloy (1.82 g, 21.2 mmol) was added, and the reaction was stirred for 3 h. Additional aqueous 2N KOH (20 mL, 40 mmol) was added, and the reaction was stirred for 1 h. The mixture was then filtered through a bed of Celite®, rinsing with ethyl acetate. The filtrate was concentrated in vacuo, and the mixture was extracted with ethyl acetate (3×50 mL). The combined organic phases were washed with brine (30 mL), dried over sodium sulfate, filtered and concentrated in vacuo to give 0.65 g crude product. Purification by silica gel chromatography using 0–5% methanol/dichloromethane as eluent afforded 387 mg of the title compound (26%).

Example 165D cis-4-(3,5-Bis-trifluoromethyl-benzylamino)-6-hydroxy-7-methoxy-2-methyl-3,4-dihydro-2H-quinoline-1-carboxylic acid ethyl ester To a stirred suspension of cis-4-amino-6-hydroxy-7-methoxy-2-methyl-3,4-dihydro-2H-quinoline-1-carboxylic acid ethyl ester (387 mg, 1.38 mmol) in dichloromethane (9 mL) was added 3,5-bis(trifluoromethyl)benzaldehyde (225 µL, 1.38 mmol), followed by acetic acid (80 µL, 1.4 mmol). The reaction was stirred at room temperature for 1 h, then sodium triacetoxyborohydride (440 mg, 2.08 mmol) was added. The reaction was stirred at room temperature for 5 h. Water (5 mL) was added, and the mixture was slowly basified to pH 10 with solid potassium carbonate. The mixture was then extracted with ethyl acetate (3×10 mL), the combined organic phases were washed with brine, dried over sodium sulfate, filtered, and concentrated in vacuo to give 680 mg crude product. Purification by silica gel chromatography using 0–25% ethyl acetate/hexanes as eluent afforded 458 mg of the title compound (65%).

Example 165E cis-4-[(3,5-Bis-trifluoromethyl-benzyl)-methoxycarbonyl-amino]-7-methoxy-6-methoxycarbonyloxy-2-methyl-3,4-dihydro-2H-quinoline-1-carboxylic acid ethyl ester To a stirred solution of cis-4-(3,5-bis-trifluoromethyl-benzylamino)-6-hydroxy-7-methoxy-2-methyl-3,4-dihydro-2H-quinoline-1-carboxylic acid ethyl ester (450 mg, 0.89 mmol) and anhydrous pyridine (2.5 mL) in anhydrous dichloromethane (5 mL) at 0° C. was slowly added methyl chloroformate (0.7 mL, 9 mmol). After stirring overnight at room temperature, water (10 mL) and an aqueous 2N KOH solution (10 mL) were added, the mixture was extracted with ethyl acetate (3×10 mL), and the combined organic phases were washed with 1N HCl (3×10 mL), saturated sodium bicarbonate solution (10 mL), and then brine (10 mL). The organic layer was dried over sodium sulfate, filtered and concentrated in vacuo to give 551 mg crude product. Purification by silica gel chromatography using 0–25% ethyl acetate/hexanes as eluent afforded 448 mg of the title compound (90%): MS m/z 641 (M$^+$+19); $^1$H NMR (CDCl$_3$) δ 7.22 (C8, s, 1H), 6.70 (C5, s, 1H), 1.18 (C2-Me, d, 3H, J=6.1 Hz).

Example 166 cis-4-[(3,5-Bis-trifluoromethyl-benzyl)-methoxycarbonyl-amino]-6-hydroxy-7-methoxy-2-methyl-3,4-dihydro-2H-quinoline-1-carboxylic acid ethyl ester A solution of cis-4-[(3,5-bis-trifluoromethyl-benzyl)-methoxycarbonyl-amino]-7-methoxy-6-methoxycarbonyloxy-2-methyl-3,4-dihydro-2H-quinoline-1-carboxylic acid ethyl ester (500 mg, 0.80 mmol) and potassium carbonate (222 mg, 1.6 mmol) in methanol (5 mL) was stirred at room temperature overnight. A small amount of water was added, and the methanol was removed in vacuo. Additional water (20 mL) was added and the aqueous mixture was extracted with ethyl acetate (3×15 mL). The combined organic extracts were washed with a saturated sodium bicarbonate solution (10 mL), brine (10 mL), and then dried over sodium sulfate, filtered and concentrated in vacuo to give 412 mg crude product. Purification by silica gel chromatography using 0–20% ethyl acetate/hexanes as eluent afforded 378 mg of the title compound (84%): MS m/z 565 (M$^+$+1), 582 (M$^+$+18); $^1$H NMR (CDCl$_3$) δ 7.08 (C8, s, 1H), 6.52 (C5, s, 1H), 1.15 (C2-Me, d, 3H, J=6.0 Hz).

Example 167 cis-4-[(3,5-Bis-trifluoromethyl-benzyl)-methoxycarbonyl-amino]-6-ethoxy-7-methoxy-2-methyl-3,4-dihydro-2H-quinoline-1-carboxylic acid ethyl ester A solution of cis-4-[(3,5-bis-trifluoromethyl-benzyl)-methoxycarbonyl-amino]-6-hydroxy-7-methoxy-2-methyl-3,4-dihydro-2H-quinoline-1-carboxylic acid ethyl ester (30 mg, 0.053 mmol), triphenylphosphine (28 mg, 0.11 mmol), ethanol (16 µL, 0.79 mmol), and bis-(N-methylpiperazinyl)-azodicarboxamide (30 mg, 0.11 mmol) in benzene (1 mL) was stirred at room temperature for 12 hours. Purification of the solution directly by silica gel chromatography using 0–20% ethyl acetate/hexanes as eluent afforded 20 mg of the title compound (67%): MS m/z 593 (M$^+$), 610 (M$^+$+17); $^1$H NMR (CDCl$_3$) δ 6.39 (C5, s, 1H), 1.17 (C2-Me, d, 3H, J=6.2 Hz).

Examples 168–171 were prepared in a manner analogous to Example 167 by substituting the appropriate alcohol in the reaction with cis-4-[(3,5-bis-trifluoromethyl-benzyl)-methoxycarbonyl-amino]-6-hydroxy-7-methoxy-2-methyl-3,4-dihydro-2H-quinoline-1-carboxylic acid ethyl ester.

Example 168 cis-4-[(3,5-Bis-trifluoromethyl-benzyl)-methoxycarbonyl-amino]-6-isopropoxy-7-methoxy-2-methyl-3,4-dihydro-2H-quinoline-1-carboxylic acid ethyl ester MS m/z 624 (M$^+$+18); $^1$H NMR (CDCl$_3$) δ 6.42 (C5, s, 1H), 1.18 (C2-Me, d, 3H, J=6.1 Hz).

Example 169 cis-4-[(3,5-Bis-trifluoromethyl-benzyl)-methoxycarbonyl-amino]-7-methoxy-2-methyl-6-propoxy-3,4-dihydro-2H-quinoline-1-carboxylic acid ethyl ester MS (Thermospray) m/z 607 (M$^+$+1), 624 (M$^+$+18); $^1$H NMR (CDCl$_3$) δ 6.39 (C5, s, 1H), 1.17 (C2-Me, d, 3H, J=6.1 Hz).

Example 170 cis-4-[(3,5-Bis-trifluoromethyl-benzyl)-methoxycarbonyl-amino]-6-butoxy-7-methoxy-2-methyl-3,4-dihydro-2H-quinoline-1-carboxylic acid ethyl ester MS m/z 621 (M$^+$+1), 638 (M$^+$+18); $^1$H NMR (CDCl$_3$) δ 6.39 (C5, s, 1H), 1.17 (C2-Me, d, 3H, J=6.2 Hz).

Example 171 cis-4-[(3,5-Bis-trifluoromethyl-benzyl)-methoxycarbonyl-amino]-6-cyclopentyloxy-7-methoxy-2-methyl-3,4-dihydro-2H-quinoline-1-carboxylic acid ethyl ester MS m/z 633 (M$^+$+1), 650 (M$^+$+18); $^1$H NMR (CDCl$_3$) δ 6.38 (C5, s, 1H), 1.18 (C2-Me, d, 3H, J=6.1 Hz).

Example 172 cis-4-{[1-(3,5-Bis-trifluoromethyl-phenyl)-ethyl]-methoxycarbonyl-amino}-6,7-dimethoxy-2-methyl-3,4-dihydro-2H-quinoline-1-carboxylic acid ethyl ester To a pre-dried flask under nitrogen atmosphere was added cis-4-[(3,5-bis-trifluoromethyl-benzyl)-methoxycarbonyl-amino]-6,7-dimethoxy-2-methyl-3,4-dihydro-2H-quinoline-1-carboxylic acid ethyl ester (0.200 g, 0.346 mmol) and tetrahydrofuran (2 mL). The solution was cooled to −78° C. and a 1.83 M solution of n-butyl lithium in hexanes (0.23 g, 0.41 mmol) was added. The reaction was stirred at −78° C. for 45 min, then methyl iodide (0.026 mL, 0.41 mmol) was added and the reaction was warmed to 0° C. and stirred for 90 min. The reaction was quenched with saturated ammonium chloride solution, and the mixture was extracted three times with dichloromethane. The combined organic layers were dried over magnesium sulfate, filtered and concentrated in vacuo to give crude product. Purification by silica gel chromatography using 20% ethyl acetate/hexanes, followed by 70% ether/hexanes as eluent afforded the desired methylated product. MS m/z 593 (M$^+$+H); $^1$H NMR (CDCl$_3$) δ 7.85 (bs, 1H), 7.8 (bs, 2H), 7.05 (bs, 1H), 6.5 (bs, 1H), 3.9 (s, 3H), 3.85 (s, 3H), 1.65 (d, 1.5H, J=7 Hz), 1.05 (d, 1.5H, J=7.0 Hz).

Examples 173 and 174 were prepared in optically enriched form by resolution of the corresponding racemate indicated, or an intermediate in its synthesis, using the methods described in the specification.

Example 173

[2R,4S]4-[(3,5-Bis-trifluoromethyl-benzyl)-methoxycarbonyl-amino]-6,7-dimethoxy-2-methyl-3,4-dihydro-2H-quinoline-1-carboxylic acid ethyl ester.

Example 16.

Example 174

[2R,4S]4-[(3,5-Bis-trifluoromethyl-benzyl)-ethoxycarbonyl-amino]-6,7-dimethoxy-2-methyl-3,4-dihydro-2H-qiuinoline-1-carboxylic acid ethyl ester.

Example 44.

What is claimed is:

1. A compound of the Formula I

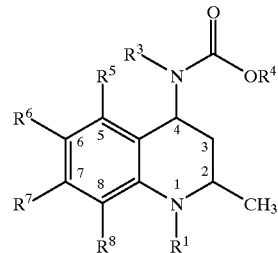

Formula I a prodrug thereof, or a pharmaceutically acceptable salt of said compound or of said prodrug;

wherein R$^1$ is Y, W—X, or W—Y;

wherein W is a carbonyl, thiocarbonyl, sulfinyl or sulfonyl;

X is —O—Y, —S—Y, —N(H)—Y or —N—(Y)$_2$;

wherein Y for each occurrence is independently Z or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with Z;

wherein Z is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said Z substituent is optionally mono-, di- or tri-substituted independently with halo, (C$_2$–C$_6$)alkenyl, (C$_1$–C$_6$)alkyl, hydroxy, (C$_1$–C$_6$)alkoxy, (C$_1$–C$_4$) alkylthio, amino, nitro, cyano, oxo, carboxyl, (C$_1$–C$_6$)alkyloxycarbonyl, mono-N- or di-N,N-(C$_1$–C$_6$)alkylamino wherein said (C$_1$–C$_6$) alkyl substituent is optionally mono-, di- or tri-substituted independently with halo, hydroxy, (C$_1$–C$_6$)alkoxy, (C$_1$–C$_4$)alkylthio, amino, nitro, cyano, oxo, carboxyl, (C$_1$–C$_6$)alkyloxycarbonyl, mono-N- or di-N,N-(C$_1$–C$_6$)alkylamino, said (C$_1$–C$_6$)alkyl substituent is also optionally substituted with from one to nine fluorines;

R$^3$ is hydrogen or Q;

wherein Q is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with V;

wherein V is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said V substituent is optionally mono-, di-, tri-, or tetra-substituted independently with halo, $(C_1-C_6)$ alkyl, $(C_2-C_6)$alkenyl, hydroxy, $(C_1-C_6)$alkoxy, $(C_1-C_4)$alkylthio, amino, nitro, cyano, oxo, carbamoyl, mono-N- or di-N,N-$(C_1-C_6)$ alkylcarbamoyl, carboxyl, $(C_1-C_6)$ alkyloxycarbonyl, mono-N- or di-N,N-$(C_1-C_6)$ alkylamino wherein said $(C_1-C_6)$alkyl or $(C_2-C_6)$ alkenyl substituent is optionally mono-, di- or tri-substituted independently with hydroxy, $(C_1-C_6)$ alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$alkyl or $(C_2-C_6)$alkenyl substituents are also optionally substituted with from one to nine fluorines;

$R^4$ is $Q^1$ or $V^1$ wherein $Q^1$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V^1$;

wherein $V^1$ is a partially saturated, fully saturated or fully unsaturated three to six membered ring optionally having one to two heteroatoms selected independently from oxygen, sulfur and nitrogen;

wherein said $V^1$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R^3$ must contain V or $R^4$ must contain $V^1$; and $R^5$, $R^6$, $R^7$ and $R^8$ are each independently hydrogen, hydroxy or oxy wherein said oxy is substituted with T or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with T;

wherein T is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said T substituent is optionally mono-, di- or tri-substituted independently with halo, $(C_1-C_6)$ alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines with the proviso that $R^1$ is not $(C_1-C_6)$alkyl.

2. A compound as recited in claim 1 wherein the $C^2$ methyl is beta;

the $C^4$ nitrogen is beta;

$R^1$ is W—X;

W is carbonyl, thiocarbonyl or sulfonyl;

X is —O—Y—, S—Y—, —N(H)—Y— or —N—(Y)$_2$—;

Y for each occurrence is independently Z or $(C_1-C_4)$alkyl, said $(C_1-C_4)$alkyl optionally having from one to nine fluorines or said $(C_1-C_4)$alkyl optionally mono-substituted with Z wherein Z is a partially saturated, fully saturated or fully unsaturated three to six membered ring optionally having one to two heteroatoms selected independently from oxygen, sulfur and nitrogen;

wherein said Z substituent is optionally mono-, di- or tri-substituted independently with halo, $(C_1-C_4)$ alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl substituent is also optionally substituted with from one to nine fluorines;

$R^3$ is Q—V wherein Q is $(C_1-C_4)$alkylene and V is a five or six membered partially saturated, fully saturated or fully unsaturated ring optionally having one to three heteroatoms selected independently from oxygen, sulfur and nitrogen;

wherein said V ring is optionally mono-, di-, tri- or tetra-substituted independently with halo, $(C_1-C_6)$ alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$ alkyl optionally having from one to nine fluorines;

$R^4$ is $(C_1-C_4)$alkyl;

$R^6$ and $R^7$ are each independently hydrogen, or $(C_1-C_6)$ alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, ($C_1$–$C_6$) alkyl, hydroxy, ($C_1$–$C_6$)alkoxy, ($C_1$–$C_4$)alkylthio, amino, oxo, carboxy, ($C_1$–$C_6$)alkyloxycarbonyl, mono-N- or di-N,N-($C_1$–$C_6$)alkylamino wherein said ($C_1$–$C_6$)alkyl substituent optionally has from one to nine fluorines; and $R^5$ and $R^8$ are H, or a pharmaceutically acceptable salt thereof.

3. A compound as recited in claim 2 wherein

W is carbonyl;

X is O—Y wherein Y is ($C_1$–$C_4$)alkyl, said ($C_1$–$C_4$)alkyl optionally having from one to nine fluorines;

Q is ($C_1$–$C_4$)alkylene and V is phenyl, pyridinyl, or pyrimidinyl;

wherein said V ring is optionally mono-, di- or tri-substituted independently with halo, ($C_1$–$C_6$)alkyl, hydroxy, ($C_1$–$C_6$)alkoxy, nitro, cyano or oxo wherein said ($C_1$–$C_6$)alkyl substituent optionally has from one to nine fluorines;

$R^6$ and $R^7$ are each independently hydrogen or ($C_1$–$C_3$) alkoxy, said ($C_1$–$C_3$)alkoxy optionally having from one to seven fluorines, or a pharmaceutically acceptable salt thereof.

4. A compound as recited in claim 3 wherein

Q is methylene and V is phenyl or pyridinyl;

wherein said V ring is optionally mono-, di- or tri-substituted independently with halo, nitro or ($C_1$–$C_2$) alkyl, wherein said ($C_1$–$C_2$)alkyl substituent optionally has from one to five fluorines, or a pharmaceutically acceptable salt thereof.

5. A compound as recited in claim 1 wherein said compound is:

[2R,4S]4-[(3,5-dichloro-benzyl)-methoxycarbonyl-amino]-6,7-dimethoxy-2-methyl-3,4-dihydro-2H-quinoline-1-carboxylic acid ethyl ester;

[2R,4S]4-[(3,5-dinitro-benzyl)-methoxycarbonyl-amino]-6,7-dimethoxy-2-methyl-3,4-dihydro-2H-quinoline-1-carboxylic acid ethyl ester;

[2R,4S]4-[(2,6-dichloro-pyridin-4-ylmethyl)-methoxycarbonyl-amino]-6,7-dimethoxy-2-methyl-3, 4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3, 4-dihydro-2H-quinoline-1-carboxylic acid ethyl ester;

[2R,4S]4-[(3,5-bis-trifluoromethyl-benzyl)-methoxycarbonyl-amino]-6-methoxy-2-methyl-3,4-dihydro-2H-quinoline-1-carboxylic acid ethyl ester; or

[2R,4S]4-[(3,5-bis-trifluoromethyl-benzyl)-methoxycarbonyl-amino]-7-methoxy-2-methyl-3,4-dihydro-2H-quinoline-1-carboxylic acid ethyl ester, or a pharmaceutically acceptable salt of said compounds.

6. A compound as recited in claim 1 wherein said compound is:

[2R,4S]4-[(3,5-bis-trifluoromethyl-benzyl)-methoxycarbonyl-amino]-6,7-dimethoxy-2-methyl-3, 4-dihydro-2H-quinoline-1-carboxylic acid isopropyl ester;

[2R,4S]4-[(3,5-bis-trifluoromethyl-benzyl)-ethoxycarbonyl-amino]-6,7-dimethoxy-2-methyl-3,4-dihydro-2H-quinoline-1-carboxylic acid ethyl ester;

[2R,4S]4-[(3,5-bis-trifluoromethyl-benzyl)-methoxycarbonyl-amino]-6,7-dimethoxy-2-methyl-3, 4-dihydro-2H-quinoline-1-carboxylic acid 2,2,2-trifluoro-ethyl ester;

[2R,4S]4-[(3,5-bis-trifluoromethyl-benzyl)-methoxycarbonyl-amino]-6,7-dimethoxy-2-methyl-3, 4-dihydro-2H-quinoline-1-carboxylic acid propyl ester;

[2R,4S]4-[(3,5-bis-trifluoromethyl-benzyl)-methoxycarbonyl-amino]-6,7-dimethoxy-2-methyl-3, 4-dihydro-2H-quinoline-1-carboxylic acid tert-butyl ester; or

[2R,4S]4-[(3,5-bis-trifluoromethyl-benzyl)-methoxycarbonyl-amino]-2-methyl-6-trifluoromethoxy-3,4-dihydro-2H-quinoline-1-carboxylic acid ethyl ester, or a pharmaceutically acceptable salt of said compounds.

7. A compound as recited in claim 4 wherein

Y is ethyl;

$R^3$ is 3,5-dichlorophenylmethyl;

$R^4$ is methyl; and $R^6$ and $R^7$ are each methoxy, or a pharmaceutically acceptable salt thereof.

8. A compound as recited in claim 4 wherein

Y is ethyl;

$R^3$ is 3,5-dinitrophenylmethyl;

$R^4$ is methyl; and $R^6$ and $R^7$ are each methoxy, or a pharmaceutically acceptable salt thereof.

9. A compound as recited in claim 4 wherein

Y is ethyl;

$R^3$ is 2,6-dichloropyridin-4-ylmethyl;

$R^4$ is methyl; and $R^6$ and $R^7$ are each methoxy, or a pharmaceutically acceptable salt thereof.

10. A compound as recited in claim 4 wherein

Y is ethyl;

$R^3$ is 3,5-bis-trifluoromethylphenylmethyl;

$R^4$ is methyl; and $R^6$ and $R^7$ are each methoxy, or a pharmaceutically acceptable salt thereof.

11. A compound as recited in claim 4 wherein

Y is ethyl;

$R^3$ is 3,5-bis-trifluoromethylphenylmethyl;

$R^4$ is methyl;

$R^6$ is methoxy; and $R^7$ is hydrogen, or a pharmaceutically acceptable salt thereof.

12. A compound as recited in claim 4 wherein

Y is ethyl;

$R^3$ is 3,5-bis-trifluoromethylphenylmethyl;

$R^4$ is methyl;

$R^6$ is hydrogen; and $R^7$ is methoxy, or a pharmaceutically acceptable salt thereof.

13. A compound as recited in claim 4 wherein

Y is isopropyl;

$R^3$ is 3,5-bis-trifluoromethylphenylmethyl;

$R^4$ is methyl; and $R^6$ and $R^7$ are each methoxy, or a pharmaceutically acceptable salt thereof.

14. A compound as recited in claim 4 wherein

Y is ethyl;

$R^3$ is 3,5-bis-trifluoromethylphenylmethyl;

$R^4$ is ethyl; and $R^6$ and $R^7$ are each methoxy, or a pharmaceutically acceptable salt thereof.

15. A compound as recited in claim 4 wherein
Y is 2,2,2,-trifluoroethyl;
$R^3$ is 3,5-bis-trifluoromethylphenylmethyl;
$R^4$ is methyl; and
$R^6$ and $R^7$ are each methoxy, or a pharmaceutically acceptable salt thereof.

16. A compound as recited in claim 4 wherein
Y is n-propyl;
$R^3$ is 3,5-bis-trifluoromethylphenylmethyl;
$R^4$ is methyl; and
$R^6$ and $R^7$ are each methoxy, or a pharmaceutically acceptable salt thereof.

17. A compound as recited in claim 4 wherein
Y is tert-butyl;
$R^3$ is 3,5-bis-trifluoromethylphenylmethyl;
$R^4$ is methyl; and
$R^6$ and $R^7$ are each methoxy, or a pharmaceutically acceptable salt thereof.

18. A compound as recited in claim 4 wherein
Y is ethyl;
$R^3$ is 3,5-bis-trifluoromethylphenylmethyl;
$R^4$ is methyl;
$R^6$ is trifluoromethoxy; and
$R^7$ is hydrogen, or a pharmaceutically acceptable salt thereof.

19. A compound as recited in claim 1 wherein
the $C^2$ methyl is beta;
the $C^4$ nitrogen is beta:
$R^1$ is W—Y;
W is carbonyl, thiocarbonyl or sulfonyl;
Y is $(C_1-C_6)$alkyl, said $(C_1-C_6)$alkyl optionally having from one to nine fluorines or said $(C_1-C_6)$alkyl is optionally mono-substituted with Z;
  wherein Z is a partially saturated, fully saturated or fully unsaturated three to six membered ring optionally having one to two heteroatoms selected independently from oxygen, sulfur and nitrogen;
  wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl substituent optionally substituted with from one to nine fluorines;
$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;
  wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;
$R^4$ is $(C_1-C_4)$alkyl;
$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;
  wherein T is a partially saturated, fully saturated or fully unsaturated five to six membered ring optionally having one to two heteroatoms selected independently from oxygen, sulfur and nitrogen;
  wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and
$R^5$ and $R^8$ are H, or a pharmaceutically acceptable salt thereof.

20. A compound as recited in claim 19 wherein
W is carbonyl;
Y is $(C_1-C_4)$alkyl, said $(C_1-C_4)$alkyl optionally having from one to nine fluorines;
Q is $(C_1-C_4)$alkylene and V is phenyl, pyridinyl, or pyrimidinyl;
  wherein said V ring is optionally mono-, di- or tri-substituted independently with halo, $(C_1-C_6)$alkyl, hydroxy, $(C_1-C_6)$alkoxy, nitro, cyano or oxo wherein said $(C_1-C_6)$alkyl substituent optionally has from one to nine fluorines; and
$R^6$ and $R^7$ are each independently hydrogen or $(C_1-C_3)$alkoxy, said $(C_1-C_3)$alkoxy optionally having from one to seven fluorines, or a pharmaceutically acceptable salt thereof.

21. A compound as recited in claim 1 wherein said compound is [2R,4S](3,5-bis-trifluoromethyl-benzyl)-(1-butyryl-6,7-dimethoxy-2-methyl-1,2,3,4-tetrahydro-quinolin-4-yl)-carbamic acid methyl ester or a pharmaceutically acceptable salt of said compound.

22. A compound as recited in claim 20 wherein
Y is n-propyl;
$R^3$ is 3,5-bis-trifluoromethylphenylmethyl;
$R^4$ is methyl; and
$R^6$ and $R^7$ are each methoxy, or a pharmaceutically acceptable salt thereof.

23. A compound as recited in claim 1 wherein
the $C^2$ methyl is beta;
the $C^4$ nitrogen is beta:
$R^1$ is Y;
Y is $(C_2-C_6)$alkenyl or $(C_1-C_6)$alkyl, said $(C_2-C_8)$alkenyl or $(C_1-C_8)$alkyl optionally having from one to nine fluorines or said $(C_2-C_6)$alkenyl or $(C_1-C_6)$alkyl optionally mono-substituted with Z;
  wherein Z is a partially saturated, fully saturated or fully unsaturated three to six membered ring optionally having one to two heteroatoms selected independently from oxygen, sulfur and nitrogen;
  wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally substituted with from one to nine fluorines;
$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;
  wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H, or a pharmaceutically acceptable salt thereof.

24. A compound as recited in claim 23 wherein

Y is $(C_1-C_4)$alkyl, said $(C_1-C_4)$alkyl optionally having from one to nine fluorines;

Q is $(C_1-C_4)$alkylene and V is phenyl, pyridinyl, or pyrimidinyl;

wherein said V ring is optionally mono-, di- or tri-substituted independently with halo, $(C_1-C_6)$alkyl, hydroxy, $(C_1-C_6)$alkoxy, nitro, cyano or oxo wherein said $(C_1-C_6)$alkyl substituent optionally has from one to nine fluorines; and $R^6$ and $R^7$ are each independently hydrogen or $(C_1-C_3)$alkoxy, said $(C_1-C_3)$alkoxy optionally having from one to seven fluorines, or a pharmaceutically acceptable salt thereof.

25. A compound as recited in claim 1 wherein the $C^2$ methyl is beta;

the $C^4$ nitrogen is beta:

$R^1$ is Z;

wherein Z is a partially saturated, fully saturated or fully unsaturated three to six membered ring optionally having one to two heteroatoms selected independently from oxygen, sulfur and nitrogen;

wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally having one to nine fluorines;

$R^3$ is Q—V;

wherein Q is $(C_1-C_4)$alkyl and V is a five or six membered partially saturated, fully saturated or fully unsaturated ring optionally having one to three heteroatoms selected independently from oxygen, sulfur and nitrogen;

wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H, or a pharmaceutically acceptable salt thereof.

26. A compound as recited in claim 1 wherein the $C^2$ methyl is beta;

the $C^4$ nitrogen is beta:

$R^1$ is W—Z;

W is carbonyl, thiocarbonyl or sulfonyl;

Z is a partially saturated, fully saturated or fully unsaturated three to six membered ring optionally having one to two heteroatoms selected independently from oxygen, sulfur and nitrogen;

wherein said Z substituent is optionally mono-, di- or tri-substituted independently with halo, $(C_1-C_4)$alkyl, $(C_1-C_4)$alkoxy, $(C_1-C_4)$alkylthio, nitro, cyano, oxo, or $(C_1-C_6)$alkyloxycarbonyl, said $(C_1-C_4)$alkyl optionally having from one to nine fluorines;

$R^3$ is Q—V wherein Q is $(C_1-C_4)$alkyl and V is a five or six membered partially saturated, fully saturated or fully unsaturated ring optionally having one to three heteroatoms selected independently from oxygen, sulfur and nitrogen;

wherein said V ring is optionally mono-, di-, tri- or tetra-substituted independently with halo, $(C_1-C_6)$alkyl, hydroxy, $(C_1-C_6)$alkoxy, nitro, cyano or oxo wherein said $(C_1-C_6)$alkyl substituent is optionally mono-, di- or tri-substituted independently with $(C_1-C_6)$alkoxy or $(C_1-C_4)$alkylthio or said $(C_1-C_6)$alkyl optionally having from one to nine fluorines;

$R^4$ is $(C_1-C_4)$alkyl;

$R^6$ and $R^7$ are each independently hydrogen or $(C_1-C_6)$alkoxy, said $(C_1-C_6)$alkoxy optionally having from one to nine fluorines or said $(C_1-C_6)$alkoxy is optionally mono-substituted with T;

wherein T is a partially saturated, fully saturated or fully unsaturated five to six membered ring optionally having one to two heteroatoms selected independently from oxygen, sulfur and nitrogen;

wherein said T substituent is optionally mono-, di- or tri-substituted independently with halo, $(C_1-C_6)$alkyl, hydroxy, $(C_1-C_6)$alkoxy, $(C_1-C_4)$alkylthio, amino, oxo, carboxy, $(C_1-C_6)$alkyloxycarbonyl, mono-N- or di-N,N-$(C_1-C_6)$alkylamino wherein said $(C_1-C_6)$alkyl substituent optionally has from one to nine fluorines; and $R^5$ and $R^8$ are H, or a pharmaceutically acceptable salt thereof.

27. A method for treating atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, reperfusion injury, vascular complications of diabetes, obesity or endotoxemia treating amount of a compound of claim 1, a prodrug thereof, or a pharmaceutically acceptable salt of said compound or of said prodrug.

28. A method as recited in claim 27 wherein atherosclerosis is treated.

29. A method as recited in claim 27 wherein peripheral vascular disease is treated.

30. A method as recited in claim 27 wherein dyslipidemia is treated.

31. A method as recited in claim 27 wherein hyperbetalipoproteinemia is treated.

32. A method as recited in claim 27 wherein hypoalphalipoproteinemia is treated.

33. A method as recited in claim 27 wherein hypercholesterolemia is treated.

34. A method as recited in claim 27 wherein hypertriglyceridemia is treated.

35. A method as recited in claim 27 wherein cardiovascular disorders are treated.

36. A pharmaceutical composition which comprises a therapeutically effective amount of a compound of claim 1, a prodrug thereof, or a pharmaceutically acceptable salt of said compound or of said prodrug and a pharmaceutically acceptable carrier.

37. A pharmaceutical composition for the treatment of atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal which comprise a therapeutically effective amount of a compound of claim 1, a prodrug thereof, or a pharmaceutically acceptable salt of said compound or of said prodrug and a pharmaceutically acceptable carrier.

38. A pharmaceutical composition for the treatment of atherosclerosis in a mammal which comprises an atherosclerosis treating amount of a compound of claim 1, a prodrug thereof, or a pharmaceutically acceptable salt of said compound or of said prodrug and a pharmaceutically acceptable carrier.

39. A method for treating atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, reperfusion injury, angioplastic restenosis, hypertension, vascular complications of diabetes, obesity or endotoxemia in a mammal by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, angina, reperfusion injury, angioplastic restenosis, hypertension, reperfusion injury, vascular complications of diabetes, obesity or endotoxemia treating amount of a compound of Formula I

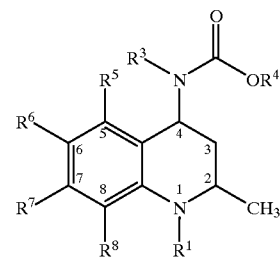

a prodrug thereof, or a pharmaceutically acceptable salt of said compound or of said prodrug;

wherein $R^1$ is hydrogen, Y, W—X, or W—Y;

wherein W is a carbonyl, thiocarbonyl, sulfinyl or sulfonyl;

X is —O—Y, —S—Y, —N(H)—Y or —N—$(Y)_2$;

wherein Y for each occurrence is independently Z or a fully saturated, partially unsaturated or fully unsaturated one to ten membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with Z;

wherein Z is a partially saturated, fully saturated or fully unsaturated three to eight membered ring optionally having one to four heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

wherein said Z substituent is optionally mono-, di- or tri-substituted independently with halo, $(C_2-C_6)$alkenyl, $(C_1-C_6)$alkyl, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino wherein said $(C_1-C_6)$ alkyl substituent is optionally mono-, di- or tri-substituted independently with halo, hydroxy, $(C_1-C_6)$alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines;

$R^3$ is hydrogen or Q;

wherein Q is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with V;

wherein V is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said V substituent is optionally mono-, di-, tri-, or tetra-substituted independently with halo, $(C_1-C_6)$ alkyl, $(C_2-C_6)$alkenyl, hydroxy, $(C_1-C_6)$alkoxy, $(C_1-C_4)$alkylthio, amino, nitro, cyano, oxo, carbamoyl, mono-N- or di-N,N-$(C_1-C_6)$ alkylcarbamoyl, carboxyl, $(C_1-C_6)$ alkyloxycarbonyl, mono-N- or di-N,N-$(C_1-C_6)$ alkylamino wherein said $(C_1-C_6)$alkyl or $(C_2-C_6)$ alkenyl substituent is optionally mono-, di- or tri-substituted independently with hydroxy, $(C_1-C_6)$ alkoxy, $(C_1-C_4)$alkylthio, amino, nitro, cyano, oxo, carboxyl, $(C_1-C_6)$alkyloxycarbonyl, mono-N- or di-N,N-$(C_1-C_6)$alkylamino, said $(C_1-C_6)$alkyl or $(C_2-C_6)$alkenyl substituents are also optionally substituted with from one to nine fluorines;

$R^4$ is $Q^1$ or $V^1$ wherein $Q^1$ is a fully saturated, partially unsaturated or fully unsaturated one to six membered straight or branched carbon chain wherein the carbons, other than the connecting carbon, may optionally be replaced with one heteroatom selected from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono-, or di-substituted with oxo, and said carbon chain is optionally mono-substituted with $V^1$;

wherein $V^1$ is a partially saturated, fully saturated or fully unsaturated three to six membered ring optionally having one to two heteroatoms selected independently from oxygen, sulfur and nitrogen;

wherein said $V^1$ substituent is optionally mono-, di-, tri-, or tetra-substituted independently with halo, $(C_1-C_6)$alkyl, $(C_1-C_6)$alkoxy, amino, nitro, cyano, $(C_1-C_6)$alkyloxycarbonyl, mono-N- or di-N,N-$(C_1-C_6)$alkylamino wherein said $(C_1-C_6)$alkyl substituent is optionally mono-substituted with oxo, said $(C_1-C_6)$alkyl substituent is also optionally substituted with from one to nine fluorines;

wherein either $R^3$ must contain V or $R^4$ must contain $V^1$; and $R^5$, $R^6$, $R^7$ and $R^8$ are each independently hydrogen, hydroxy or oxy wherein said oxy is substituted with T or a partially saturated, fully saturated or fully unsaturated one to twelve membered straight or branched carbon chain wherein the carbons, other than the connecting carbon, may optionally be replaced with one or two heteroatoms selected independently from oxygen, sulfur and nitrogen and said carbon is optionally mono-, di- or tri-substituted independently with halo, said carbon is optionally mono-substituted with hydroxy, said carbon is optionally mono-substituted with oxo, said sulfur is optionally mono- or di-substituted with oxo, said nitrogen is optionally mono- or di-substituted with oxo, and said carbon chain is optionally mono-substituted with T;

wherein T is a partially saturated, fully saturated or fully unsaturated three to eight membered ring optionally having one to four heteroatoms selected independently from oxygen, sulfur and nitrogen, or a bicyclic ring consisting of two fused partially saturated, fully saturated or fully unsaturated three to six membered rings, taken independently, optionally having one to four heteroatoms selected independently from nitrogen, sulfur and oxygen;

wherein said T substituent is optionally mono-, di- or tri-substituted independently with halo, $(C_1-C_6)$ alkyl, $(C_2-C_6)$alkenyl, hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino wherein said $(C_1-C_6)$alkyl substituent is optionally mono-, di- or tri-substituted independently with hydroxy, $(C_1-C_6)$alkoxy, $(C_1-C_4)$alkylthio, amino, nitro, cyano, oxo, carboxy, $(C_1-C_6)$alkyloxycarbonyl, mono-N- or di-N,N-$(C_1-C_6)$alkylamino, said $(C_1-C_6)$alkyl substituent is also optionally substituted with from one to nine fluorines.

40. A method as recited in claim 39 wherein atherosclerosis is treated with an atherosclerosis treating amount of a Formula I compound or a pharmaceutically acceptable salt of said compound.

41. A method as recited in claim 39 wherein dyslipidemia is treated with a dyslipidemia treating amount of a Formula I compound or a pharmaceutically acceptable salt of said compound.

42. A method as recited in claim 39 wherein hyperbetalipoproteinemia is treated with a hyperbetalipoproteinemia treating amount of a Formula I compound or a pharmaceutically acceptable salt of said compound.

43. A method as recited in claim 39 wherein hypoalphalipoproteinemia is treated with a hypoalphalipoproteinemia treating amount of a Formula I compound or a pharmaceutically acceptable salt of said compound.

44. A method as recited in claim 39 wherein hypercholesterolemia is treated with an hypercholesterolemia treating amount of a Formula I compound.

* * * * *